(12) United States Patent
Nan et al.

(10) Patent No.: US 9,216,962 B2
(45) Date of Patent: Dec. 22, 2015

(54) THIAZOLE COMPOUNDS, METHODS FOR PREPARATION AND USE THEREOF

(75) Inventors: Fajun Nan, Shanghai (CN); Fei Chen, Shanghai (CN); Yangming Zhang, Shanghai (CN); Jia Li, Shanghai (CN); Yubo Zhou, Shanghai (CN); Mingbo Su, Shanghai (CN); Jian Ding, Shanghai (CN); Linghua Meng, Shanghai (CN); Xin Xie, Shanghai (CN); Shixian Wang, Shanghai (CN)

(73) Assignee: Shanghai Puyi Chemical Co., Ltd., Shanghai (CN)

( * ) Notice: Subject to any disclaimer, the term of this patent is extended or adjusted under 35 U.S.C. 154(b) by 0 days.

(21) Appl. No.: 14/116,944

(22) PCT Filed: May 7, 2012

(86) PCT No.: PCT/CN2012/075142
§ 371 (c)(1),
(2), (4) Date: Feb. 10, 2014

(87) PCT Pub. No.: WO2012/152208
PCT Pub. Date: Nov. 15, 2012

(65) Prior Publication Data
US 2014/0148600 A1   May 29, 2014

(30) Foreign Application Priority Data

May 10, 2011   (CN) .......................... 2011 1 0120207

(51) Int. Cl.
*C07D 417/00* (2006.01)
*C07D 277/56* (2006.01)
*C07D 277/58* (2006.01)
*C07D 277/60* (2006.01)
*C07D 417/14* (2006.01)
*C07D 417/04* (2006.01)

(52) U.S. Cl.
CPC ............ *C07D 277/56* (2013.01); *C07D 277/58* (2013.01); *C07D 277/60* (2013.01); *C07D 417/04* (2013.01); *C07D 417/14* (2013.01)

(58) Field of Classification Search
CPC ..................................................... C07D 417/04
See application file for complete search history.

(56) References Cited

FOREIGN PATENT DOCUMENTS

| CN | 101048374 | 10/2007 |
|---|---|---|
| CN | 101918389 | 12/2010 |
| WO | 2006097460 | 9/2006 |
| WO | 2008019025 | 2/2008 |

*Primary Examiner* — Heidi Reese
(74) *Attorney, Agent, or Firm* — Avery N. Goldstein; Blue Filament Law

(57) ABSTRACT

The present invention relates to thiazole compounds of formula I, the method for preparation and use thereof. More specifically, the present invention relates to novel derivatives of natural product largazole, the method for preparing them and their uses for treatments against tumor and multiple sclerosis as inhibitors of histone deacetylase.

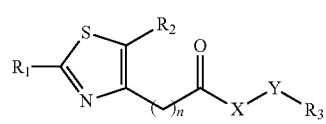

13 Claims, 1 Drawing Sheet

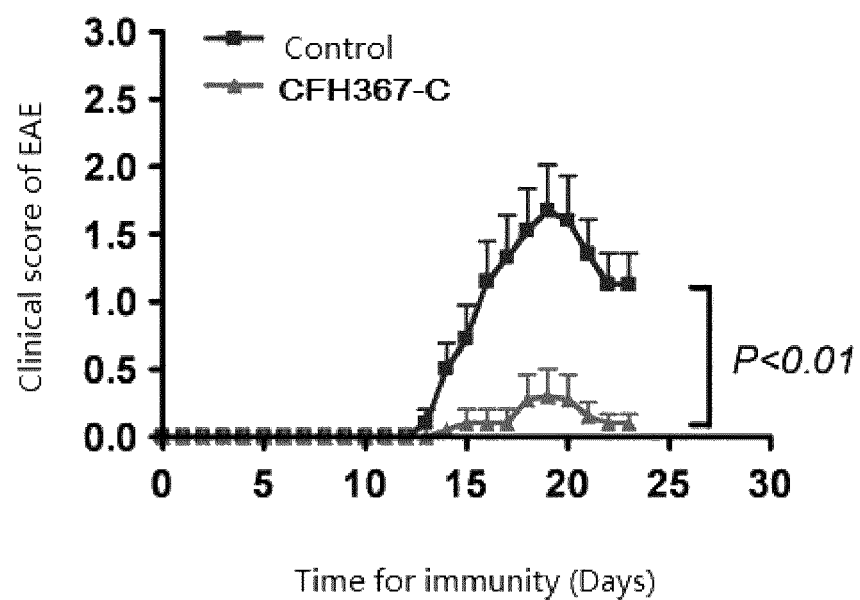

THIAZOLE COMPOUNDS, METHODS FOR PREPARATION AND USE THEREOF

FIELD OF TECHNOLOGY

The present invention relates to a class of compounds of thiazoles, the method for their preparation and use thereof. More specifically, the present invention relates to novel derivatives of the natural product largazole, the method for preparing them and their uses for treatments against tumor and multiple sclerosis as inhibitors of histone deacetylase (HDAC).

BACKGROUND ART

Tumor is the second largest disease after the cardiovascular disease worldwide and the tumor incidence rate is still rising in recent years. The treatment of cancer has always been a problem troubling human beings. Because of the lack of selectivity of targets, traditional chemotherapy drugs tend to produce more serious toxic side effects. This situation requires people to develop antitumor drugs of specific molecular targets with high efficiency and low toxicity. It has become an important direction of research and development of antitumor drugs nowadays to use a key enzyme of cell signal transduction pathway related to tumor cell differentiation, proliferation and metastasis as a target of drug screening, and find new anticancer medicine selectively acting on this specific target with high efficiency, low toxicity and high specificity. Histone deacetylase (HDAC) is such a key enzyme.

Multiple Sclerosis (MS) is a typical kind of typical autoimmune disease diseases. The pathology of MS disease includes acute inflammation of the central nervous system and demyelination, which is one of the most important causes leading to noninvasive paralysis of the nervous system and disability among young people. The clinical manifestation of MS is heterogeneous. More than 80% of the patients are manifested as relieved relapse phenotype. Since pathogenesis of the disease is unknown and sensitive diagnostic signs are still lacking at present, the diagnosis of MS still only depends on multiple characteristic of the disease in time and space. In addition, a lot of other diseases such as ophthalmoneuromyelitis have symptoms extremely similar to MS. Therefore, for MS treatment even the diagnosis remains very difficult at present.

The current findings indicate that $CD4^+$ T cells play an important role in the pathogenesis of MS, at least initiating MS at an early stage. Previous studies suggest that $T_H1$ cell (characterized in producing IFN-γ) plays an important role in the occurrence of the diseases. With the discovery of $T_H17$, more and more evidence shows that the function of latter in the pathogenesis of MS is not inferior than that of $T_H1$, for example, the mice with less quantity of $T_H17$ cells were not susceptible to EAE (Experimental Autoimmune Encephalomyelitis), $T_H17$ cells were identified in the brain tissue of the MS patients, etc.

Chromatin histone acetylation and deacetylation are critical processes regulating gene expressions, while abnormal gene expression is the molecular biological basis of the occurrence of tumor and some genetic and metabolic diseases. The degree of acetylation of histones is coordinativly controlled by histone acetyltransferase (HAT) and histone deacetylase (HDAC). When HDAC is over expressed and then recruited by a transcription factor, it will lead to the abnormal inhibition of specific genes, thus resulting in the occurrence of tumors and other diseases.

HDACs have eighteen subtypes, which can be divided into four classes, namely class I (HDAC1,2,3,8), class II (HDAC1,2,3,8), class III (SIRT1~7) and class IV (HDAC11) respectively. (Johnstone, R. W. 2002 *Nature Rev. Drug Disc.* 1:287). It is reported that activity of HDAC is relevant to the occurrence of cancer (Archer, S. Y. etc. 1998 *Proc. Nat. Acad. Sci. USA,* 95: 6791-6796). When HDAC is over expressed, it will inhibit in vivo gene expression of natural tumor-inhibiting factors such as p53 (Gu, W. etc. 1997 *Cell,* 90: 595-606). However, inhibitors of HDAC (HDACi) enhance chromatin histone acetylation level, thus resulting in activation of expression of specific genes, accordingly resulting in differentiation of cells or apoptosis of cancer cells. Clinical studies show that the high level of acetylation of histones can be achieved by inhibiting the activity of HDAC.

The HDAC that have already been discovered at present can be divided into the following categories on the basis of structure: short-chain fatty acids; hydroxamic acids; electrophilic epoxy-ketons group; o-phenylenediamines and macrocyclic peptides (Miller, T. A. etc. 2003 *J. Med. Chem.* 46:5097; Rosato, R. R. etc. 2004 *Expert. Opin. Invest. Drugs* 13:21; Monneret, C., 2005 *Eur. J. Med.* 40:1; Yoo, C. B., etc. 2006 *Nat. Rev. Drug Discovery* 5:37). The HDACi structure-activity relationship studies have shown that most HDACis can be segmented into surface recognition structural domain, zinc chelating region (ZBG) and hydrophobic aliphatic chain connecting the former two parts (Marks, P. 2007 *Oncogene* 26:1351).

Histone deacetylase (HDAC) is an important protein for epigenetic regulation, which regulates chromatin remodeling, gene expression and functions of various proteins including transcription factors, histones, cytoskeletal proteins, etc. HDAC are a class of small molecule compounds that can block the activity of HDAC and lead to cell cycle arrest, cell differentiation and apoptosis, which is the reason why they have been applied in tumor therapy. Recent experimental results show that HDAC may also have anti-inflammatory and immunemodulatory effects. Camelo et al. found that in the mice model of MS (Experimental autoimmune encephalomyelitis, EAE) HDACi TSA can effectively inhibit T cell invasion to the central nervous system of mice, thereby reducing the clinical symptoms of the disease. Chung et al. found that, the HDAC is phenyl butyric acid and TSA can inhibit expression of TNF-alpha in animal arthritis models and reduce the infiltration of mononuclear cells, thereby reducing the symptoms of the disease. Studies carried out by Bosisio et al. proved that HDACi can inhibit the antigen-presenting dendritic cell from secreting cytokines in favor of producing $T_H1$ and $T_H17$, which includes IL-12, IL-23 etc. Studies carried out by Tao et al. showed that HDACi can enhance the differentiation of the suppressive Treg cell and inhibitory function on $T_H1$ and $T_H17$ cells. The above-mentioned studies showed that the inhibition of HDAC is closely related to the occurrence and development of autoimmune diseases. HDACi with lower toxicity, better selectivity will contribute to the treatment of autoimmune diseases, especially to the treatment of MS diseases.

Largazole is a highly functionalized sixteen-membered cyclic peptide lactone isolated from the Florida marine cyanobacteria *Symploa* sp. (Taori, K., etc. 2008 *J. Am. Chem. Soc.* 130:1806-1807; Ying, Y. et al. 2008 *J. Am. Chem. Soc.* 130:8455-8459), and its structure is shown as follows. Largazole has a novel skeleton structure, which includes: the tandem motif of dihydro-thiazole ring substituted by 4-methyl and thiazole ring, L-valine and (3S,4E)-3-hydroxy-7-sulfydryl-4-heptenoic acid. Pharmacological experiments show that largazole is able to selectively inhibit the growth of breast cancer cells (MDA-MB-231) and fibroblast osteosarcoma cells (U2OS), while showing less effect on normal mammary epithelial cells (NMuMG) and normal fibroblasts (NIH3T3). Later studies showed that largazole is able to selectively inhibit class I HDAC. Based on those knowledge of largazole, the inventors optimized and modified the structure of largazole, and evaluated their activities, thereby obtaining a series of compounds with potential for further development.

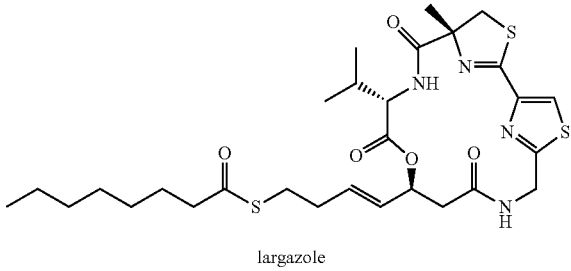 [SMILES: CCCCCCCC(=O)SCC/C=C/[C@@H]1CC(=O)NCc2nc(cs2)C2=N[C@@](C)(CS2)C(=O)N[C@@H](C(C)C)C(=O)O1]

largazole

SUMMARY OF THE INVENTION

One object of the present invention is to design and synthesize a novel class of thiazole compounds, which can be used as histone deacetylase inhibitors, thus providing new ways for discovery of new drugs against tumor and multiple sclerosis.

Another object of the present invention is to provide methods for preparing of the thiazole compounds.

Another object of the present invention is to provide for the use of the thiazole compounds.

The thiazole compounds of present invention have the structure of general formula I:

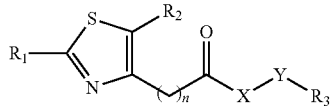

I wherein,
$R_1$ is one of $R_{1a}$, $R_{1b}$ or $R_{1c}$:

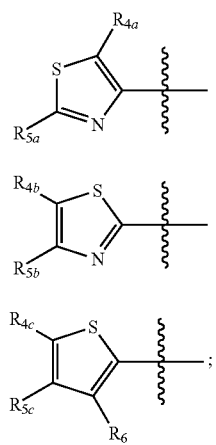

$R_{1a}$ $R_{1b}$ $R_{1c}$

In which,
$R_{4a}$ and $R_{5a}$ are in each occurrence independently one of: $C_1$-$C_6$ alkyl, tert-butoxycarbonylamino, hydrogen, halogen, hydroxyl, nitro, $C_3$-$C_6$ cycloalkyl, $C_1$-$C_6$ alkoxyl; where the $C_1$-$C_6$ alkoxyl can be substituted with $C_6$-$C_{10}$ aryl, amino, $C_1$-$C_6$ alkylamino; where the $C_1$-$C_6$ alkylamino can be substituted with $C_6$-$C_{10}$ aryl, or $C_1$-$C_6$ alkyl; where the $C_1$-$C_6$ alkyl can be substituted with hydroxyl, $C_1$-$C_4$ alkoxyl, fluoro, $C_6$-$C_{10}$ aryl, or $C_2$-$C_6$ alkenyl; where the $C_2$-$C_6$ alkenyl can be substituted with hydroxyl, $C_1$-$C_4$ alkoxyl, fluoro, $C_6$-$C_{10}$ aryl, or $C_2$-$C_6$ alkynyl; where the $C_2$-$C_6$ alkynyl can be substituted with hydroxyl, $C_1$-$C_4$ alkoxyl, fluoro, $C_6$-$C_{10}$ aryl, or 5 to 7-membered aromatic heterocycle containing 1-3 heteroatoms selected from N, O and S;

$R_{4b}$ and $R_{5b}$ are in each occurrence independently one of: hydrogen, halogen, hydroxyl, nitro, $C_3$-$C_6$ cycloalkyl, $C_1$-$C_6$ alkoxyl; where the $C_1$-$C_6$ alkoxyl can be substituted with $C_6$-$C_{10}$ aryl, amino, $C_1$-$C_6$ alkylamino; where the $C_1$-$C_6$ alkylamino can be substituted with $C_6$-$C_{10}$ aryl, or $C_1$-$C_6$ alkyl; where the $C_1$-$C_6$ alkyl can be substituted with hydroxyl, $C_1$-$C_4$ alkoxyl, fluoro, $C_6$-$C_{10}$ aryl, or $C_2$-$C_6$ alkenyl; where the $C_2$-$C_6$ alkenyl can be substituted with hydroxyl, $C_1$-$C_4$ alkoxyl, fluoro, $C_6$-$C_{10}$ aryl, or $C_2$-$C_6$ alkynyl; where the $C_2$-$C_6$ alkynyl can be substituted with hydroxyl, $C_1$-$C_4$ alkoxyl, fluoro, $C_6$-$C_{10}$ aryl, or 5 to 7-membered aromatic heterocycle containing 1-3 heteroatoms selected from N, O and S; or, $R_{4b}$ and $R_{5b}$ together with a carbon atom to which $R_{4b}$ and $R_{5b}$ are both attached form a 3 to 10-membered cyclic hydrocarbon, or a 3 to 10-membered heterocycle containing 1 to 3 heteroatoms selected from N, O and S;

$R_{4c}$, $R_{5c}$ and $R_6$ are in each occurrence independently one of: hydrogen, halogen, hydroxyl, nitro, $C_3$-$C_6$ cycloalkyl, $C_1$-$C_6$ alkoxyl; where the $C_1$-$C_6$ alkoxyl can be substituted with $C_6$-$C_{10}$ aryl, amino, $C_1$-$C_6$ alkylamino; where the $C_1$-$C_6$ alkylamino can be substituted with $C_6$-$C_{10}$ aryl, or $C_1$-$C_6$ alkyl; where the $C_1$-$C_6$ alkyl can be substituted with hydroxyl, $C_1$-$C_4$ alkoxyl, fluoro, $C_6$-$C_{10}$ aryl, or $C_2$-$C_6$ alkenyl; where the $C_2$-$C_6$ alkenyl can be substituted with hydroxyl, $C_1$-$C_4$ alkoxyl, fluoro, $C_6$-$C_{10}$ aryl, or $C_2$-$C_6$ alkynyl; where the $C_2$-$C_6$ alkynyl can be substituted with hydroxyl, $C_1$-$C_4$ alkoxyl, fluoro, $C_6$-$C_{10}$ aryl, or 5 to 7-membered aromatic heterocycle containing 1-3 heteroatoms selected from N, O and S;

$R_2$ is hydrogen, halogen, hydroxyl, $C_1$-$C_6$ alkoxyl, $C_1$-$C_8$ alkoxyl which can be substituted with $C_6$-$C_{10}$ aryl, amino, or $C_1$-$C_6$ alkylamino, where the $C_1$-$C_6$ alkylamino can be substituted with $C_6$-$C_{10}$ aryl, $C_1$-$C_6$ alkyl, or $C_3$-$C_6$ cycloalkyl; where the $C_3$-$C_6$ cycloalkyl can be substituted with $C_1$-$C_6$ alkyl; where the $C_1$-$C_6$ alkyl that can be substituted by one or more substituent groups independently selected from hydroxyl, $C_1$-$C_4$ alkoxyl, halogen, benzyloxyl, $C_6$-$C_{10}$ aryl, or $C_2$-$C_5$ alkenyl; where the $C_2$-$C_6$ alkenyl group can be substituted by one or more substituent groups independently selected from hydroxyl, $C_1$-$C_4$ alkoxyl, halogen and $C_6$-$C_{10}$ aryl, or $C_2$-$C_6$ alkynyl, where the $C_2$-$C_5$ alkynyl that can be substituted by one or more substituent groups independently selected from hydroxyl, $C_1$-$C_4$ alkoxyl, halogen, and $C_6$-$C_{10}$ aryl; where the $C_6$-$C_{10}$ aryl can be substituted by halogen or nitro, or 5-7 membered aromatic heterocycle containing 1 to 3 heteroatoms selected from N, O and S;

n is 0, 1 or 2;
X is —N($R_7$)— or

wherein $R_7$ is hydrogen or $C_1$-$C_6$ alkyl;
conditional component Y is one of: —($C_1$-$C_{10}$ alkyl)-, —($C_2$-$C_9$ alkenyl)-, —($C_6$-$C_{10}$ aryl)-, —($C_1$-$C_6$ alkyl)-($C_6$-$C_{10}$ aryl)-, —($C_6$-$C_{10}$ aryl)-($C_2$-$C_6$ alkenyl)-, —($C_3$-$C_6$ cycloalkyl)-, —($C_1$-$C_5$ alkyl)-C(O)—NH—($C_1$-$C_5$ alkyl)-, —($C_1$-$C_5$ alkyl)-C(O)—O—($C_1$-$C_5$ alkyl)- or —($C_1$-$C_5$ alkyl)-C(O)—O—($C_2$-$C_9$ alkenyl)-;

$R_3$ is one of $R_{3a}$, $R_{3b}$, $R_{3c}$, $R_{3d}$ or $R_{3e}$:

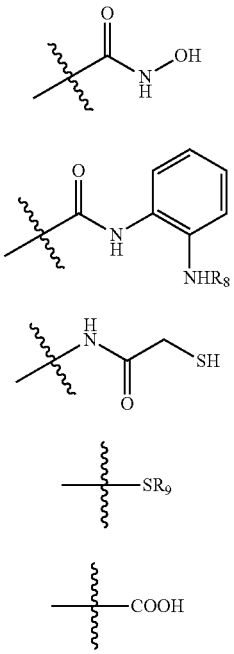

$R_8$ is hydrogen or $C_1$-$C_6$ alkylcarbonyl; Preferably, $R_8$ is hydrogen;

$R_9$ is hydrogen or $C_1$-$C_{10}$ alkylcarbonyl.

In a further embodiment of present invention, wherein,

In the general formula I:
wherein:
$R_1$ is $R_{1a}$;
n=0;
$R_2$, X, Y and $R_3$ are defined as above.
specifically as the following general formula $II_a$:

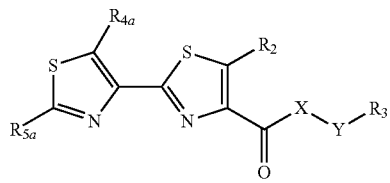

In the general formula $II_a$:

$R_{4a}$ and $R_{5a}$ are defined as above; Preferably, $R_{4a}$ and $R_{5a}$ each independently are hydrogen, $C_1$-$C_6$ alkyl; where the $C_1$-$C_6$ alkyl can be substituted with tert-butoxycarbonylamino.

In another further embodiment of present invention, wherein,

In the general formula I:
wherein:
$R_1$ is $R_{1b}$;
n=0;
$R_2$, X, Y and $R_3$ are defined as above, specifically as the following general formula $II_b$:

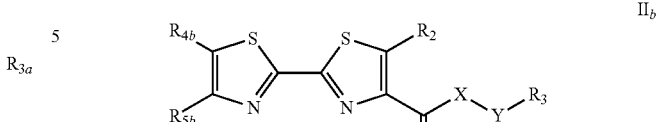

In the formula $II_b$:

$R_{4b}$ and $R_{5b}$ are defined as above; Preferably, $R_{4b}$ and $R_{5b}$ each independently are hydrogen, C1-C6 alkyl, C3-C6 cycloalkyl or C6-C10 aryl; or, $R_{4b}$ and $R_{5b}$ together with the carbon atom to which they are attached form a 3 to 10-membered cyclic hydrocarbon.

In another further embodiment of present invention, wherein,

In the general formula I:
wherein
$R_1$ is $R_{1c}$;
n=0;
$R_2$, X, Y and $R_3$ are defined as above,
specifically as the following general formula $II_c$:

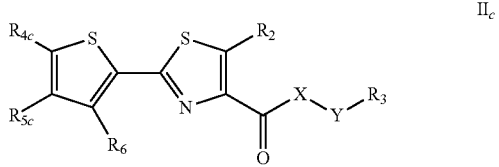

In the formula $II_c$:

$R_{4c}$, $R_{5c}$ and $R_6$ are defined as above;

Preferably, $R_{4c}$, $R_{5c}$ and $R_6$ each independently are hydrogen or $C_1$-$C_6$ alkyl.

In a more preferable embodiment of present invention, the X is —NH, n=0 and $R_2$, $R_3$, $R_{4b}$, $R_{5b}$ and Y are defined as above, the compound of present invention has the following structure of general formula III:

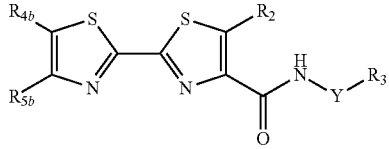

In a particularly preferable embodiment of present invention, the X is —NH, and n=0, while $R_3$ is $R_{1a}$, the compound of present invention has the following structure of general formula IV:

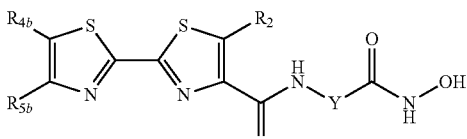

Wherein, $R_2$, $R_3$, $R_{4b}$, $R_{5b}$ and Y are defined as above.

$R_2$ is one of: hydrogen, $C_1$-$C_6$ alkyl; where the $C_1$-$C_6$ alkyl can be substituted with hydroxyl, $C_6$-$C_{10}$ aryl or benzyloxyl, or $C_3$-$C_6$ cycloalkyl; where the $C_3$-$C_6$ cycloalkyl that can be substituted with $C_1$-$C_6$ alkyl or $C_6$-$C_{10}$ aryl; where the $C_2$-$C_5$ alkenyl that can be substituted with hydroxyl, $C_6$-$C_{10}$ aryl, or $C_2$-$C_5$ alkoxyl; where the $C_2$-$C_5$ alkoxyl can be substituted with $C_6$-$C_{10}$ aryl; where the $C_6$-$C_{10}$ aryl can be substituted with halogen, or nitro;

$R_{4b}$ and $R_{5b}$ are each independently one of: hydrogen, fluoro, or $C_1$-$C_6$ alkyl; where the $C_1$-$C_6$ alkyl can be substituted with hydroxyl, fluoro, $C_3$-$C_6$ cycloalkyl, or $C_2$-$C_6$ alkenyl where the $C_2$-$C_6$ alkenyl can be substituted with hydroxyl, fluoro, or $C_6$-$C_{10}$ aryl; or, $R_{4b}$ and $R_{5b}$ together with the carbon atom to which the $R_{4b}$ and $R_{5b}$ are attached to form a 3 to 10-membered cyclic hydrocarbon, or a 3 to 10-membered heterocycle containing 1 to 3 heteroatoms selected from N, O and S; and Y is —($C_1$-$C_8$ alkyl)-, —($C_6$-$C_{10}$ aryl)-, —($C_1$-$C_6$ alkyl)-($C_6$-$C_{10}$ aryl), or —($C_6$-$C_{10}$ aryl)-($C_2$-$C_6$ alkenyl)-.

The thiazole compounds of general formula I of the present invention specifically are as follows:

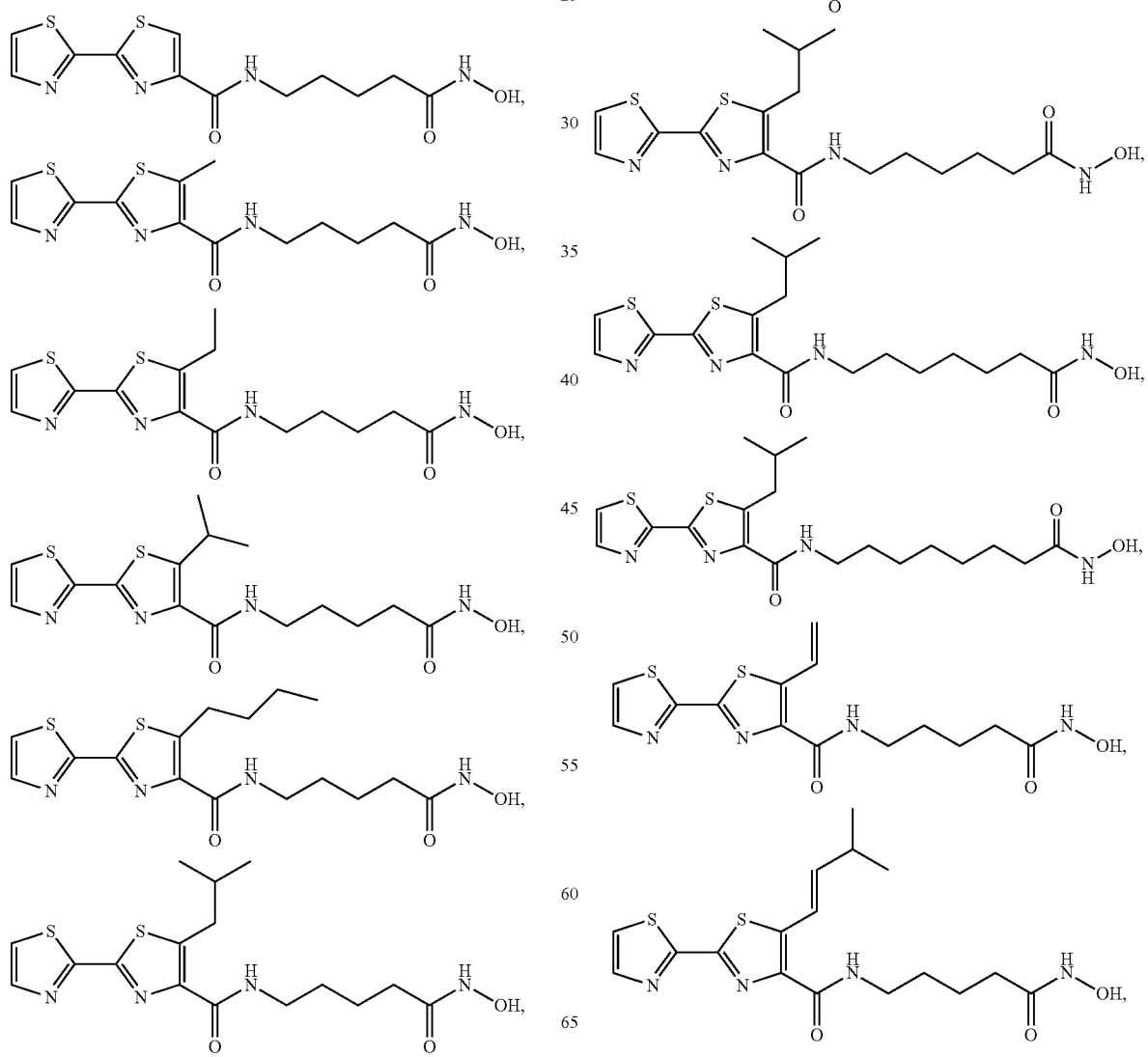

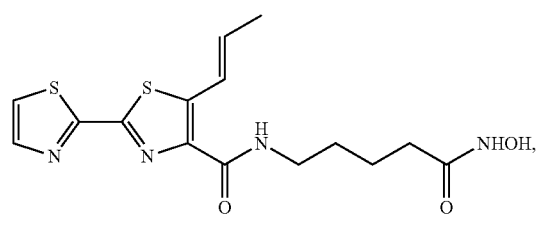
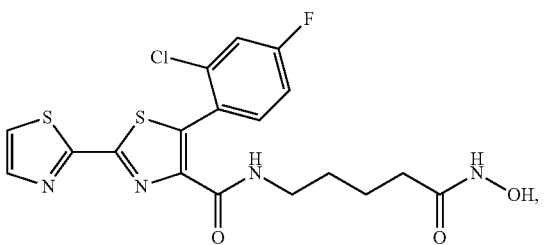
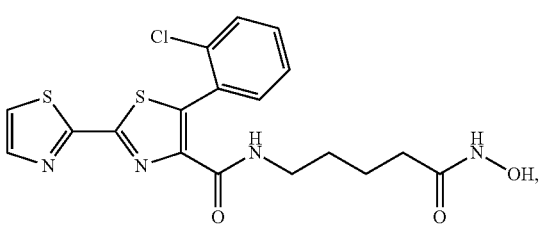
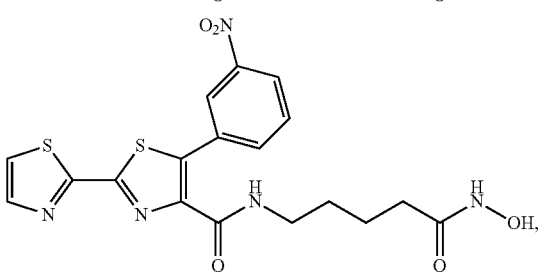
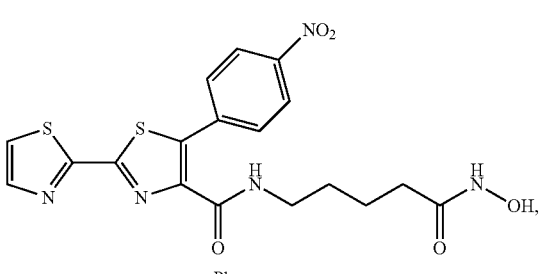
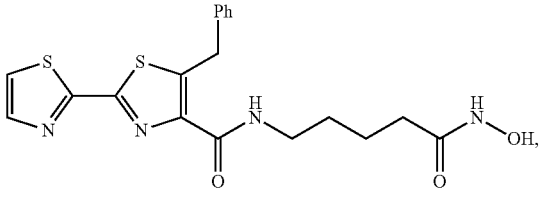
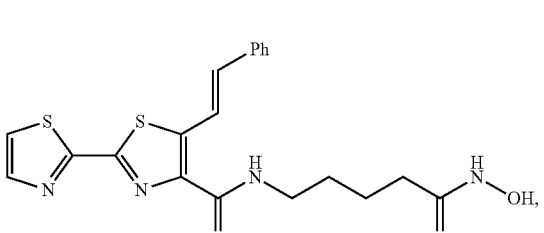
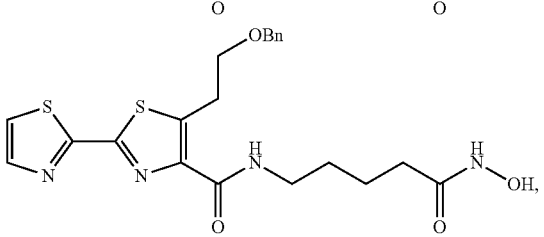

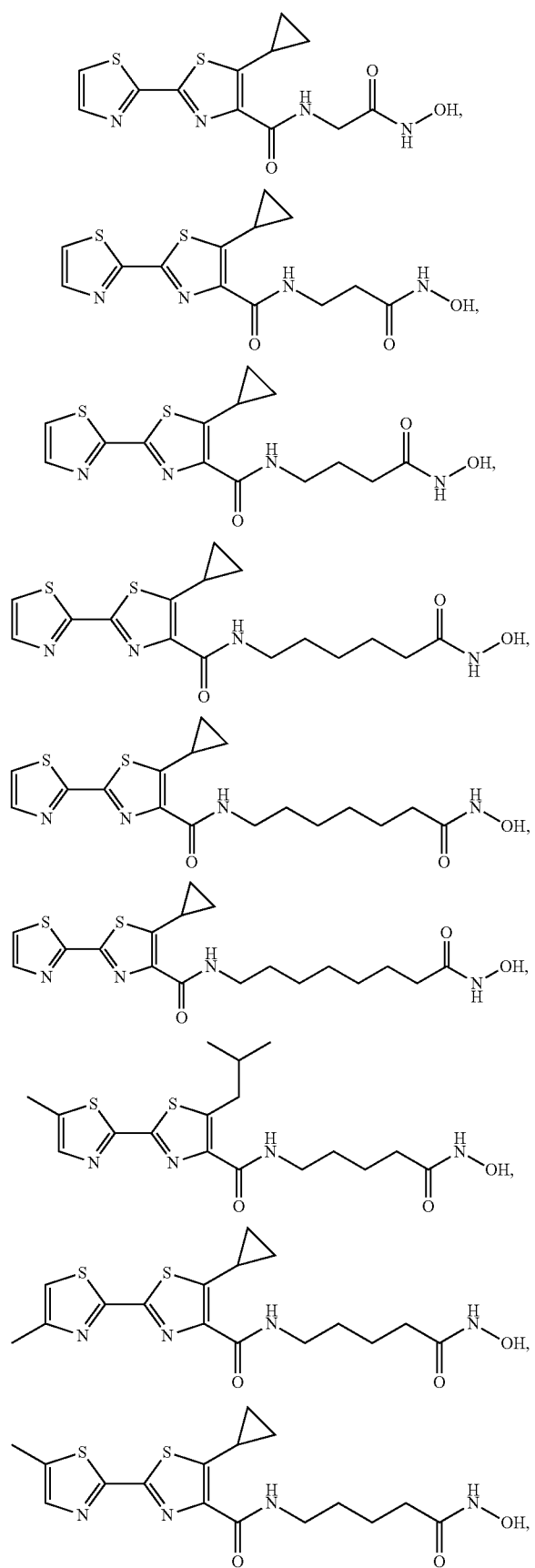
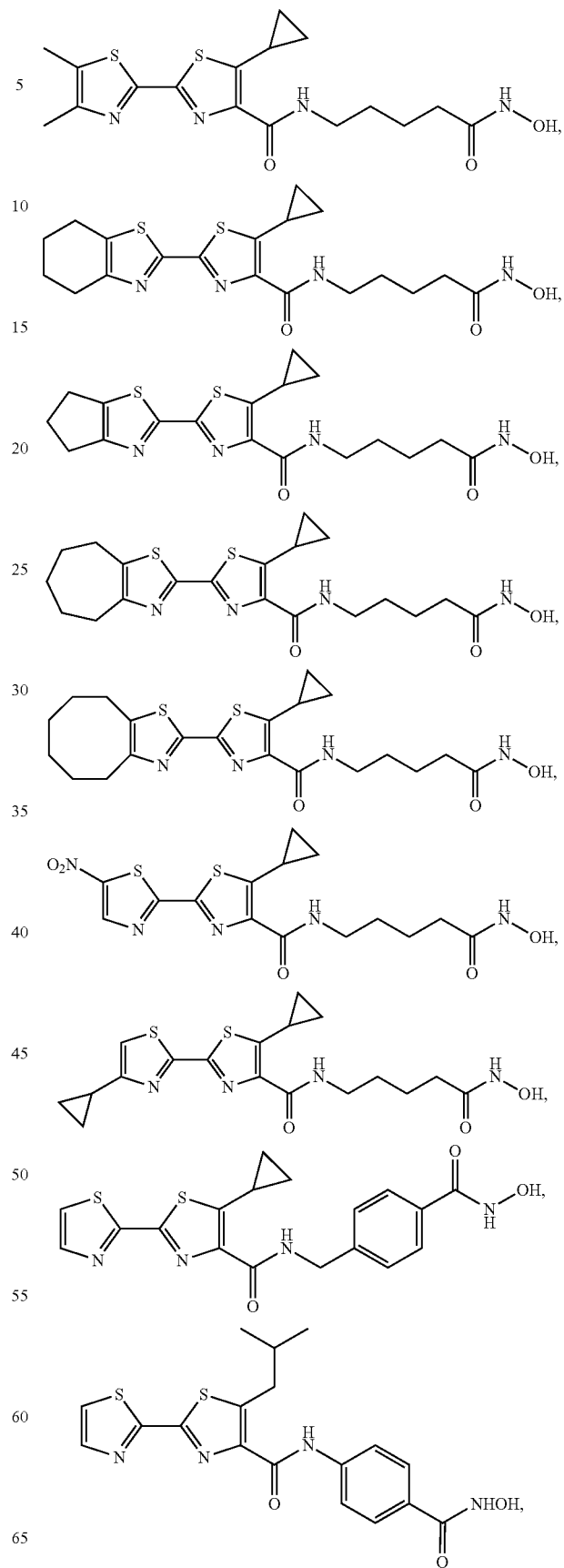

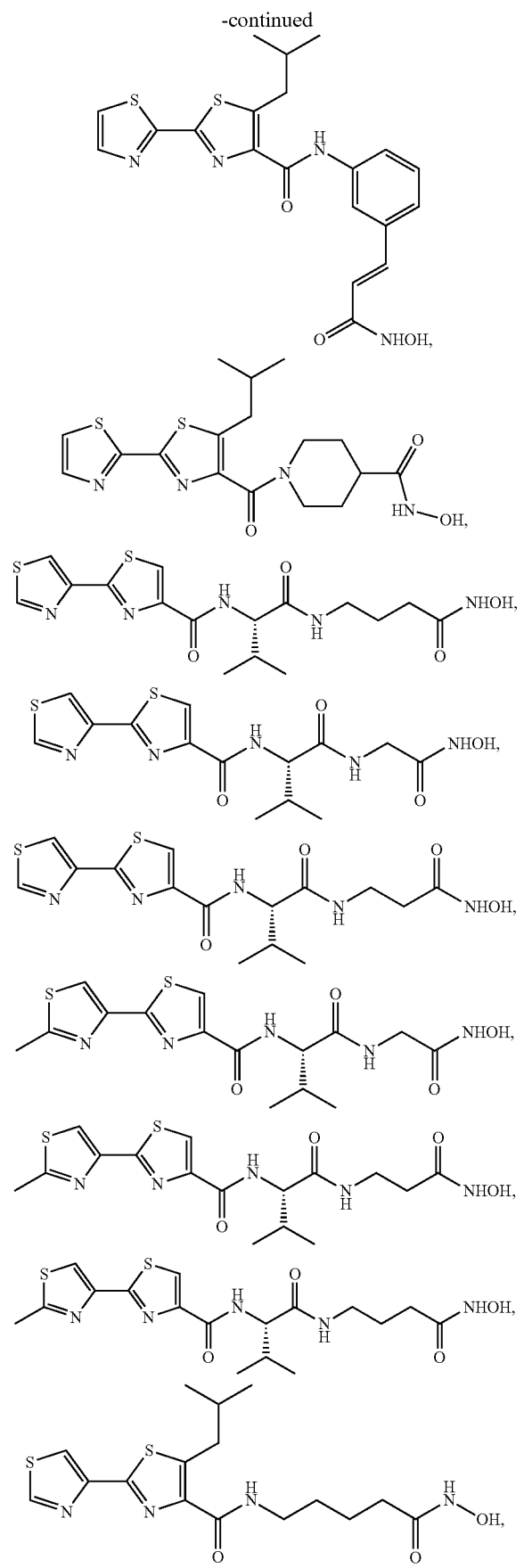
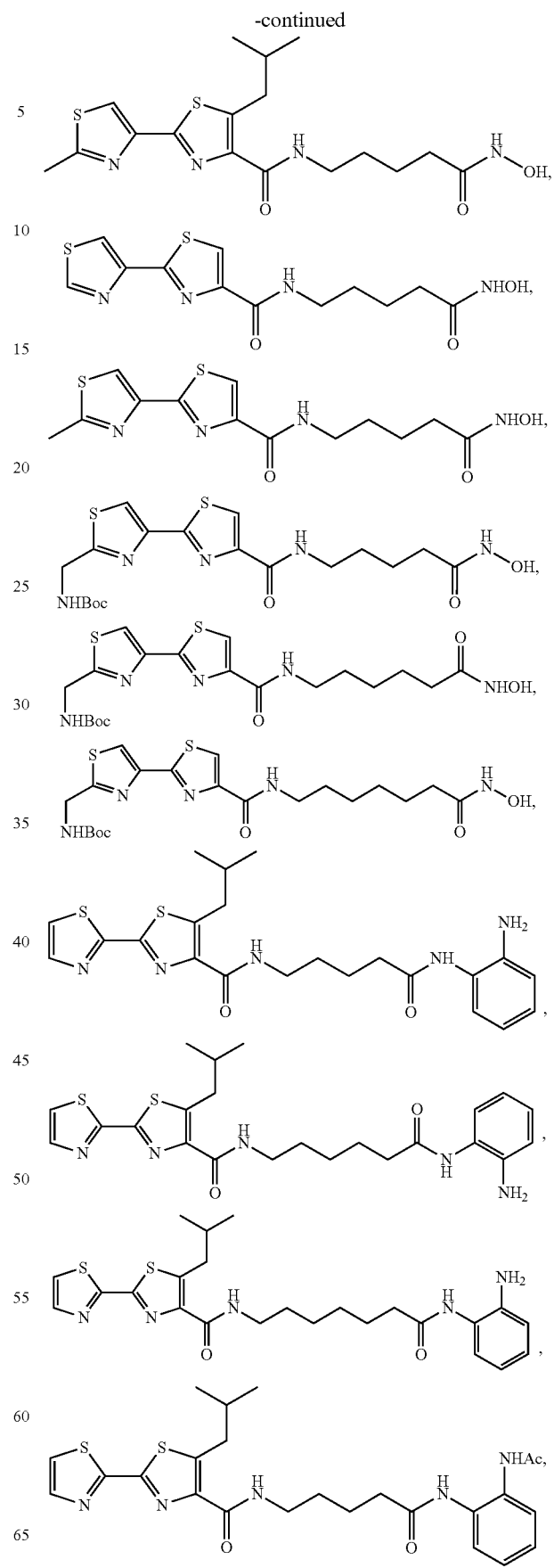

15
-continued
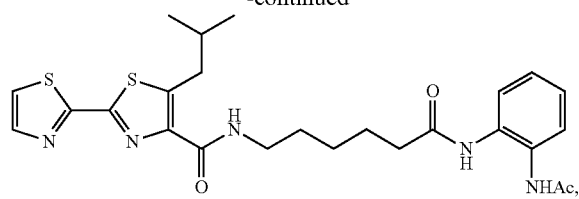
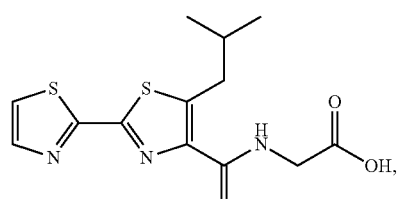
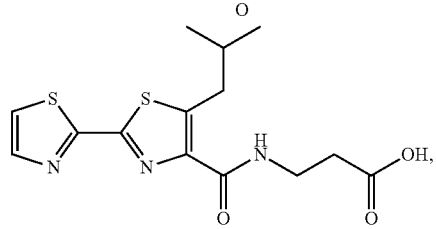
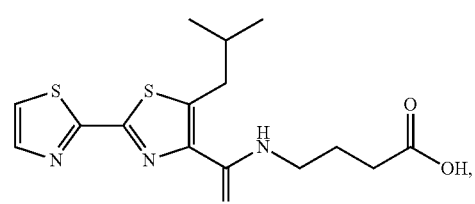
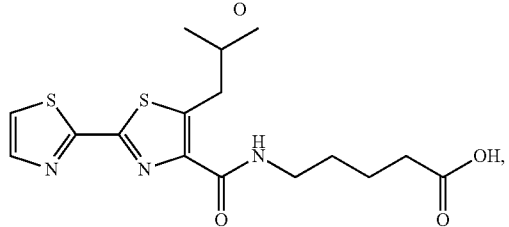
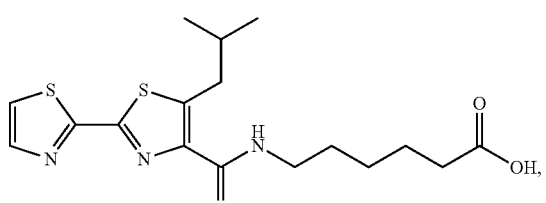
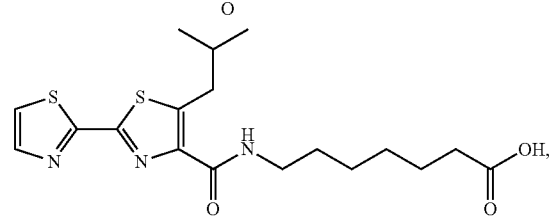
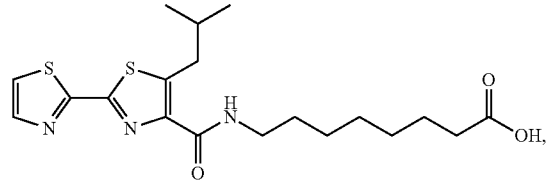
16
-continued
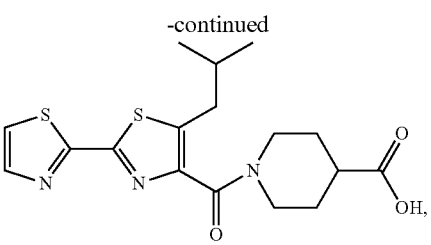
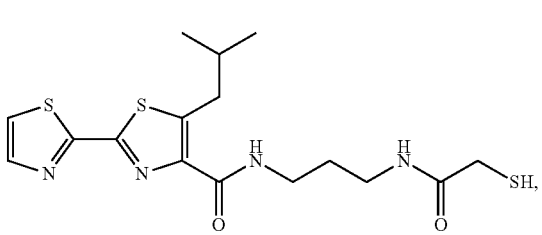 [SMILES: CC(C)Cc1sc(-c2nccs2)nc1C(=O)NCCCCC(=O)NO]
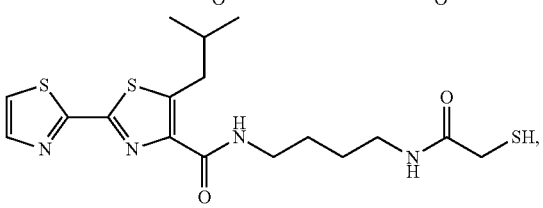
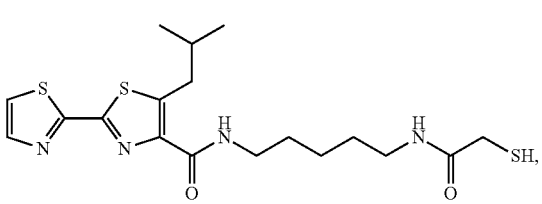
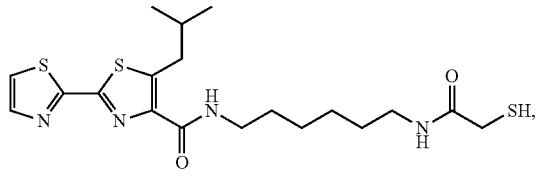
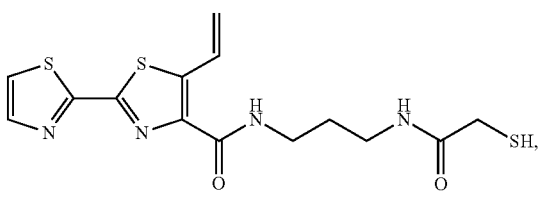 [SMILES: C=Cc1sc(-c2nccs2)nc1C(=O)NCCCCC(=O)NO]
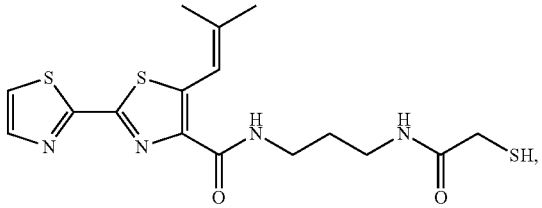 [SMILES: CC(C)=Cc1sc(-c2nccs2)nc1C(=O)NCCCNC(=O)CS]
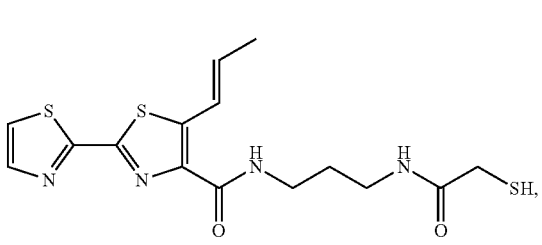 [SMILES: C/C=C/c1sc(-c2nccs2)nc1C(=O)NCCCNC(=O)CS]

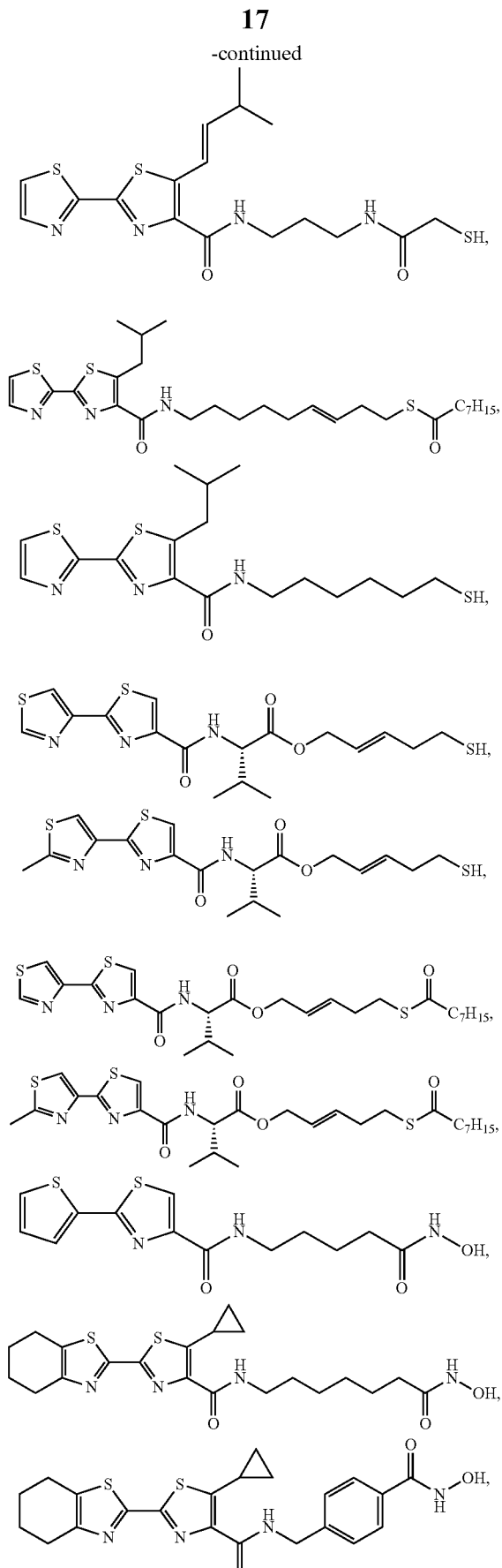
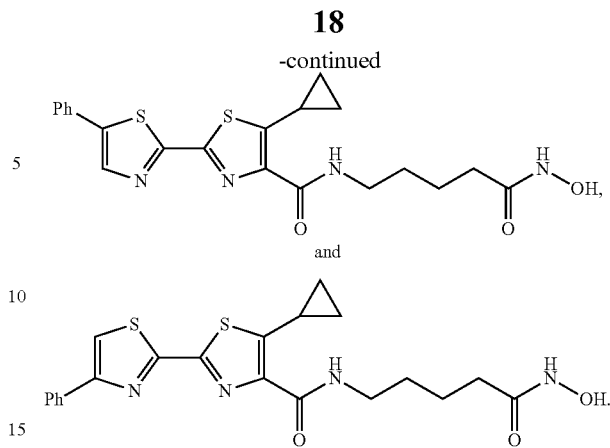
Moreover the present invention provides methods for preparing the thiazole compound of general formula I, wherein, the method can be employed by one of the following Route one to five;
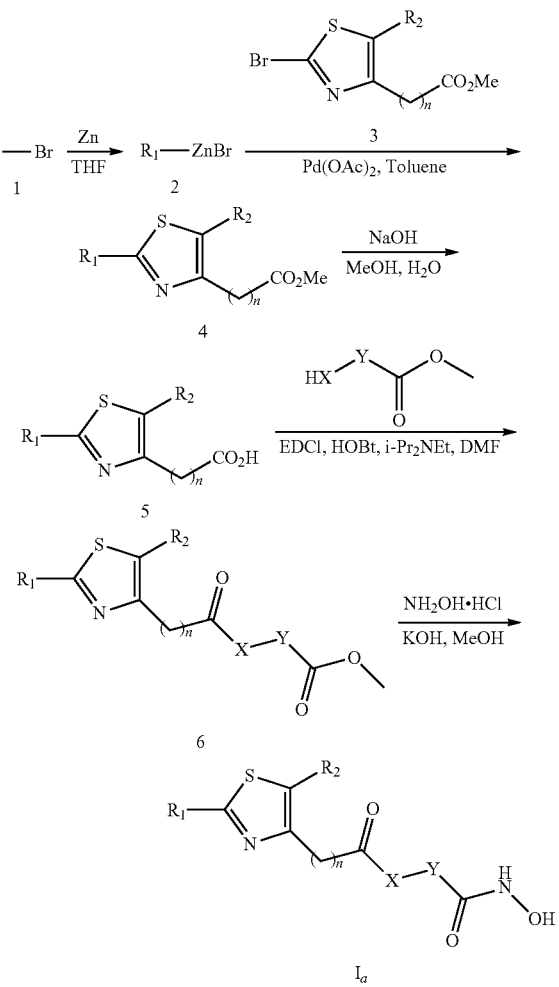
In Route One:
$R_1$, $R_2$, n, X and Y each have the same meaning as above;
Specifically, compound 1 reacts with active zinc powder in THF to form zinc reagent compound 2; Negishi coupling reaction of compound 2 with 2-bromo-thiazole compound catalyzed by palladium acetate and triphenylphosphine in toluene affords compound 4. Hydrolysis of compound 4 in sodium hydroxide/methanol-water produces compound 5 which is the corresponding acid of compound 4; Condensation reaction of compound 5 with various nucleophilic reagents of the formula HX—Y—COOMe is conducted using condensing agents such as EDCI, HOBt and i-Pr$_2$NEt in DMF to obtain compound 6; Compound 6 reacts with the freshly-made methanol solution of hydroxy amine to produce the compound $I_a$;

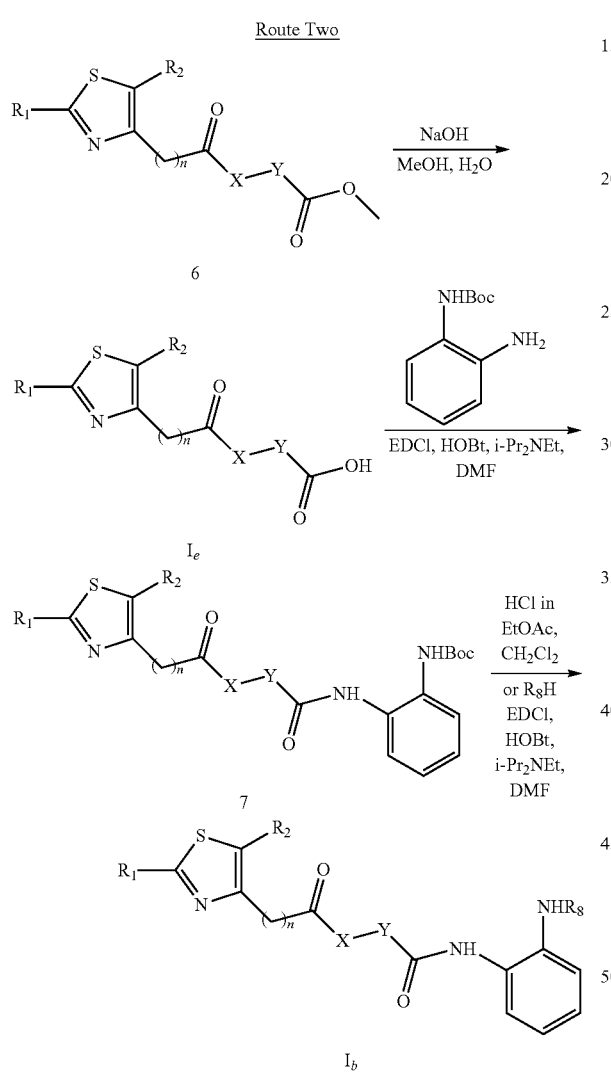

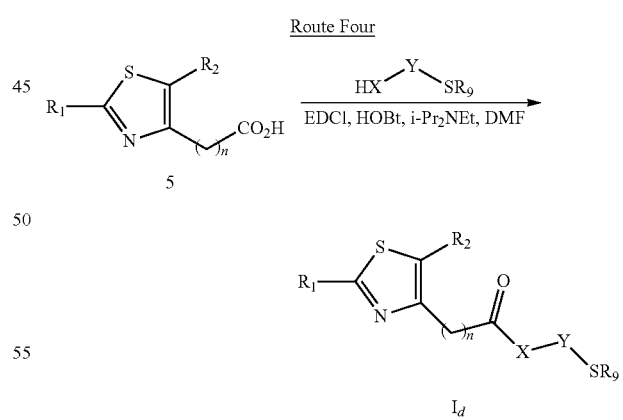

In Route Two:

R$_1$, R$_2$, R$_8$, n, X and Y each have the same meaning as above;

Specifically, compound 6 is hydrolyzed by alkali in methanol or THF/water to obtain Compound $I_e$; Condensation reaction of compound $I_e$ with mono-Boc-protected o-phenylenediamine is conducted using condensing agents such as EDCI, HOBt and i-Pr$_2$NEt in DMF to obtain compound 7; Boc protecting group of compound 7 is removed in hydrochloric acid ethyl acetate solution to obtain said compounds $I_b$, or compound 7 reacts with various nucleophile of formula R$_8$H to obtain said compound $I_b$;

In Route Three:

R$_1$, R$_2$, n, X and Y each have the same meaning as above;

Specifically, condensation reaction of compound 5 with various nucleophile of the formula HX—Y—NHCOCH$_2$STrt is conducted using condensing agents such as EDCI and DMAP as base in dichloromethane to obtain compound 8; Boc protecting group of compound 8 is removed by the trifluoroacetic acid to obtain the compound $I_c$;

In Route Four:

R$_1$, R$_2$, R$_9$, n, X and Y each have the same meaning as above;

Specifically, condensation reaction of compound 5 with various nucleophile of the formula HX—Y—SR$_9$ is conducted using condensing agents such as EDCI, HOBt and i-Pr$_2$NEt in DMF to obtain the compound $I_d$;

Route Five

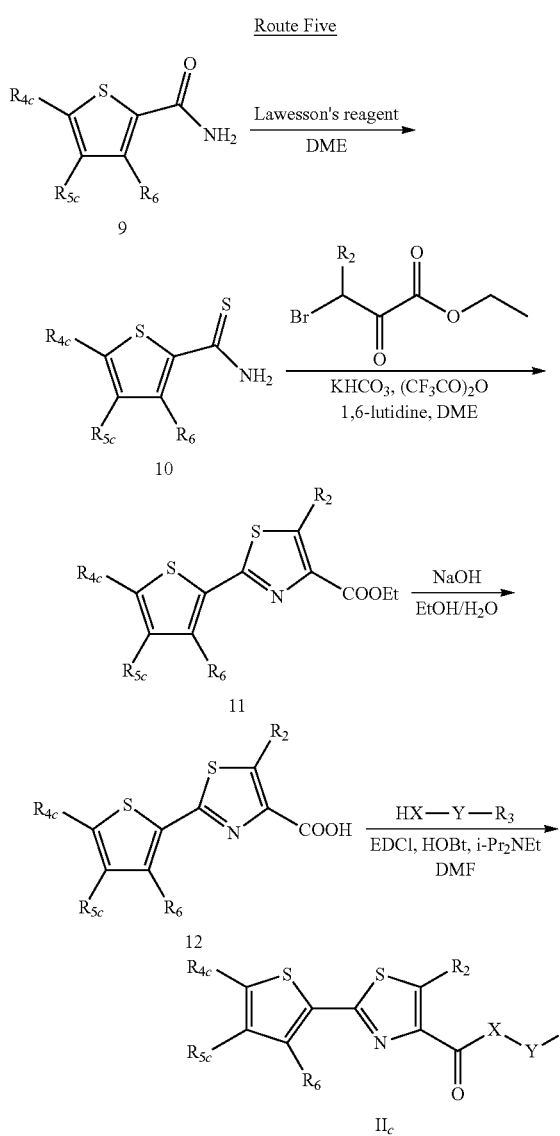

In Route Five:

$R_2$, $R_3$, $R_{4c}$, $R_{5c}$, $R_6$, n, X and Y each have the same meaning as above;

Specifically, reaction of compound 9 with Lawesson's agent affords compound 10; Hantzsch reaction of compound 10 with ethyl bromopyruvate substituted by $R_2$ produces bisthiazole compound 11; Compound 11 is hydrolyzed by alkaline in methanol/water to afford compound 12; Condensation reaction of compound 12 with various nucleophile of the formula HX—Y—$R_3$ is conducted using condensing agents such as EDCI, HOBt and i-$Pr_2$NEt in DMF to obtain the compound $II_c$.

The thiazole compound of general formula I of present invention can be used for preparing the pharmaceuticals as histone deacetylase inhibitors, therefore, it can be used for preparing the pharmaceuticals against tumor and multiple sclerosis. The cell lines of the tumor include colon cancer cell HCT-116, pancreatic cancer cell Bx-PC3, leukemia cell HL60, human lung adenocarcinoma cell A549, breast cancer cell MDA-MB-231, and mammary epithelial cell HMEC.

Thus, it can be used for the treatment of colon cancer, pancreatic cancer, leukemia, lung cancer or breast cancer.

BRIEF DESCRIPTION OF THE DRAWINGS

FIG. 1 is the clinical score of EAE which was effectively alleviated by HDACi CFH367-C.

DETAILED DESCRIPTION OF THE PREFERRED EMBODIMENT

The present invention will hereinafter be further illustrated by the following examples, but not limited to such examples.

EXAMPLES FOR PREPARING COMPOUNDS

In the following embodiments of preparation, NMR will be determined by Mercury-Vx 300M instrument made by Varian, NMR calibration: δ H 7.26 ppm ($CDCl_3$), 2.50 ppm (DMSO-$d_6$), 3.15 ppm ($CD_3OD$); The reagents are mainly provided by Shanghai Chemical Reagent Company; Silica gel plates for TLC thin layer chromatography are produced by Shandong Yantai Huiyou silica gel Development Co. Ltd., Type HSGF 254; Silica gel for normal phase column chromatography used in purification of the compounds are produced by a branch of Shandong Tsingtao Marine Chemical Factory, Type zcx-11, 200-300 meshes.

Example 1 of Preparation

Compound Number CFH367-C

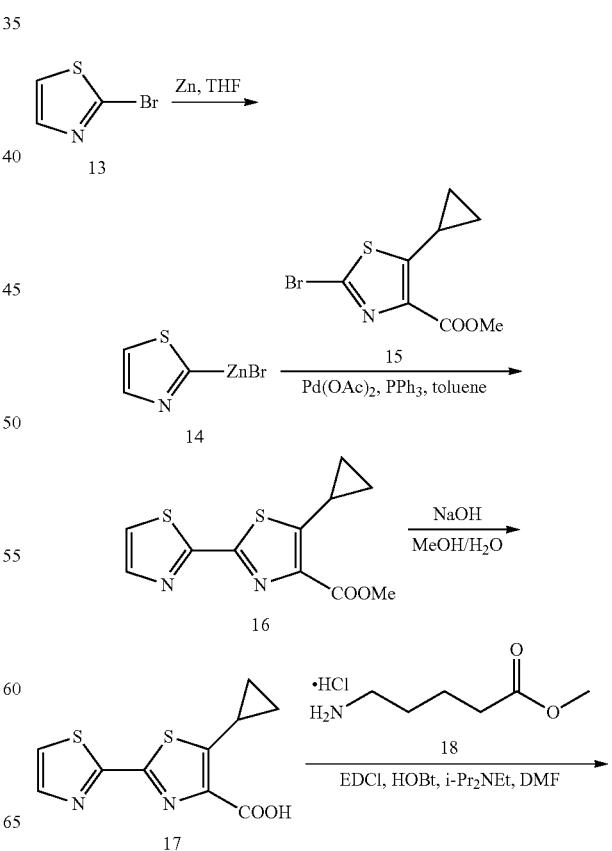

-continued

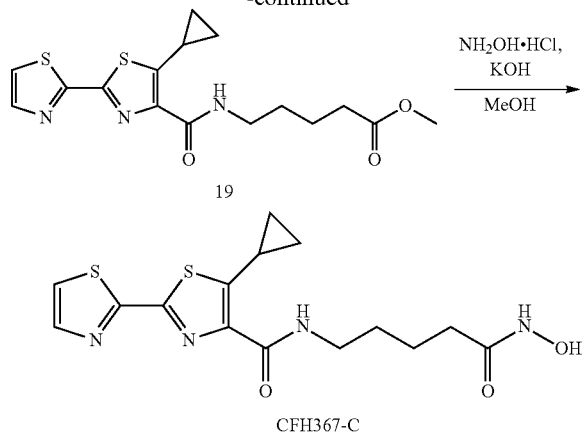

The active Zn powder (298 mg, 4.58 mmol) was dissolved in redistilled anhydrous THF (20 mL). The inner air was replaced by $N_2$. Compound 13 (875 mg, 5.34 mmol) was added dropwise, while the dropping speed was controlled to prevent from vigorous boiling. After such addition, the reaction mixture was refluxed for 1.5 h, and then was naturally cooled down to obtain zinc reagent 14.

Compound 15 (1 g, 3.82 mmol) was dissolved in anhydrous toluene (20 mL). The inner air was replaced by $N_2$. The above-described Zinc reagent 14 is introduced into the reaction mixture, then the catalyst palladium acetate (43 mg, 0.19 mmol) and triphenylphosphine (100 mg, 0.38 mmol) were added. The reaction mixture was heated to 80-90° C. for a while until the crude material compound 15 was all consumed. After removal of insoluble substance by filtration, the organic phase was concentrated and then diluted with $CH_2Cl_2$ (50 mL). After adding 1N HCl (30 mL) with stirring for 10 min, the organic phase was separated. The aqueous phase was extracted by $CH_2Cl_2$ (30 mL) twice. The combination of all extracted organic phases was concentrated and then subjected to silica gel column flash chromatography (PE/EtOAc=4:1) to obtain compound 16 (750 g, 73.5%, yellow grease), $^1$H NMR (300 MHz, CDCl$_3$) δ 7.85 (d, J=3.0 Hz, 1H), 7.45 (d, J=3.0 Hz, 1H), 3.96 (s, 3H), 3.10-3.14 (m, 1H), 1.31-1.38 (m, 2H), 0.84-0.89 (m, 2H).

Compound 16 (700 mg, 2.63 mmol) was dissolved in MeOH/$H_2O$ (30/6 mL), and then solid NaOH (210 mg, 5.26 mmol) was added in. The reaction mixture was heated to reflux for 1 h. After completion of reaction, the obtained mixture was concentrated under reduced pressure to remove most of MeOH and then diluted with $H_2O$. The aqueous phase was then acidified to pH=2 by 1N hydrochloric acid, extracted by EtOAc (20 mL×3 times), and washed with brine (30 mL). The organic phase was dried by anhydrous $Na_2SO_4$ and then concentrated to obtain a solid compound 17 (660 mg, 99.5%, pale yellow solid) which can be used directly in the next reaction.

Compound 17 (100 mg, 0.40 mmol) was dissolved in dry DMF (5 mL), then cooled to 0° C. in an ice-bath. EDCI (76 mg, 0.40 mmol) and HOBt (54 mg, 0.40 mmol) were added and stirred for 10 min at 0° C. Compound 18 (73 mg, 0.44 mmol) and i-Pr$_2$NEt (120 mg, 1.20 mmol) were added and stirred for 12 h at room temperature. The obtained mixture was diluted with 20 mL water, and then extracted by EtOAc (15 mL×3 times). The combined organic phases was washed by 1N hydrochloric acid (15 mL), saturated sodium bicarbonate solution (15 ml) and brine (20 mL) in sequence, and then dried by anhydrous $Na_2SO_4$. After removal of solvent by evaporating under a reduced pressure, the obtained residue was purified by silica gel column chromatography (PE/EtOAc=2:1) to obtain product compound 19 (104 mg, 71.7%, pale yellow grease). $^1$H NMR (300 MHz, CDCl$_3$) δ7.74 (d, J=3.0 Hz 1H), 7.42 (t, J=5.4 Hz, 1H), 7.36 (d, J=3.0 Hz 1H), 3.58 (s, 3H), 3.37 (q, J=6.3 Hz, 2H), 2.30 (t, J=6.6 Hz, 2H), 1.58-1.69 (m, 4H), 1.19-1.25 (m, 2H), 0.68-0.74 (m, 2H).

Hydroxylamine hydrochloride (197 mg, 2.8 mmol) was suspended in MeOH (15 mL), and then KOH (235 mg, 4.20 mmol) was added in and stirred for 5 min. The insoluble substance was removed by filtration and the filtrate was collected for use. After compound 19 (104 mg, 0.28 mmol) was dissolved in anhydrous MeOH (10 ml), freshly-prepared above-mentioned MeOH solution of hydroxylamine hydrochloride was added in and stirred for 1 h at room temperature. Reaction was monitored by TLC. The obtained solution was diluted with EtOAc, then neutralized to pH=5-6 by 1N hydrochloric acid, After removal of solvent by evaporating under reduced pressure, the obtained mixture was sequentially extracted by EtOAc (15 mL×3 times), and washed by brine (10 mL), dried by anhydrous $Na_2SO_4$ and concentrated to obtain a crude product which was purified by column chromatography (CHCl$_3$/MeOH=20:1-10:1) to obtain product CFH367-C (71 mg, 68.3%, pale yellow solid). $^1$H NMR (300 MHz, CD$_3$OD) δ 8.36 (t, J=5.4 Hz, 1H), 7.88 (d, J=3.0 Hz 1H), 7.74 (d, J=3.0 Hz 1H), 3.41 (q, J=6.6 Hz, 2H), 3.31-3.36 (m, 1H), 2.16 (t, J=6.6 Hz, 2H), 1.64-1.69 (m, 4H), 1.29-1.34 (m, 2H), 0.82-0.86 (m, 2H).

The following compounds could be synthesized using the same method as above:

| Compound | Structural formula | $^1$H NMR (CD$_3$OD, 300 MHz) data |
|---|---|---|
| CFH326 | | δ 8.53 (t, J = 5.4 Hz, 1H), 8.27 (s, 1H), 7.92 (d, J = 3.0 Hz, 1H), 7.89 (s, 1H), 7.77 (d, J = 3.0 Hz 1H), 3.43 (q, J = 6.0 Hz, 2H), 2.16 (t, J = 6.6 Hz, 2H), 1.66-1.69 (m, 4H) |
| CFH340-M | | δ 8.53 (t, J = 5.4 Hz, 1H), 8.27 (s, 1H), 7.92 (d, J = 3.0 Hz, 1H), 7.89 (s, 1H), 7.77 (d, J = 3.0 Hz, 1H), 3.43 (q, J = 6.0 Hz, 2H), 2.16 (t, J = 6.6 Hz, 2H), 1.66-1.69 (m, 4H) |

-continued

| Compound | Structural formula | $^1$H NMR (CD$_3$OD, 300 MHz) data |
|---|---|---|
| CFH355 | | δ 8.33 (t, J = 5.4 Hz, 1H), 7.89 (d, J = 3.3 Hz, 1H), 7.73 (d, J = 3.3 Hz, 1H), 3.37 (q, J = 6.6 Hz, 2H), 3.31 (q, J = 6.9 Hz, 2H), 2.16 (t, J = 6.3 Hz, 2H), 1.64-1.67 (m, 4H), 1.35 (t, J = 6.9 Hz, 3H) |
| CFH369 | | δ 8.35 (t, J = 5.4 Hz, 1H), 7.90 (d, J = 3.3 Hz, 1H), 7.74 (d, J = 3.3 Hz, 1H), 4.32-4.36 (m, 1H), 3.41 (q, J = 6.3 Hz, 2H), 2.16 (t, J = 6.3 Hz, 2H), 1.67-1.69 (m, 4H), 1.37 (d, J = 6.9 Hz, 6H) |
| CFH383 | | δ 8.38 (t, J = 5.4 Hz, 1H), 7.92 (d, J = 3.3 Hz, 1H), 7.76 (d, J = 3.3 Hz, 1H), 3.40 (q, J = 6.0 Hz, 2H), 3.34 (t, J = 6.0 Hz, 2H), 2.19 (t, J = 6.6 Hz, 2H), 1.72-1.79 (m, 6H), 1.41-1.54 (m, 2H), 1.01 (t, J = 7.5 Hz, 3H) |
| CFH382 | | (DMSO-d$_6$) δ 10.36 (s, 1H), 8.68 (s, 1H), 8.36 (t, J = 5.7 Hz, 1H), 7.99 (d, J = 3.0 Hz, 1H), 7.96 (d, J = 3.0 Hz, 1H), 3.25 (q, J = 5.7 Hz, 2H), 3.20 (d, J = 7.2 Hz, 2H), 1.96 (t, J = 5.4 Hz, 2H), 1.90-1.92 (m, 1H), 1.51 (m, 4H), 0.91 (d, J = 6.6 Hz, 6H) |
| CFH340 | | (DMSO-d$_6$) δ 10.61 (s, 1H), 8.84 (s, 1H), 8.46 (t, J = 6.9 Hz, 1H), 8.0 (d, J = 2.7 Hz, 2H), 3.81 (d, J = 5.4 Hz, 2H), 3.21 (d, J = 6.9 Hz, 2H), 1.92-1.96 (m, 1H), 0.93 (d, J = 6.6 Hz, 6H) |
| CFH354 | | (DMSO-d$_6$) δ 10.52 (s, 1H), 8.41 (t, J = 5.7 Hz, 1H), 7.97 (d, J = 2.4 Hz, 2H), 3.48 (q, J = 5.7 Hz, 2H), 3.20 (d, J = 6.0 Hz, 2H), 2.13 (t, J = 5.4 Hz, 2H), 1.90-1.92 (m, 1H), 0.91 (d, J = 6.0 Hz, 6H) |
| CFH368 | | (DMSO-d$_6$) δ 10.42 (s, 1H), 8.73 (s, 1H), 8.41 (t, J = 5.7 Hz, 1H), 7.97 (d, J = 3.0 Hz, 1H), 7.95 (d, J = 3.0 Hz, 1H), 3.27 (q, J = 6.6 Hz, 2H), 3.19 (d, J = 7.2 Hz, 2H), 2.02 (t, J = 7.2 Hz, 2H), 1.89-1.93 (m, 1H), 1.74-1.86 (m, 2H), 0.90 (d, J = 6.6 Hz, 6H) |

-continued

| Compound | Structural formula | ¹H NMR (CD₃OD, 300 MHz) data |
|---|---|---|
| CFH396 | | (DMSO-d₆) δ 10.39 (s, 1H), 8.33 (t, J = 5.4 Hz, 1H), 7.97 (d, J = 3.3 Hz, 1H), 7.93 (d, J = 3.3 Hz, 1H), 3.24 (q, J = 6.3 Hz, 2H), 3.19 (d, J = 7.2 Hz, 2H), 1.95 (t, J = 7.5 Hz, 2H), 1.87-1.91 (m, 1H), 1.49-1.54 (m, 4H), 1.26-1.28 (m, 2H), 0.91 (d, J = 6.3 Hz, 6H) |
| CFH410 | | δ 8.26 (d, J = 3.3 Hz, 1H), 7.85 (d, J = 6.6 Hz, 1H), 7.67 (d, J = 3.3 Hz, 1H), 3.30 (q, J = 7.2 Hz, 2H), 3.16 (d, J = 7.2 Hz, 2H), 2.07 (t, J = 7.5 Hz, 2H), 1.89-1.97 (m, 1H), 1.54-1.57 (m, 4H), 1.25-1.33 (m, 4H), 0.92 (d, J = 6.6 Hz, 6H) |
| CFH424 | | (DMSO-d₆) δ 10.33 (s, 1H), 8.66 (s, 1H), 8.34 (t, J = 5.7 Hz, 1H), 7.99 (d, J = 3.3 Hz, 1H), 7.97 (d, J = 3.0 Hz, 1H), 3.23-3.25 (m, 2H), 3.20 (d, J = 7.2 Hz, 2H), 1.96 (t, J = 7.2 Hz, 2H), 1.86-1.91 (m, 1H), 1.48-1.52 (m, 4H), 1.19-1.26 (m, 6H), 0.92 (d, J = 6.6 Hz, 6H) |
| CFH381 | | δ 8.44 (t, J = 5.4 Hz, 1H), 7.92 (d, J = 3.3 Hz, 1H), 7.81-7.89 (m, 1H), 7.78 (d, J = 3.3 Hz, 1H), 5.81 (d, J = 17.7 Hz, 1H), 5.51 (d, J = 10.8 Hz, 1H), 3.40 (q, J = 5.7 Hz, 2H), 2.15 (t, J = 7.5 Hz, 2H), 1.63-1.68 (m, 4H) |
| CFH395 | | δ 8.33 (t, J = 5.4 Hz, 1H), 7.89 (s, 2H), 7.73 (s, 1H), 7.54 (d, J = 15.9 Hz, 1H), 6.26-6.34 (m, 1H), 3.39 (q, J = 5.7 Hz, 2H), 2.48-2.50 (m, 1H), 2.16 (t, J = 6.6 Hz, 2H), 1.63-1.68 (m, 4H), 1.11 (d, J = 6.6 Hz, 6H) |
| CFH367 | | (DMSO-d₆) δ 10.37 (s, 1H), 8.69 (s, 1H), 8.42 (t, J = 5.4 Hz, 1H), 8.00 (s, 2H), 7.58 (d, J = 16.2 Hz, 1H), 6.35 (m, 1H), 3.27 (m, 2H), 1.98 (t, J = 6.9 Hz, 2H), 1.73 (d, J = 6.6 Hz, 3H), 1.51 (m, 4H) |
| CFH352 | | (DMSO-d₆) δ 10.36 (s, 1H), 8.69 (s, 1H), 8.52 (t, J = 5.4 Hz, 1H), 8.04 (s, 2H), 7.83 (dd, J = 17.7, 11.1 Hz, 1H), 5.83 (d, J = 17.7 Hz, 1H), 5.55 (d, J = 11.1 Hz, 1H), 3.28 (m, 2H), 1.98 (t, J = 6.9 Hz, 2H), 1.51 (m, 4H) |

-continued

| Compound | Structural formula | $^1$H NMR (CD$_3$OD, 300 MHz) data |
|---|---|---|
| CFH399 | | δ 8.47 (t, J = 5.4 Hz, 1H), 7.91 (d, J = 3.0 Hz, 1H), 7.74 (d, J = 3.0 Hz, 1H), 3.58 (s, 2H), 3.41 (q, J = 6.0 Hz, 2H), 2.16 (t, J = 6.3 Hz, 2H), 1.63-1.67 (m, 4H), 1.23 (s, 6H) |
| CFH367-C | | δ 8.36 (t, J = 5.4 Hz, 1H), 7.88 (d, J = 3.0 Hz, 1H), 7.74 (d, J = 3.0 Hz, 1H), 3.41 (q, J = 6.6 Hz, 2H), 3.31-3.36 (m, 1H), 2.16 (t, J = 6.6 Hz, 2H), 1.64-1.69 (m, 4H), 1.29-1.34 (m, 2H), 0.82-0.86 (m, 2H) |
| CFH409 | | δ 7.90 (d, J = 3.3 Hz, 1H), 7.74 (d, J = 3.3 Hz, 1H), 3.93-4.01 (m, 1H), 3.40 (t, J = 6.6 Hz, 2H), 2.16 (t, J = 7.2 Hz, 2H), 1.77-1.89 (m, 2H), 1.66-1.69 (m, 6H), 1.29-1.57 (m, 6H) |
| CFH409-A | | δ 8.29 (t, J = 5.4 Hz, 1H), 7.89 (s, 1H), 7.85 (d, J = 3.3 Hz, 1H), 7.70 (d, J = 3.3 Hz, 1H), 3.31 (q, J = 6.3 Hz, 2H), 3.15-3.17 (m, 1H), 2.16 (t, J = 6.0 Hz, 2H), 1.65-1.68 (m, 4H), 1.16-1.22 (m, 2H), 1.06 (d, J = 6.6 Hz, 3H), 1.02 (d, J = 6.6 Hz, 3H), 0.92-0.96 (m, 2H) |
| CFH403 | | δ 8.48 (t, J = 5.4 Hz, 1H), 7.93 (d, J = 3.0 Hz, 1H), 7.89 (s, 1H), 7.77 (d, J = 3.0 Hz, 1H), 7.59 (d, J = 6.6 Hz, 2H), 7.42-7.44 (m, 3H), 3.41 (q, J = 6.0 Hz, 2H), 2.12 (t, J = 6.6 Hz, 2H), 1.62-1.64 (m, 4H) |
| CFH421 | | δ 8.51 (t, J = 5.4 Hz, 1H), 7.93 (d, J = 3.0 Hz, 1H), 7.89 (s, 1H), 7.78 (d, J = 3.0 Hz, 1H), 7.62 (t, J = 5.1 Hz, 2H), 7.17 (t, J = 8.4 Hz, 2H), 3.33 (q, J = 8.4 Hz, 2H), 2.13 (t, J = 6.3 Hz, 2H), 1.63-1.65 (m, 4H) |

| Compound | Structural formula | ¹H NMR (CD₃OD, 300 MHz) data |
|---|---|---|
| CFH455 | | δ 8.52 (t, J = 5.4 Hz, 1H), 7.95 (d, J = 3.3 Hz, 1H), 7.82 (d, J = 3.3 Hz, 1H), 7.53 (t, J = 8.7 Hz, 1H), 7.37 (d, J = 8.7 Hz, 1H), 7.18 (t, J = 8.1 Hz, 1H), 3.34 (q, J = 6.6 Hz, 2H), 2.12 (t, J = 6.6 Hz, 2H), 1.62-1.64 (m, 4H) |
| CFH437 | | δ 8.47 (t, J = 5.4 Hz, 1H), 7.94 (d, J = 3.0 Hz, 1H), 7.79 (d, J = 3.0 Hz, 1H), 7.50 (t, J = 7.8 Hz, 2H), 7.39 (t, J = 7.8 Hz, 2H), 3.31 (q, J = 6.6 Hz, 2H), 1.99 (t, J = 5.4 Hz, 2H), 1.17-1.19 (m, 4H) |
| CFH447 | | δ 8.48 (t, J = 5.4 Hz, 1H), 8.25 (d, J = 8.4 Hz, 1H), 7.97 (d, J = 7.8 Hz, 1H), 7.91 (d, J = 3.0 Hz, 1H), 7.58 (t, J = 8.1 Hz, 2H), 7.53 (d, J = 3.0 Hz, 1H), 3.40 (q, J = 6.6 Hz, 2H), 2.44 (t, J = 6.9 Hz, 2H), 1.63-1.72 (m, 4H) |
| CFH448-P | | δ 8.22 (d, J = 7.2 Hz, 2H), 7.90 (d, J = 3.0 Hz, 1H), 7.79 (d, J = 6.9 Hz, 2H), 7.58 (t, J = 6.0 Hz, 1H), 7.53 (d, J = 3.0 Hz, 1H), 3.40 (q, J = 6.6 Hz, 2H), 2.34 (t, J = 6.9 Hz, 2H), 1.59-1.74 (m, 4H) |
| CFH417 | | δ 8.43 (t, J = 5.4 Hz, 1H), 7.86 (d, J = 3.0 Hz, 1H), 7.73 (d, J = 3.0 Hz, 1H), 7.23-7.34 (m, 5H), 4.70 (s, 2H), 3.44 (q, J = 6.3 Hz, 2H), 2.17 (t, J = 6.6 Hz, 2H), 1.65-1.69 (m, 4H) |
| CFH430 | | δ 8.39 (d, J = 16.5 Hz, 1H), 7.94 (d, J = 3.0 Hz, 1H), 7.90 (s, 1H), 7.79 (d, J = 3.0 Hz, 1H), 7.59 (d, J = 6.9 Hz, 2H), 7.32-7.38 (m, 3H), 7.18 (d, J = 16.5 Hz, 1H), 3.43 (q, J = 6.9 Hz, 2H), 2.16 (t, J = 7.5 Hz, 2H), 1.63-1.70 (m, 4H) |

-continued

| Compound | Structural formula | ¹H NMR (CD₃OD, 300 MHz) data |
| --- | --- | --- |
| CFH461 | | (CDCl₃) δ 7.84 (d, J = 3.0 Hz, 1H), 7.70 (t, J = 5.4 Hz, 1H), 7.41 (d, J = 3.0 Hz, 1H), 7.27-7.41 (m, 5H), 4.53 (s, 2H), 3.76 (t, J = 4.5 Hz, 2H), 3.67 (t, J = 4.8 Hz, 2H), 3.34 (q, J = 5.1 Hz, 2H), 2.18 (t, J = 6.6 Hz, 2H), 1.61-1.69 (m, 4H) |
| CFH324-C | | δ 7.89 (d, J = 3.3 Hz, 1H), 7.74 (d, J = 3.3 Hz, 1H), 4.04 (s, 2H), 3.30-3.32 (m, 1H), 1.29-1.34 (m, 2H), 0.83-0.85 (m, 2H) |
| CFH338 | | δ 8.37 (t, J = 5.4 Hz, 1H), 7.89 (s, 1H), 7.85 (d, J = 3.0 Hz, 1H), 7.70 (d, J = 3.0 Hz, 1H), 3.68 (q, J = 5.7 Hz, 2H), 3.25-3.31 (m, 1H), 2.46 (t, J = 6.3 Hz, 2H), 1.28-1.31 (m, 2H), 0.79-0.81 (m, 2H) |
| CFH352-C | | δ 8.34 (t, J = 5.4 Hz, 1H), 7.88 (s, 1H), 7.85 (d, J = 3.0 Hz, 1H), 7.71 (d, J = 3.0 Hz, 1H), 3.44 (q, J = 6.3 Hz, 2H), 3.23-3.28 (m, 1H), 2.21 (t, J = 7.2 Hz, 2H), 1.91-1.99 (m, 2H), 1.27-1.33 (m, 2H), 0.77-0.83 (m, 2H) |
| CFH381-C | | δ 8.24 (t, J = 5.4 Hz, 1H), 7.89 (s, 1H), 7.85 (d, J = 3.0 Hz, 1H), 7.71 (d, J = 3.0 Hz, 1H), 3.39 (q, J = 6.0 Hz, 2H), 3.24-3.29 (m, 1H), 2.13 (t, J = 7.5 Hz, 2H), 1.63-1.71 (m, 4H), 1.42-1.44 (m, 2H), 1.27-1.33 (m, 2H), 0.78-0.83 (m, 2H) |
| CFH395-C | | δ 8.27 (t, J = 5.4 Hz, 1H), 7.89 (s, 1H), 7.87 (d, J = 3.0 Hz, 1H), 7.72 (d, J = 3.0 Hz, 1H), 3.40 (q, J = 6.6 Hz, 2H), 3.25-3.29 (m, 1H), 2.11 (t, J = 7.2 Hz, 2H), 1.63-1.67 (m, 4H), 1.40-1.43 (m, 4H), 1.28-1.35 (m, 2H), 0.80-0.85 (m, 2H) |
| CFH409-C | | δ 8.25 (t, J = 5.4 Hz, 1H), 7.89 (s, 1H), 7.87 (d, J = 3.0 Hz, 1H), 7.72 (d, J = 3.0 Hz, 1H), 3.40 (q, J = 6.6 Hz, 2H), 3.25-3.28 (m, 1H), 2.09 (t, J = 7.2 Hz, 2H), 1.62-1.65 (m, 4H), 1.33-1.39 (m, 6H), 1.28-1.35 (m, 2H), 0.79-0.86 (m, 2H) |

| Compound | Structural formula | $^1$H NMR (CD$_3$OD, 300 MHz) data |
|---|---|---|
| CFH397-2 | | δ 8.34 (t, J = 5.7 Hz, 1H), 7.90 (s, 1H), 7.55 (s, 1H), 3.38 (q, J = 6.6 Hz, 2H), 3.20 (d, J = 6.9 Hz, 2H), 2.53 (s, 3H), 2.33 (t, J = 7.2 Hz, 2H), 1.92-2.01 (m, 1H), 1.64-1.67 (m, 4H), 0.97 (d, J = 6.6 Hz, 6H) |
| CFH381-B | | δ7.89 (s, 1H), 7.26 (s, 1H), 3.41 (q, J = 6.0 Hz, 2H), 3.26-3.31 (m, 1H), 2.44 (s, 3H), 2.15 (t, J = 6.0 Hz, 2H), 1.63-1.68 (m, 4H), 1.28-1.31 (m, 2H), 0.80-0.82 (m, 2H) |
| CFH381-M | | δ7.89 (s, 1H), 7.54 (s, 1H), 3.41 (q, J = 6.0 Hz, 2H), 3.26-3.31 (m, 1H), 2.54 (s, 3H), 2.16 (t, J = 6.0 Hz, 2H), 1.63-1.68 (m, 4H), 1.28-1.31 (m, 2H), 0.79-0.81 (m, 2H) |
| CFH395-M | | δ7.90 (s, 1H), 3.40 (q, J = 6.0 Hz, 2H), 3.24-3.26 (m, 1H), 2.39 (s, 3H), 2.30 (s, 3H), 1.99 (t, J = 5.4 Hz, 2H), 1.63-1.68 (m, 4H), 1.26-1.29 (m, 2H), 0.77-0.78 (m, 2H) |
| CFH421-C | | δ7.89 (s, 1H), 3.40 (q, J = 6.6 Hz, 2H), 3.25-3.30 (m, 1H), 2.84 (t, J = 4.2 Hz, 2H), 2.76 (t, J = 4.2 Hz, 2H), 2.16 (t, J = 6.6 Hz, 2H), 1.83-1.89 (m, 4H), 1.67-1.69 (m, 4H), 1.26-1.32 (m, 2H), 0.79-0.83 (m, 2H) |
| CFH407 | | δ 8.22 (s, 1H), 3.36 (q, J = 6.6 Hz, 2H), 3.21-3.24 (m, 1H), 2.90 (t, J = 6.6 Hz, 2H), 2.77 (t, J = 6.6 Hz, 2H), 2.49 (t, J = 6.3 Hz, 2H), 2.11 (q, J = 6.6 Hz, 2H), 1.62-1.70 (m, 4H), 1.23-1.26 (m, 2H), 0.74-0.76 (m, 2H) |
| CFH435 | | δ7.91 (s, 1H), 3.40 (q, J = 6.6 Hz, 2H), 3.25-3.28 (m, 1H), 2.94 (t, J = 5.4 Hz, 2H), 2.90 (t, J = 5.1 Hz, 2H), 2.16 (t, J = 6.6 Hz, 2H), 1.88-1.92 (m, 2H), 1.68-1.75 (m, 8H), 1.26-1.32 (m, 2H), 0.77-0.83 (m, 2H) |

| Compound | Structural formula | ¹H NMR (CD₃OD, 300 MHz) data |
|---|---|---|
| CFH449 | | δ 7.90 (s, 1H), 3.40 (q, J = 6.6 Hz, 2H), 3.24-3.27 (m, 1H), 2.94 (t, J = 5.4 Hz, 2H), 2.87 (t, J = 6.0 Hz, 2H), 2.15 (t, J = 6.3 Hz, 2H), 1.69-1.77 (m, 8H), 1.37-1.44 (m, 4H), 1.21-1.24 (m, 2H), 0.78-0.81 (m, 2H) |
| CFH412-C | | δ 8.61 (s, 1H), 3.38 (q, J = 6.0 Hz, 2H), 3.28-3.31 (m, 1H), 2.15 (t, J = 6.3 Hz, 2H), 1.63-1.68 (m, 4H), 1.22-1.29 (m, 2H), 0.71-0.73 (m, 2H) |
| CFH407-C | | δ 7.83 (s, 1H), 7.12 (s, 1H), 3.33 (q, J = 6.3 Hz, 2H), 3.17-3.24 (m, 1H), 2.10 (t, J = 5.7 Hz, 2H), 1.99-2.03 (m, 1H), 1.59-1.64 (m, 4H), 1.20-1.23 (m, 2H), 0.88-0.92 (m, 2H), 0.81-0.87 (m, 2H), 0.72-0.79 (m, 2H) |
| CFH449-H | | δ 7.89 (s, 1H), 3.35 (q, J = 6.6 Hz, 2H), 3.24-3.28 (m, 1H), 2.78 (t, J = 4.2 Hz, 2H), 2.71 (t, J = 4.2 Hz, 2H), 2.15 (t, J = 6.6 Hz, 2H), 1.89-1.98 (m, 4H), 1.61-1.69 (m, 4H), 1.32-1.38 (m, 4H), 1.25-1.28 (m, 2H), 0.76-0.80 (m, 2H) |
| CFH443-5 | | δ 8.15 (s, 1H), 7.72 (d, J = 7.2 Hz, 2H), 7.45-7.47 (m, 3H), 3.44 (q, J = 6.3 Hz, 2H), 3.31-3.35 (m, 1H), 2.16 (t, J = 7.2 Hz, 2H), 1.70-1.75 (m, 4H), 1.30-1.35 (m, 2H), 0.82-0.88 (m, 2H) |
| CFH443-4 | | δ 8.34 (s, 1H), 7.94 (d, J = 12 Hz, 2H), 7.35-7.43 (m, 3H), 3.41 (q, J = 6.3 Hz, 2H), 3.27-3.31 (m, 1H), 2.17 (t, J = 7.2 Hz, 2H), 1.68-1.73 (m, 4H), 1.30-1.33 (m, 2H), 0.84-0.85 (m, 2H) |
| CFH455-C | | δ 7.77 (s, 1H), 7.72 (d, J = 8.1 Hz, 2H), 7.41 (d, J = 7.8 Hz, 2H), 4.60 (d, J = 6.0 Hz, 2H), 3.26-3.31 (m, 1H), 2.74 (s, 4H), 1.85 (s, 4H), 1.21-1.26 (m, 2H), 0.74-0.78 (m, 2H) |

-continued

| Compound | Structural formula | $^1$H NMR (CD$_3$OD, 300 MHz) data |
|---|---|---|
| CFH401 | | δ 7.87 (d, J = 3.3 Hz, 1H), 7.74 (d, J = 3.3 Hz, 1H), 7.72 (d, J = 8.4 Hz, 2H), 7.47 (d, J = 7.8 Hz, 2H), 4.65 (s, 2H), 3.31-3.35 (m, 1H), 1.30-1.33 (m, 2H), 0.83-0.85 (m, 2H) |
| CFH403-1 | | δ 7.91 (d, J = 8.7 Hz, 2H), 7.85 (d, J = 3.3 Hz, 1H), 7.83 (d, J = 8.4 Hz, 2H), 7.77 (d, J = 3.3 Hz, 1H), 3.28 (d, J = 7.2 Hz, 2H), 1.96-2.05 (m, 1H), 1.02 (d, J = 6.6 Hz, 6H) |
| CFH429 | | δ 8.03 (s, 1H), 7.92 (d, J = 3.3 Hz, 1H), 7.78 (d, J = 3.3 Hz, 1H), 7.69 (d, J = 7.5 Hz, 1H), 7.57 (d, J = 15.0 Hz, 1H), 7.34-7.39 (m, 2H), 6.49 (d, J = 15.9 Hz, 1H), 3.28 (d, J = 7.2 Hz, 2H), 2.02-2.04 (m, 1H), 1.01 (d, J = 6.6 Hz, 6H) |
| CFH394 | | (DMSO-d$_6$) δ 10.53 (s, 1H), 8.76 (s, 1H), 7.98 (d, J = 3.0 Hz, 1H), 7.93 (d, J = 2.7 Hz, 1H), 4.49 (d, J = 13.2 Hz, 1H), 3.66 (d, J = 12.9 Hz, 1H), 3.16 (t, J = 13.5 Hz, 1H), 2.95 (t, J = 12.3 Hz, 1H), 2.78 (d, J = 6.9 Hz, 2H), 2.29-2.32 (m, 1H), 1.85-1.90 (m, 1H), 1.70-1.83 (m, 1H), 1.53-1.60 (m, 3H), 0.90 (d, J = 6.6 Hz, 6H) |
| CFH412-4 | | δ 9.9 (s, 1H), 8.36 (s, 1H), 8.25 (s, 1H), 7.89 (s, 1H), 4.39 (t, J = 7.2 Hz, 1H), 3.28 (q, J = 8.9 Hz, 2H), 2.11-2.21 (m, 1H), 1.83 (t, J = 7.8 Hz, 2H), 1.04 (d, J = 6.9 Hz, 6H) |
| CFH384 | | δ 9.09 (s, 1H), 8.36 (s, 1H), 8.26 (s, 1H), 7.89 (s, 1H), 4.46 (d, J = 6.6 Hz, 1H), 3.85 (d, J = 6.6 Hz, 2H), 2.23-2.26 (m, 1H), 1.06 (d, J = 6.9 Hz, 6H) |

-continued

| Compound | Structural formula | $^1$H NMR (CD$_3$OD, 300 MHz) data |
|---|---|---|
| CFH398-4 | | δ 9.08 (s, 1H), 8.36 (s, 1H), 8.28 (d, J = 9.0 Hz, 1H), 8.24 (s, 1H), 7.89 (s, 1H), 4.39 (t, J = 7.2 Hz, 1H), 3.50 (q, J = 4.8 Hz, 2H), 2.34 (t, J = 6.9 Hz, 2H), 2.15-2.22 (m, 1H), 1.03 (d, J = 6.6 Hz, 6H) |
| CFH398-M | | (DMSO-d$_6$) δ 10.55 (s, 1H), 8.86 (s, 1H), 8.54 (t, J = 5.4 Hz, 1H), 8.33 (s, 1H), 8.23 (s, 1H), 8.01 (d, J = 9.0 Hz, 1H), 4.45 (t, J = 6.3 Hz, 1H), 3.50 (d, J = 4.2 Hz, 2H), 2.73 (s, 3H), 2.10 (m, 1H), 0.94 (d, J = 6.9 Hz, 3H), 0.89 (d, J = 6.9 Hz, 3H) |
| CFH412-M | | δ 8.27 (d, J = 8.4 Hz, 1H), 8.21 (s, 1H), 8.12 (s, 1H), 7.89 (s, 1H), 4.38 (d, J = 6.0 Hz, 1H), 3.36 (t, J = 6.0 Hz, 2H), 2.76 (s, 3H), 2.34 (t, J = 6.0 Hz, 2H), 2.15-2.21 (m, 1H), 1.02 (d, J = 6.6 Hz, 6H) |
| CFH426-M | | δ 8.34 (t, J = 6.0 Hz, 1H), 8.27 (d, J = 8.4 Hz, 1H), 8.21 (s, 1H), 8.12 (s, 1H), 7.89 (s, 1H), 4.38 (d, J = 7.2 Hz, 1H), 3.25 (t, J = 6.0 Hz, 2H), 2.76 (s, 3H), 2.17-2.20 (m, 1H), 2.14 (t, J = 7.2 Hz, 2H), 1.8-1.85 (m, 2H), 1.03 (d, J = 6.6 Hz, 6H) |
| CFH383-4 | | δ 9.06 (s, 1H), 8.51 (t, J = 5.4 Hz, 1H), 8.28 (s, 1H), 3.40 (q, J = 6.3 Hz, 2H), 3.23 (d, J = 7.2 Hz, 2H), 2.16 (t, J = 6.6 Hz, 2H), 1.97-2.02 (m, 1H), 1.68-1.71 (m, 4H), 1.03 (d, J = 6.6 Hz, 6H) |
| CFH397 | | δ 8.03 (s, 1H), 3.39 (q, J = 4.8 Hz, 2H), 3.21 (d, J = 7.2 Hz, 2H), 2.75 (s, 3H), 2.16 (t, J = 6.6 Hz, 2H), 1.96-2.00 (m, 1H), 1.67-1.69 (m, 4H), 0.98 (d, J = 6.6 Hz, 6H) |
| CFH326-4 | | (DMSO-d$_6$) δ 10.37 (s, 1H), 9.27 (s, 1H), 8.69 (s, 1H), 8.47 (t, J = 5.7 Hz, 1H), 8.36 (s, 1H), 8.27 (s, 1H), 3.29 (q, J = 5.4 Hz, 2H), 1.98 (t, J = 6.9 Hz, 2H), 1.52 (m, 4H) |
| CFH340-4 | | (DMSO-d$_6$) δ 10.36 (s, 1H), 8.68 (s, 1H), 8.43 (t, J = 6.0 Hz, 1H), 8.24 (s, 1H), 8.14 (s, 1H), 3.30 (q, J = 6.9 Hz, 2H), 2.74 (s, 3H), 1.98 (t, J = 6.9 Hz, 2H), 1.52 (m, 4H) |

-continued

| Compound | Structural formula | $^1$H NMR (CD$_3$OD, 300 MHz) data |
|---|---|---|
| CFH456 | | δ 8.16 (s, 2H), 4.56 (d, J = 5.1 Hz, 2H), 3.43 (q, J = 5.7 Hz, 2H), 2.16 (t, J = 7.2 Hz, 2H), 1.49-1.69 (m, 4H), 1.48 (s, 9H) |
| CFH470 | | (DMSO-d$_6$) δ 10.28 (s, 1H), 8.70 (s, 1H), 8.45 (s, 1H), 8.25 (s, 1H), 8.20 (s, 1H), 7.89 (t, J = 5.7 Hz, 1H), 4.45 (d, J = 5.1 Hz, 2H), 3.27 (q, J = 5.7 Hz, 2H), 2.21 (t, J = 7.2 Hz, 2H), 1.49 (m, 6H), 1.42 (s, 9H) |
| CFH484 | | δ 8.16 (s, 1H), 7.76 (d, J = 3.3 Hz, 1H), 7.21 (d, J = 3.3 Hz, 1H), 4.56 (s, 2H), 3.43 (q, J = 5.7 Hz, 2H), 2.16 (t, J = 7.2 Hz, 2H), 1.23-1.59 (m, 8H), 1.22 (s, 9H) |

Example 2 of Preparation

Compound Number CFH494

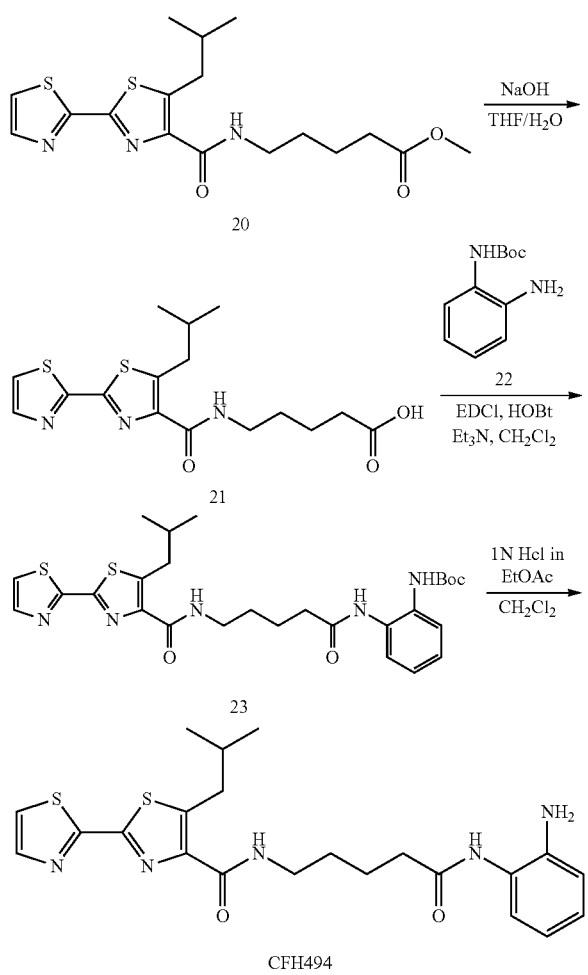

Compound 20 (90 mg, 0.24 mmol) was dissolved in THF/H$_2$O (5 mL, 4:1). NaOH (12 mg, 0.29 mmol) was added and stirred for 2 h at room temperature. The reaction mixture was acidified to pH=2-3 with 1N hydrochloric acid, extracted by EtOAc (10 mL×3 times), washed with brine (20 mL), dried by anhydrous Na$_2$SO$_4$, and concentrated to obtain compound 21 (85 mg, 98%, white solid). $^1$H NMR (300 MHz, CD3OD) δ 7.86 (d, J=3.3 Hz, 1H), 7.70 (d, J=3.3 Hz, 1H), 3.38 (t, J=6.3 Hz, 2H), 3.20 (d, J=7.2 Hz, 2H), 2.36 (t, J=6.9 Hz, 2H), 1.89-2.00 (m, 1H), 1.66-1.68 (m, 4H), 0.96 (d, J=6.6 Hz, 6H).

Compound 21 (93 mg, 0.25 mmol) was dissolved in dry CH$_2$Cl$_2$ (5 mL). Compound 22 (74 mg, 0.35 mmol), HOBt (41 mg, 0.30 mmol), Et$_3$N (36 mg, 0.35 mmol) were added in respectively and stirred for 10 min at 0° C., then EDCI (82 mg, 0.43 mmol) was added in. The reaction was kept at room temperature overnight. The obtained reaction mixture was sequentially washed by 1N hydrochloric acid (10 mL), saturated sodium bicarbonate solution (10 mL) and brine, dried by anhydrous Na$_2$SO$_4$, concentrated and purified by flash chromotography (PE/EtOAc=2: 1-1:1) to obtain compound 23 (74 mg, 52.5%, colorless transparent oil). $^1$H NMR (300 MHz, CDCl3) δ 7.86 (d, J=3.3 Hz, 1H), 7.66 (t, J=5.4 Hz, 1H), 7.52 (d, J=7.8 Hz, 1H), 7.45 (d, J=3.3 Hz, 1H), 7.35 (d, J=7.8 Hz, 1H), 7.06-7.14 (m, 2H), 3.40 (q, J=6.3 Hz, 2H), 3.26 (d, J=6.9 Hz, 2H), 2.38 (t, J=6.6 Hz, 2H), 1.98-2.01 (m, 1H), 1.66-1.76 (m, 4H), 1.48 (s, 9H), 0.98 (d, J=6.6 Hz, 6H).

Compound 23 (73 mg, 0.13 mmol) was dissolved in CH$_2$Cl$_2$ (2 mL), and then EtOAc solution of 1N hydrochloric acid (2 mL) was added and stirred for 10 min at room temperature. Product CFH494 (60 mg, 93.8%, white solid) was obtained after concentration. $^1$H NMR (300 MHz, CD3OD) δ 7.93 (d, J=3.3 Hz, 1H), 7.80 (d, J=3.3 Hz 1H), 7.47-7.52 (m, 2H), 7.35-7.42 (m, 3H), 3.45 (q, J=6.6 Hz, 2H), 3.31 (d, J=7.2 Hz, 2H), 2.59 (t, J=6.6 Hz, 2H), 1.81-2.00 (m, 1H), 1.74-1.79 (m, 4H), 0.98 (d, J=6.6 Hz, 6H).

The following compounds were synthesized using the same method as above:

| Compound | Structural formula | $^1$H NMR (CD$_3$OD, 300 MHz) data |
|---|---|---|
| CHF494 | 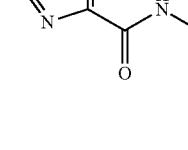 | δ 7.93 (d, J = 3.3 Hz, 1H), 7.80 (d, J = 3.3 Hz, 1H), 7.47-7.52 (m, 2H), 7.35-7.42 (m, 3H), 3.45 (q, J = 6.6 Hz, 2H), 3.31 (d, J = 7.2 Hz, 2H), 2.59 (t, J = 6.6 Hz, 2H), 1.81-2.00 (m, 1H), 1.74-1.79 (m, 4H), 0.98 (d, J = 6.6 Hz, 6H) |
| CFH508 | 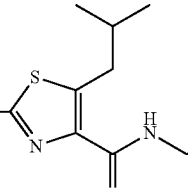 | δ 7.92 (d, J = 3.3 Hz, 1H), 7.79 (d, J = 3.3 Hz, 1H), 7.40-7.49 (m, 4H), 7.34 (t, J = 7.8 Hz, 1H), 3.36 (t, J = 6.9 Hz, 2H), 3.19 (d, J = 7.2 Hz, 2H), 2.52 (t, J = 7.2 Hz, 2H), 1.92-1.96 (m, 1H), 1.76-1.81 (m, 2H), 1.65-1.73 (m, 2H), 1.44-1.48 (m, 2H), 0.93 (d, J = 6.6 Hz, 6H) |
| CFH522 | 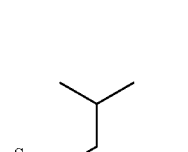 | δ 7.88 (d, J = 3.3 Hz, 1H), 7.73 (d, J = 3.3 Hz, 1H), 7.47-7.49 (m, 2H), 7.31-7.43 (m, 2H), 4.06 (t, J = 6.6 Hz, 2H), 3.05 (d, J = 6.9 Hz, 2H), 2.51 (t, J = 7.2 Hz, 2H), 1.98-2.05 (m, 1H), 1.78-1.86 (m, 4H), 1.53-1.67 (m, 4H), 1.03 (d, J = 6.6 Hz, 6H) |
| CFH500 | 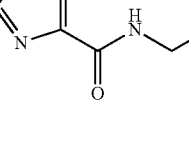 | (CDCl$_3$) δ 8.71 (s, 1H), 8.66 (s, 1H), 7.87 (d, J = 3.3 Hz, 1H), 7.63 (t, J = 5.4 Hz, 1H), 7.45 (d, J = 3.3 Hz, 1H), 7.41 (d, J = 6.6 Hz, 1H), 7.32 (d, J = 5.7 Hz, 1H), 7.13-7.15 (m, 2H), 3.45 (q, J = 6.6 Hz, 2H), 3.27 (d, J = 7.2 Hz, 2H), 2.38 (t, J = 6.6 Hz, 2H), 2.10 (s, 3H), 1.97-2.01 (m, 1H), 1.68-1.76 (m, 4H), 0.99 (d, J = 6.6 Hz, 6H) |
| CFH514 | 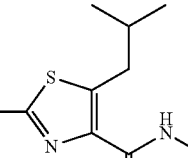 | (CDCl$_3$) δ 8.79 (s, 2H), 7.87 (d, J = 3.0 Hz, 1H), 7.58 (t, J = 5.4 Hz, 1H), 7.44 (d, J = 3.3 Hz, 1H), 7.31-7.36 (m, 2H), 7.11-7.14 (m, 2H), 3.40 (q, J = 6.9 Hz, 2H), 3.28 (d, J = 6.9 Hz, 2H), 2.32 (t, J = 7.5 Hz, 2H), 2.10 (s, 3H), 2.00-2.07 (m, 1H), 1.60-1.73 (m, 4H), 1.38-1.46 (m, 2H), 1.00 (d, J = 6.6 Hz, 6H) |
| CFH325 | 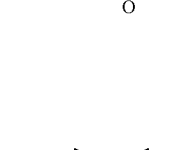 | δ 7.74 (d, J = 3.0 Hz, 1H), 7.58 (d, J = 3.0 Hz, 1H), 4.00 (d, J = 5.1 Hz, 2H), 3.07 d, J = 7.2 Hz, 2H), 1.82-1.88 (m, 1H), 0.84 (d, J = 6.6 Hz, 6H) |

-continued

| Compound | Structural formula | ¹H NMR (CD₃OD, 300 MHz) data |
|---|---|---|
| CFH339-A | | δ 7.86 (d, J = 3.0 Hz, 1H), 7.70 (d, J = 3.0 Hz, 1H), 3.62 (t, J = 6.6 Hz, 2H), 3.20 (d, J = 7.2 Hz, 2H), 2.63 (t, J = 6.6 Hz, 2H), 1.89-2.01 (m, 1H), 0.96 (d, J = 6.6 Hz, 6H) |
| CFH353 | | δ 7.89 (d, J = 3.3 Hz, 1H), 7.72 (d, J = 3.3 Hz, 1H), 3.43 (t, J = 6.9 Hz, 2H), 3.23 (d, J = 6.9 Hz, 2H), 2.41 (t, J = 7.5 Hz, 2H), 1.98-2.03 (m, 1H), 1.89-1.96 (m, 2H), 0.99 (d, J = 6.6 Hz, 6H) |
| CFH367-A | | δ 7.86 (d, J = 3.3 Hz, 1H), 7.70 (d, J = 3.3 Hz, 1H), 3.38 (t, J = 6.3 Hz, 2H), 3.20 (d, J = 7.2 Hz, 2H), 2.36 (t, J = 6.9 Hz, 2H), 1.89-2.00 (m, 1H), 1.66-1.68 (m, 4H), 0.96 (d, J = 6.6 Hz, 6H) |
| CFH381-A | | δ 7.84 (d, J = 3.3 Hz, 1H), 7.67 (d, J = 3.3 Hz, 1H), 3.33 (t, J = 6.9 Hz, 2H), 3.17 (d, J = 6.9 Hz, 2H), 2.15 (t, J = 7.5 Hz, 2H), 1.86-1.97 (m, 1H), 1.50-1.67 (m, 4H), 1.33-1.43 (m, 2H), 0.93 (d, J = 6.6 Hz, 6H) |
| CFH381-A | | δ 7.83 (d, J = 3.0 Hz, 1H), 7.43 (d, J = 3.0 Hz, 1H), 3.82 (q, J = 7.2 Hz, 2H), 3.13 (d, J = 6.9 Hz, 2H), 2.29 (t, J = 7.5 Hz, 2H), 1.91-1.98 (m, 1H), 1.82-1.89 (m, 2H), 1.54-1.60 (m, 2H), 1.20-1.35 (m, 4H), 0.93 (d, J = 6.6 Hz, 6H) |
| CFH410-A | | δ 8.33 (t, J = 5.7 Hz, 1H), 7.88 (d, J = 3.0 Hz, 1H), 7.72 (d, J = 3.0 Hz, 1H), 3.36 (q, J = 6.9 Hz, 2H), 3.26 (d, J = 7.5 Hz, 2H), 2.26 (t, J = 7.2 Hz, 2H), 1.93-2.00 (m, 1H), 1.58-1.61 (m, 4H), 1.34-1.37 (m, 6H), 0.99 (d, J = 6.6 Hz, 6H) |
| CFH379 | | δ 7.89 (d, J = 3.3 Hz, 1H), 7.71 (d, J = 3.3 Hz, 1H), 4.49 (d, J = 13.2 Hz, 1H), 3.77 (d, J = 13.8 Hz, 1H), 3.07-3.26 (m, 2H), 2.84 (d, J = 7.2 Hz, 2H), 2.63-2.70 (m, 1H), 2.04-2.08 (m, 1H), 1.87-1.99 (m, 2H), 1.66-1.80 (m, 2H), 0.97 (d, J = 6.6 Hz, 6H) |

Example 3 of Preparation

Compound Number CFH412

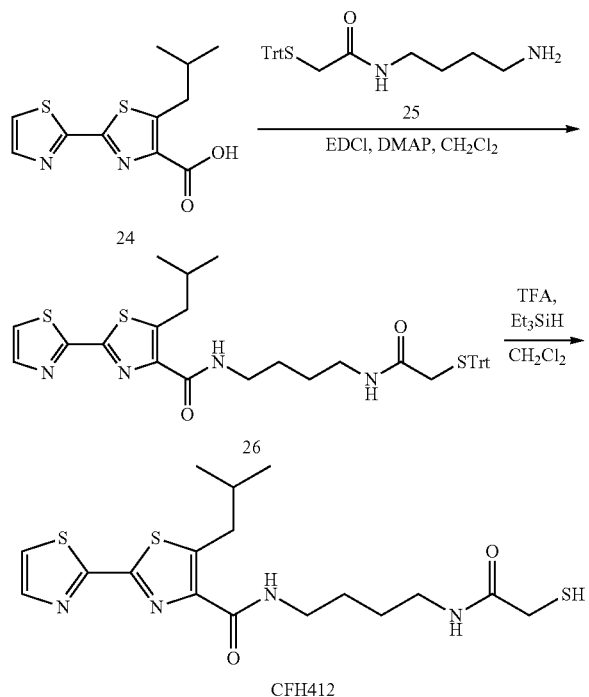

Compound 24 (500 mg, 1.87 mmol) was dissolved in dry CH$_2$Cl$_2$ (15 mL) and then compound 25 (754 mg, 1.87 mmol), EDCI (488 mg, 2.80 mmol), DMAP (23 mg, 0.19 mmol) were sequentially added in. The reaction was kept at room temperature overnight. The reaction mixture was sequentially washed with saturated sodium bicarbonate solution (10 mL) and brine. The aqueous phase was extracted with CHCl$_3$ (10 mL×2 times). The combination of organic phases was dried with anhydrous Na$_2$SO$_4$, concentrated and purified by column chromatography (PE/EtOAc=2: 1-1:1) to obtain product 26 (640 mg, 52.5%, yellow grease). $^1$H NMR (300 MHz, CDCl3) δ 7.78 (d, J=3.0 Hz, 1H), 7.51 (t, J=6.3 Hz, 1H), 7.35 (d, J=8.1 Hz, 6H), 7.29 (d, J=3.0 Hz, 1H), 7.11-7.23 (m, 9H), 6.15 (t, J=6.0 Hz, 1H), 3.32 (q, J=6.0 Hz, 2H), 3.22 (d, J=7.2 Hz, 2H), 3.05 (s, 2H), 2.96 (q, J=6.0 Hz, 2H), 1.94-1.96 (m, 1H), 1.44-1.46 (m, 2H), 1.35-1.40 (m, 2H), 0.94 (d, J=6.6 Hz, 6H).

Compound 26 (320 mg, 0.5 mmol) was dissolved in CH$_2$Cl$_2$ (5 mL). Et$_3$SiH (188 mg, 1.65 mmol) and trifluoroacetic acid (5.6 g, 0.05 mol) were added in and stirred for 2 h at room temperature. The reaction mixture was concentrated under reduced pressure and purified by silica gel column chromotography (PE/EA=1:1-1:5) to obtain product CFH412 (150 mg, 74.4%, pale yellow grease). $^1$H NMR (300 MHz, CDCl3) δ 7.78 (d, J=3.0 Hz, 1H), 7.59 (t, J=5.7 Hz, 1H), 7.38 (d, J=3.0 Hz 1H), 7.31 (t, J=5.7 Hz, 1H), 3.36 (q, J=6.3 Hz, 2H), 3.26 (q, J=5.7 Hz, 2H), 3.19 (s, 2H), 3.17 (d, J=7.2 Hz, 2H), 1.86-1.97 (m, 1H), 1.47-1.58 (m, 4H), 0.89 (d, J=6.6 Hz, 6H).

The following compounds were synthesized using the same method as above:

| Compounds | Structural formula | $^1$H NMR (CDCl$_3$, 300 MHz) data |
|---|---|---|
| CFH398-S | | δ 7.81 (d, J = 3.0 Hz, 1H), 7.76 (t, J = 6.6 Hz, 1H), 7.57 (t, J = 5.7 Hz, 1H), 7.41 (d, J = 3.0 Hz, 1H), 3.44 (q, J = 6.3 Hz, 2H), 3.31 (q, J = 5.7 Hz, 2H), 3.23 (s, 2H), 3.20 (d, J = 6.9 Hz, 2H), 1.91-1.96 (m, 1H), 1.73-1.77 (m, 2H), 0.92 (d, J = 6.6 Hz, 6H) |
| CFH412 | | δ 7.78 (d, J = 3.0 Hz, 1H), 7.59 (t, J = 5.7 Hz, 1H), 7.38 (d, J = 3.0 Hz, 1H), 7.31 (t, J = 5.7 Hz, 1H), 3.36 (q, J = 6.3 Hz, 2H), 3.26 (q, J = 5.7 Hz, 2H), 3.19 (s, 2H), 3.17 (d, J = 7.2 Hz, 2H), 1.86-1.97 (m, 1H), 1.47-1.58 (m, 4H), 0.89 (d, J = 6.6 Hz, 6H) |
| CFH426 | | δ 7.74 (d, J = 3.0 Hz, 1H), 7.52 (t, J = 5.4 Hz, 1H), 7.36 (d, J = 3.0 Hz, 1H), 7.10 (t, J = 5.7 Hz, 1H), 3.29 (q, J = 6.6 Hz, 2H), 3.17 (q, J = 5.7 Hz, 2H), 3.15 (s, 2H), 3.14 (d, J = 7.5 Hz, 2H), 1.85-1.93 (m, 1H), 1.44-1.55 (m, 4H), 1.29-1.31 (m, 2H), 0.86 (d, J = 6.6 Hz, 6H) |

| Compounds | Structural formula | ¹H NMR (CDCl₃, 300 MHz) data |
|---|---|---|
| CFH440 | | δ 7.72 (d, J = 3.3 Hz, 1H), 7.49 (t, J = 5.7 Hz, 1H), 7.34 (d, J = 3.3 Hz, 1H), 7.14 (t, J = 5.7 Hz, 1H), 3.25 (q, J = 6.6 Hz, 2H), 3.13 (q, J = 5.7 Hz, 2H), 3.10 (s, 2H), 3.09 (d, J = 7.2 Hz, 2H), 1.81-1.94 (m, 1H), 1.37-1.47 (m, 4H), 1.06-1.11 (m, 4H), 0.83 (d, J = 6.6 Hz, 6H) |
| CFH367-S | | δ 7.99 (dd, J = 17.4, 11.1 Hz, 1H), 7.92 (d, J = 3.0 Hz, 1H), 7.73 (t, J = 3.6 Hz, 1H), 7.51 (d, J = 3.0 Hz, 1H), 5.78 (d, J = 17.4 Hz, 1H), 5.53 (d, J = 11.1 Hz, 1H), 3.54 (q, J = 6.6 Hz, 2H), 3.40 (q, J = 6.0 Hz, 2H), 3.29 (d, J = 9.0 Hz, 2H), 1.77-1.87 (m, 2H) |
| CFH397-S | | δ 7.90 (d, J = 3.0 Hz, 1H), 7.79 (t, J = 6.6 Hz, 1H), 7.61 (s, 1H), 7.47 (d, J = 3.0 Hz, 1H), 3.53 (q, J = 6.3 Hz, 2H), 3.39 (q, J = 5.7 Hz, 2H), 3.28 (d, J = 8.7 Hz, 2H), 2.04 (s, 6H), 1.77-1.85 (m, 2H) |
| CFH383-S | | δ 7.88 (d, J = 3.3 Hz, 1H), 7.69-7.73 (m, 1H), 7.46 (d, J = 3.3 Hz, 1H), 5.28-6.33 (m, 1H), 3.50 (q, J = 6.6 Hz, 2H), 3.37 (q, J = 6.3 Hz, 2H), 3.25 (d, J = 9.0 Hz, 2H), 1.82-1.94 (m, 3H), 1.75-1.80 (m, 2H) |
| CFH411 | | δ 7.69 (d, J = 3.3 Hz, 1H), 7.41 (d, J = 10.5 Hz, 1H), 7.27 (d, J = 3.3 Hz, 1H), 6.07 (dd, J = 15.9, 6.9 Hz, 1H), 3.32 (q, J = 5.4 Hz, 2H), 3.19 (q, J = 5.4 Hz, 2H), 3.08 (d, J = 8.7 Hz, 2H), 2.31-2.38 (m, 1H), 1.60-1.64 (m, 2H), 0.89 (d, J = 7.2 Hz, 6H) |

Embodiment of Preparation 4

Compound Number CFH538

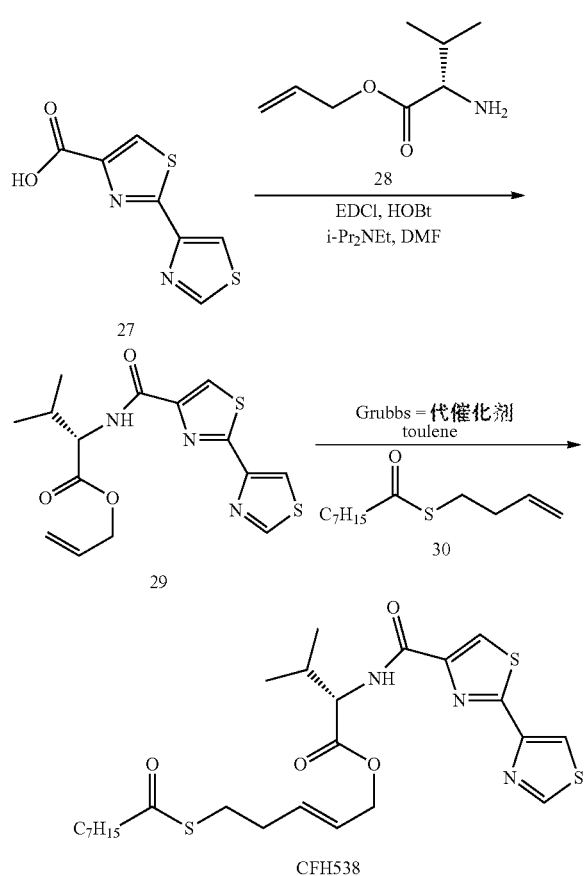

Compound 27 (100 mg, 0.47 mmol) was dissolved in dry DMF (5 mL) and the mixture was cooled to 0° C. in an ice-bath. EDCI (108 mg, 0.57 mmol) and HOBt (76 mg, 0.57 mmol) were added in and stirred for 10 min at 0° C. Then, compound 28 (81 mg, 0.52 mmol) and i-Pr$_2$NEt (91 mg, 0.71 mmol) were added in and stirred for 12 h at room temperature. The obtained reaction mixture was diluted with 20 mL of water, extracted by EtOAc (15 mL×3 times). The combined organic phases was washed by brine (20 mL) and then dried by anhydrous Na$_2$SO$_4$. After removal of the solvent, product 29 (129 mg, 77.9%, colorless grease) was obtained after purification by silica gel column chromatography (PE/EtOAc=3:1). $^1$H NMR (300 MHz, CDCl$_3$) δ 8.83 (s, 1H), 8.10 (s, 1H), 8.05 (s, 1H), 7.81 (d, J=9.0 Hz, 1H), 5.87 (dddd, J=17.1, 10.5, 5.7, 5.1 Hz, 1H), 5.31 (d, J=17.1 Hz, 1H), 5.23 (d, J=10.5 Hz, 1H), 4.73 (dd, J=9.3, 5.1 Hz, 1H), 4.65 (dd, J=17.1, 5.7 Hz, 2H), 2.23-2.33 (m, 1H), 0.96 (t, J=6.9 Hz, 6H).

Compound 29 (55 mg, 0.16 mmol) was dissolved in redistilled toluene (5 mL). To this solution was added a toluene solution (1 mL) of Grubbs second generation catalyst (66 mg, 0.08 mmol), and toluene (1 mL) solution of compound 30 (100 mg, 0.48 mmol). The reaction mixture was heated to 110° C. and refluxed for 12 h. The obtained reaction mixture was concentrated and then purified by silica gel column chromatography (PE/EtOAc=2:1) to obtain product CFH538 (23 mg, 50%, pale yellow grease). Crude material 29 (25 mg) was recycled. $^1$H NMR (300 MHz, CDCl$_3$) δ 8.86 (s, 1H), 8.13 (s, 1H), 8.11 (s, 1H), 7.83 (d, J=9.0 Hz, 1H), 5.74 (dt, J=15.3, 6.6 Hz, 1H), 5.63 (dt, J=13.2, 6.0 Hz, 1H), 4.74 (dd, J=9.0, 5.4 Hz, 1H), 4.66 (dd, J=15.3, 5.4 Hz, 2H), 2.91 (t, J=7.5 Hz, 2H), 2.52 (t, J=7.5 Hz, 2H), 2.35-2.43 (m, 2H), 2.22-2.32 (m, 1H), 1.60-1.67 (m, 2H), 1.19-1.26 (m, 8H), 1.04 (t, J=6.3 Hz, 6H), 0.86 (t, J=6.9 Hz, 3H).

The following compounds were synthesized using the same method as above:

| Compounds | Structural formula | $^1$H NMR (CDCl$_3$, 300 MHz) data |
|---|---|---|
| CFH550 | | δ 7.87 (d, J = 3.0 Hz, 1H), 7.48 (t, J = 4.5 Hz, 1H), 7.44 (d, J = 3.0 Hz, 1H), 5.47 (ddd, J = 12.6, 6.3, 6.3 Hz, 1H), 5.37 (ddd, J = 10.5, 6.0, 6.0 Hz, 1H), 3.43 (q, J = 7.2 Hz, 2H), 3.28 (d, J = 7.5 Hz, 2H), 2.88 (t, J = 7.5 Hz, 2H), 2.51 (t, J = 7.5 Hz, 2H), 2.21 (m, 1H), 1.99 (m, 4H), 1.61 (m, 4H), 1.38 (m, 4H), 1.23 (m, 8H), 0.89 (d, J = 6.9 Hz, 6H), 0.83 (t, J = 6.6 Hz, 3H) |
| CFH384-S | | δ 9.38 (s, 1H), 7.89 (d, J = 3.0 Hz, 1H), 7.46 (d, J = 3.0 Hz, 1H), 3.80 (q, J = 6.3 Hz, 2H), 3.66 (t, J = 6.3 Hz, 2H), 3.51 (d, J = 7.2 Hz, 2H), 2.15 (m, 1H), 1.78 (m, 2H), 1.61 (m, 2H), 1.48 (m, 4H), 0.86 (d, J = 6.6 Hz, 6H) |

| Compounds | Structural formula | ¹H NMR (CDCl₃, 300 MHz) data |
|---|---|---|
| CFH412-S | | δ 8.87 (s, 1H), 8.14 (s, 1H), 8.09 (s, 1H), 7.84 (d, J = 9 Hz, 1H), 5.78 (dt, J = 15.3, 6.6 Hz, 1H), 5.68 (dt, J = 12.3, 6.3 Hz, 1H), 4.76 (dd, J = 8.7, 4.8 Hz, 1H), 4.65 (dd, J = 15.3, 5.4 Hz, 2H), 2.58 (q, J = 7.5 Hz, 2H), 2.39-2.44 (m, 2H), 2.31-2.37 (m, 1H), 1.04 (d, J = 6.3 Hz, 6H) |
| CFH426-S | | δ 8.11 (s, 1H), 7.89 (s, 1H), 7.86 (d, J = 6.3 Hz, 1H), 5.77 (ddd, J = 15.3, 6.3, 6.3 Hz, 1H), 5.65 (ddd, J = 14.4, 6.6, 6.6 Hz, 1H), 4.74 (dd, J = 9.0, 4.8 Hz, 1H), 4.64 (dd, J = 15.3, 6.9 Hz, 2H), 2.77 (s, 3H), 2.57 (q, J = 7.5 Hz, 2H), 2.36-2.43 (m, 2H), 2.28-2.34 (m, 1H), 1.05 (d, J = 6.3 Hz, 3H) |
| CFH538 | | δ 8.86 (s, 1H), 8.13 (s, 1H), 8.11 (s, 1H), 7.83 (d, J = 9.0 Hz, 1H), 5.74 (dt, J = 15.3, 6.6 Hz, 1H), 5.63 (dt, J = 13.2, 6.0 Hz, 1H), 4.74 (dd, J = 9.0, 5.4 Hz, 1H), 4.66 (dd, J = 15.3, 5.4 Hz, 2H), 2.91 (t, J = 7.5 Hz, 2H), 2.52 (t, J = 7.5 Hz, 2H), 2.35-2.43 (m, 2H), 2.22-2.32 (m, 1H), 1.60-1.67 (m, 2H), 1.19-1.26 (m, 8H), 1.04 (t, J = 6.3 Hz, 6H), 0.86 (t, J = 6.9 Hz, 3H) |
| CFH552 | | δ 8.10 (s, 1H), 7.89 (s, 1H), 7.82 (d, J = 9.0 Hz, 1H), 5.75 (ddd, J = 15.3, 6.6, 6.6 Hz, 1H), 5.67 (ddd, J = 14.4, 7.2, 7.2 Hz, 1H), 4.74 (dd, J = 9.0, 5.1 Hz, 1H), 4.61 (dd, J = 15.3, 4.5 Hz, 2H), 2.90 (t, J = 7.2 Hz, 2H), 2.77 (s, 3H), 2.51 (t, J = 7.2 Hz, 2H), 2.31-2.36 (m, 2H), 2.27-2.30 (m, 1H), 1.61-1.66 (m, 2H), 1.19-1.27 (m, 8H), 1.02 (t, J = 6.6 Hz, 6H), 0.86 (t, J = 7.2 Hz, 3H) |

Example 5 of Preparation

Compound Number CFH325-B

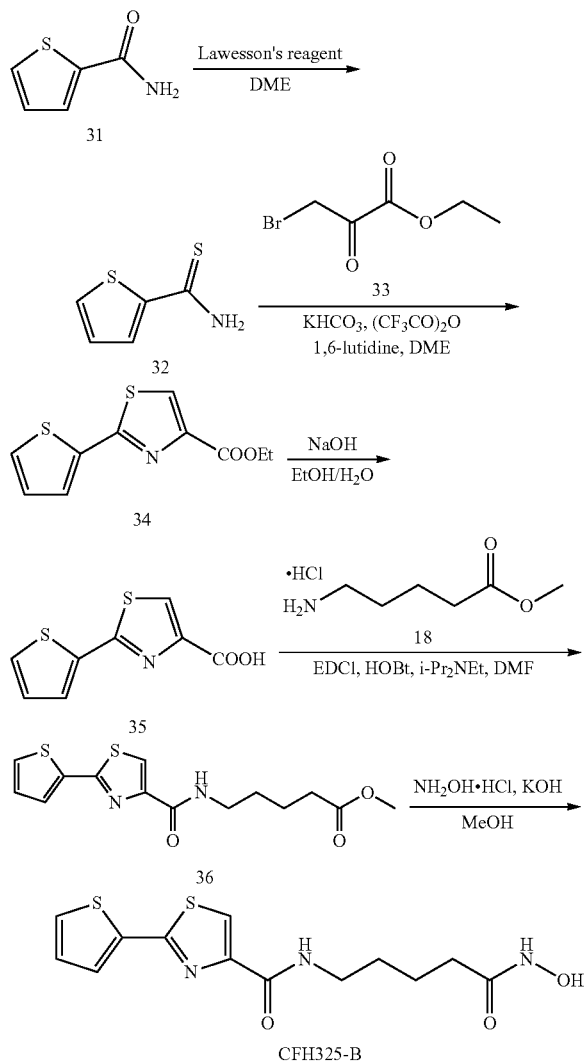

Compound 31 (1 g, 7.86 mmol) was dissolved in dry DME (30 mL). Lawesson's reagent (1.6 g, 3.9 mmol) was added in with the protection of $N_2$. After 12 h of reaction at room temperature, Compound 32 (1.0 g, 88.8%, white solid), was obtained after filtration, removal of solvent, and purification by silica gel column chromatography (PE/EtOAc=10: 1-2:1). Compound 32 was used for next reaction directly.

Compound 32 (500 mg, 3.49 mmol) was dissolved in dry DME (30 mL). $KHCO_3$ (2.1 g, 21 mmol) was added and stirred for 10 min at room temperature. Compound 33 (1.5 g, 7.68 mmol) was added dropwise. After 1 h of reaction, the reaction mixture was cooled in an ice-bath and then added dropwise trifluoroacetic anhydride (2.2 g, 10.48 mmol) and DME (10 mL) solution of 2,6-lutidine (1.87 g, 17.46 mmol). The reaction was kept at 0° C. for 1 h, and kept overnight after rising to room temperature. After the reaction of compound 32 was completed which was detected by TLC, the solvent was removed by evaporating under reduced pressure and then diluted with EtOAc (50 mL). The organic phase was sequentially washed with 1N hydrochloric acid (20 mL), saturated sodium bicarbonate (20 mL) and brine (20 mL), and dried with anhydrous $Na_2SO_4$. Compound 34 (647 mg of 77.4%, pale yellow solid) was obtained after purification by silica gel chromatography (PE/EtOAc=4: 1-2:1). $^1$H NMR (300 MHz, CDCl3) δ 8.00 (s, 1H), 7.50 (d, J=3.9 Hz, 1H), 7.36 (d, J=5.1 Hz, 1H), 7.00 (dd, J=4.8, 3.9 Hz, 1H), 4.34 (q, J=7.2 Hz, 2H), 1.33 (t, J=7.2 Hz, 3H)

Compound 34 (447 mg, 1.87 mmol) was dissolved in EtOH/$H_2O$ (20/5 mL). NaOH (149 mg, 3.74 mol) solid was added in at 0° C. and was stirred at room temperature overnight. After the completion of the reaction, EtOH was removed under reduced pressure, diluted with $H_2O$ and acidified to pH=2 by 1N hydrochloric acid and extraction by EtOAc (20 mL×3 times). The collected organic phase was washed by brine (20 mL) and then dried with anhydrous $Na_2SO_4$. Compound 35 was obtained by concentration, which was used directly for the next reaction.

Compound 35 (110 mg, 0.52 mmol) was dissolved in dry DMF (5 mL), then cooled to 0° C. in an ice-bath. EDCI (150 mg, 0.78 mmol) and HOBt (106 mg, 0.78 mmol) was added in and stirred for 10 min at 0° C. Compound 18 (96 mg, 0.57 mmol) and i-$Pr_2$NEt (134 mg, 1.04 mmol) were added in and stirred for 12 h at room temperature. The obtained mixture was diluted with 20 mL water, and then extracted by EtOAc (15 mL×3 times). The combined organic phases was washed by 1N hydrochloric acid (15 ml), saturated sodium bicarbonate solution (15 ml) and brine (20 mL) in sequence, and then dried with anhydrous $Na_2SO_4$. After removal of solvent by evaporating under reduced pressure, the obtained residue was purified by silica gel column chromatography (PE/EtOAc=2: 1) to obtain product compound 36 (146 mg, 86.4%, pale yellow grease). $^1$H NMR (300 MHz, CDCl$_3$) δ 7.95 (s, 1H), 7.47 (d, J=3.9 Hz, 1H), 7.39 (d, J=5.1 Hz, 1H), 7.03 (dd, J=5.1, 3.9 Hz, 1H), 3.62 (s, 3H), 3.42 (q, J=6.3 Hz, 2H), 2.31 (t, J=6.6 Hz, 2H), 1.65-1.71 (m, 4H).

Hydroxylamine hydrochloride (215 mg, 3.1 mmol) was suspended in MeOH (15 mL), and then KOH (260 mg, 4.65 mmol) was added and stirred for 5 min. The insoluble substance was removed by filtration and the filtrate was collected for next use. After compound 36 (100 mg, 0.31 mmol) was dissolved in anhydrous MeOH (10 ml), freshly-prepared above-mentioned MeOH solution of hydroxylamine hydrochloride was added in and stirred for 1 h at room temperature. Reaction endpoint was determined by TLC. The obtained solution was diluted with EtOAc, then neutralized to pH=5-6 by 1N hydrochloric acid. After removal of solvent by evaporating under reduced pressure, the obtained mixture was sequentially extracted by EtOAc (15 mL×3 times), and washed by brine (10 mL), dried by anhydrous $Na_2SO_4$ and concentrated to obtain the crude product which was purified by column chromatography (CHCl$_3$/MeOH=20:1-10:1) to obtain product CFH325-B (86 mg, 86%, white solid). $^1$H NMR (300 MHz, CD$_3$OD) δ 8.09 (s, 1H), 7.87 (s, 1H), 7.66 (d, J=3.9 Hz, 1H), 7.60 (d, J=5.1 Hz, 1H), 7.14 (dd, J=3.9, 5.1 Hz, 1H), 3.42 (q, J=6.3 Hz, 2H), 2.16 (t, J=6.6 Hz, 2H), 1.68-1.71 (m, 4H).

TESTING EXAMPLE OF BIO-EXPERIMENT

Testing Example 1

Experiment of Detecting the Inhibitory Activity for Histone Deacetylase 1, 3, 6 (HDAC1, 3, 6)

1. Experimental Objective:
The objective is to detect the inhibitory activity of the compounds against recombinant human histone deacetylase 1, 3, 6.

2. Source of the Material:

Human HDAC1, HDAC3 and HDAC6 are obtained from of the baculovirus expression system.

3. Principle:

Enzyme activity of HDAC1,3 is determined using the substrate Ac-Lys-Tyr-Lys(Ac)-AMC while the enzyme activity of HDAC6 is assayed using the substrate Boc-lys(Ac)-AMC. The reaction is carried out in flat-bottom, 96-well, or 384-well microplates. After the substrate was deacetylated by HDACs, the product AMC which was obtained from hydrolysis by trypsin can generate fluorescence signal. Measurement is taken in using an multilabe plate reader a 355 nm excitation filter and a 460 nm emission filter. The initial rate of fluorescence should accurately reflect the rate of product formation and enzyme activity.

4. Experimental Process

Sample processing: The sample was dissolved in DMSO and kept at a low temperature. DMSO in the final system is limited under a low concentration which won't affect the enzyme activity.

Data processing and results: The single concentration of the compounds, for example, 20 μg/ml, was used in the preliminary screening and the activity of the sample was tested. As for the samples that exhibit a certain activity, e.g. the inhibition ratio is greater than 50%, the activity-dose dependency relationship, $IC_{50}/EC_{50}$ value, were determined, which could be obtained by the nonlinear fitting of the activity against the concentration of the samples. The calculation software for the nonlinear fitting is Graphpad Prism 4, and the model for the fitting is sigmoidal dose-response (variable slope). For the most inhibitor-screening models, the bottom and the top of the fitted curve is set as 0 and 100. Generally, all measurements were duplicated (n≥2), and the results are indicated as mean±SD (Standard Deviation) or SE (standard error). A well-reported HDAC pan-inhibitor, SAHA (Vorinostat) was used as a positive control in each measurement.

5. Experimental Results:

| Sample No. | HDAC1 $IC_{50}(\mu M)$ | HDAC3 $IC_{50}(\mu M)$ | HDAC6 $IC_{50}(\mu M)$ | Sample No. | HDAC1 $IC_{50}(\mu M)$ | HDAC3 $IC_{50}(\mu M)$ | HDAC6 $IC_{50}(\mu M)$ |
|---|---|---|---|---|---|---|---|
| CFH326 | 0.212 | 0.107 | 1.110 | CFH401 | 0.042 | 0.030 | 0.020 |
| CFH340-M | 0.606 | 0.691 | 1.106 | CFH403-1 | 1.020 | 0.687 | 0.295 |
| CFH355 | 0.031 | 0.256 | 0.938 | CFH429 | 0.657 | 0.410 | 0.305 |
| CFH369 | 0.341 | 0.358 | 1.206 | CFH394 | NA | NA | NA |
| CFH383 | 0.031 | 0.188 | 0.621 | CFH412-4 | 2.587 | 1.638 | 29.451 |
| CFH382 | 0.047 | 0.102 | 1.217 | CFH384 | NA | NA | NA |
| CFH340 | NA[a] | NA | NA | CFH398-4 | 9.593 | 3.136 | NA |
| CFH354 | NA | NA | NA | CFH398-M | NA | NA | NA |
| CFH368 | NA | NA | 19.511 | CFH412-M | 2.655 | 2.218 | NA |
| CFH396 | 0.035 | 0.086 | 0.497 | CFH426-M | 2.453 | 1.577 | NA |
| CFH410 | 0.178 | 0.249 | 1.246 | CFH383-4 | 1.102 | 0.352 | 3.159 |
| CFH424 | 0.021 | 0.073 | 0.575 | CFH397 | 0.438 | 0.224 | 2.045 |
| CFH381 | 0.173 | 0.194 | 0.176 | CFH326-4 | 0.816 | 0.193 | 1.331 |
| CFH395 | 0.013 | 0.142 | 0.167 | CFH340-4 | 0.535 | 0.615 | 1.194 |
| CFH367 | 0.022 | 0.106 | 0.376 | CFH456 | 0.897 | 0.895 | 1.156 |
| CFH352 | 0.116 | 0.384 | 2.295 | CFH470 | 0.121 | 0.174 | 0.566 |
| CFH399 | 1.574 | 2.203 | 9.536 | CFH484 | 1.684 | 1.178 | 1.424 |
| CFH367-C | 0.065 | 0.262 | 0.785 | CFH494 | 5.911 | 3.814 | NA |
| CFH409 | 0.347 | 0.325 | 0.748 | CFH508 | 0.984 | 4.307 | NA |
| CFH409-A | 0.628 | 0.276 | 0.188 | CFH522 | 15.343 | NA | NA |
| CFH403 | 0.114 | 0.377 | 0.467 | CFH500 | NA | NA | NA |
| CFH421 | 0.204 | 0.314 | 0.501 | CFH514 | NA | NA | NA |
| CFH455 | 0.488 | 0.587 | 4.991 | CFH325 | NA | NA | NA |
| CFH437 | 0.165 | 0.453 | 5.178 | CFH339-A | NA | NA | NA |
| CFH447 | 0.270 | 0.364 | 0.473 | CFH353 | NA | NA | NA |
| CFH448-P | 0.105 | 0.201 | 1.067 | CFH367-A | NT[b] | NT | NT |
| CFH417 | 0.058 | 0.079 | 1.746 | CFH381-A | NT | NT | NT |
| CFH430 | 0.047 | 0.253 | 0.777 | CFH396-A | NT | NT | NT |
| CFH461 | 0.050 | 0.158 | 0.957 | CFH410-A | NA | NA | NA |
| CFH324-C | NA | NA | NA | CFH379 | NA | NA | NA |
| CFH338 | NA | NA | NA | CFH398-S | 0.181 | 0.327 | 0.088 |
| CFH352-C | 14.523 | 3.818 | 3.571 | CFH412 | 4.507 | 2.063 | 0.869 |
| CFH381-C | 0.052 | 0.037 | 0.105 | CFH426 | 0.263 | 0.495 | 0.190 |
| CFH395-C | 0.020 | 0.010 | 0.010 | CFH440 | 1.052 | 0.534 | 1.664 |
| CFH409-C | 0.086 | 0.064 | 0.134 | CFH367-S | 1.828 | 2.245 | 0.692 |
| CFH397-2 | 0.917 | 0.262 | 1.662 | CFH397-S | 1.222 | 0.315 | 0.181 |
| CFH381-B | 0.050 | 0.060 | 0.092 | CFH383-S | 0.937 | 0.728 | 0.470 |
| CFH381-M | 0.064 | 0.075 | 1.761 | CFH411 | 0.956 | 0.384 | 0.212 |
| CFH395-M | 0.050 | 0.097 | 0.565 | CFH550 | NA | NA | NA |
| CFH421-C | 0.025 | 0.063 | 1.857 | CFH384-S | 20.638 | 13.654 | NA |
| CFH407 | 0.086 | 0.130 | 1.290 | CFH412-S | 0.087 | 0.058 | 3.716 |
| CFH435 | 0.218 | 0.161 | 1.823 | CFH426-S | 0.117 | 0.106 | 4.324 |
| CFH449 | 0.147 | 0.176 | 1.784 | CFH538 | 1.898 | 2.831 | NA |
| CFH412-C | 6.274 | 2.913 | 3.068 | CFH552 | 2.600 | 3.558 | NA |
| CFH407-C | 0.106 | 0.052 | 0.332 | CFH325-B | 0.134 | 0.188 | 0.608 |
| CFH449-H | 0.011 | 0.016 | 0.049 | CFH443-5 | 0.032 | 0.011 | 0.488 |
| CFH455-C | 0.079 | 0.075 | 0.075 | CFH443-4 | 0.056 | 0.106 | 0.185 |

[a]the tested compound of 20 μg/mL has no inhibitory activity;
[b]untested.

It can be seen from the experimental results of the above table: the biological results of transformation of $R_2$ part showed that, alkyl groups, the substitution by alkene groups and aryl groups present good HDAC inhibitory activity. The diversification of the substituent group is conducive to the biological activity of the compounds. Isobutylene-substituted compound CFH395 has the best inhibitory activity on HDAC1. Compounds CFH355, CFH437 and CFH417 selectively inhibit HDAC1 (HDAC1/HDAC6=~30 times). Meanwhile compound CFH355 has a 8-time selectivity to HDAC1 and HDAC3.

At the same time, the biological activity showed that if $R_2$ parts remains same and Y is —($C_1$-$C_{10}$ alkyl group)-, the length of the chain has a large impact on the activity. Similarly, if the side chains have the same length, different $R_2$-substituted compounds have different activity either, such as a series of isobutyl-substituted compounds, the chain with 7 methylenes have the best inhibitory activity on HDAC1 while for cyclopropyl-substituted compounds, the chain with 6 methylenes have the best inhibitory activity.

With the $R_2$ group was isobutyl, the inventor has investigated fragment Y of the side chain and different type of Zn-chelating groups (ZBG). As for the inhibition of HDAC1, hydroxamic acid ZBG has the best activity. While ZBG is α-mercapto ketone, HDAC6 is selectively inhibited, such as CFH398-S.

With the $R_2$ group was cyclopropyl, and $R_{4b}$ and $R_{5b}$ substitution were investigated. It can be found from the inhibitory activity of HDAC that when $R_{4b}$ and $R_{5b}$ and C to which they are connected form a six-membered ring, i.e., compound CFH421-C, the inhibitory activity on HDAC1 is the best and HDAC1 is selectively inhibited (HDAC1/HDAC6=75 times).

Testing Example 2

Experiment for Testing the Cellular-Level Antitumor Activity

1. Experimental Objective:

The objective is to evaluate the antitumor activity of the compounds by testing the inhibitory activity of the compounds on the growth of the human colon cancer HCT-116 cell lines.

2. Principle of the Test:

The colorimetric assay, MTT assay is for assessing cell viability, which is based on the metabolic reduction of 3-(4, 5-dimethyl-2-thiazole)-2,5-diphenyl bromide tetrazolium (MTT). NAD(P)H-dependent cellular oxidoreductase enzymes in the mitochondria may, under defined conditions, reflect the number of viable cells present. These enzymes are capable of reducing the tetrazolium dye MTT (3-(4,5-dimethylthiazol-2-yl)-2,5-diphenyltetrazolium bromide to its insoluble formazan, which has a purple color. After using DMSO to dissolve Formazan, microplate reader can be used to measure the optical density at a wavelength of 550/690 nm.

3. Experimental Processing:

Sample processing: The sample was dissolved in DMSO and kept at a low temperature. DMSO in the final system is limited under a low concentration which won't affect the enzyme activity.

Cell viability was detected by using MTT assay. The cells kept in the logarithmic growth phase are digested by 0.05% trypsin and seeded overnight on 96-well plates at $2.0 \times 10^3$ per well in growth media. After seeding, cells are incubated with 5% $CO_2$ at 37° C. overnight. Six concentration gradients of the test compounds are added and plates are incubated at 37 for 72 hr and each concentration of each compound are triplicated. Then 20 μL of 5 mg/mL MTT are added to each well for 3 hours at 37° C., The mediums are removed and replaced with 100 μL of DMSO at 37° C. until crystals were dissolved. The absorbance's are measured using a SpectraMAX 340 microplate reader at 550 nm (L1), with a reference wavelength at 690 nm (L2). was plotted against different concentrations of the inhibitors. $IC_{50}$ are obtained by the nonlinear fitting of the (L1-L2) value, which is directly proportional to the number of viable cells, against the concentration of the samples.

Data processing and results: The single concentration of the compounds, for example, 20 μg/ml, was used in the preliminary screening and the activity of the sample was tested. As for the samples that exhibit a certain activity, e.g., the inhibition ratio is greater than 50%, the activity-dose dependency relationship, $IC_{50}/EC_{50}$ value, were determined, which could be obtained by the nonlinear fitting of the activity against the concentration of the samples. The calculation software for the nonlinear fitting is Graphpad Prism 4, and the model for the fitting is sigmoidal dose-response (variable slope). For the most inhibitor-screening models, the bottom and the top of the fitted curve is set as 0 and 100. Generally, all measurements were duplicated (n≥2), and the results are indicated as mean±SD (Standard Deviation) or SE (standard error). A reported compound doxorubicin (doxorubicin) was used as positive reference in each measurement.

4. Experimental Results:

4.1: Results of the Compounds on the HCT-116 Human Colon Cancer Cell Line:

| Sample No. | Cell Viability $IC_{50}$ (μM) | Sample No. | Cell Viability $IC_{50}$ (μM) | Sample No. | Cell Viability $IC_{50}$ (μM) |
|---|---|---|---|---|---|
| CFH326 | 11.143 ± 1.167 | CFH381-C | 0.438 ± 0.018 | CFH403 | 7.596 ± 0.817 |
| CFH369 | 8.714 ± 1.227 | CFH395-C | 0.408 ± 0.023 | CFH421-C | 0.233 ± 0.029 |
| CFH383 | 7.406 ± 1.473 | CFH409-C | 2.976 ± 0.188 | CFH407 | 0.310 ± 0.032 |
| CFH382 | 10.304 ± 1.130 | CFH381-B | 0.562 ± 0.071 | CFH435 | 0.768 ± 0.099 |
| CFH410 | 6.696 ± 0.652 | CFH381-M | 0.472 ± 0.055 | CFH449 | 0.392 ± 0.031 |
| CFH367-C | 0.452 ± 0.022 | CFH395-M | 0.538 ± 0.051 | CFH401 | 0.267 ± 0.007 |
| CFH461 | 7.647 ± 1.499 | CFH407-C | 1.117 ± 0.484 | | |
| CFH396 | 8.266 ± 0.858 | CFH409-A | 15.125 ± 2.919 | | |
| CFH508 | 9.322 ± 0.433 | CFH421 | 10.023 ± 0.748 | | |

4.2: Results of the Compounds on the BxPC-3 Human Colon Cancer Cell Line:

| Sample No. | Cell Viability $IC_{50}$ (μM) | Sample No. | Cell Viability $IC_{50}$ (μM) | Sample No. | Cell Viability $IC_{50}$ (μM) |
|---|---|---|---|---|---|
| CFH382 | 2.6 | CFH355 | 3.3 | CFH461 | 0.9 |
| CFH396 | 4.3 | CFH410 | 4.7 | CFH383 | 2.6 |

-continued

| Sample No. | Cell Viability IC$_{50}$ (μM) | Sample No. | Cell Viability IC$_{50}$ (μM) | Sample No. | Cell Viability IC$_{50}$ (μM) |
|---|---|---|---|---|---|
| CFH395 | 1.9 | CFH424 | 17.8 | CFH403 | 3.9 |
| CFH367 | 6.2 | CFH326 | 6.8 | CFH367-C | 1.3 |
| CFH397-2 | 3.7 | CFH340-M | 13.0 | CFH417 | 1.9 |
| CFH352 | 2.1 | CFH369 | 4.8 | | |
| CFH397 | 6.4 | CFH421 | 4.8 | | |

4.3: Results of the Compounds on Other Tumor Cell Lines:

| Sample No. | HL60 IC$_{50}$ (μM) | A549 IC$_{50}$ (μM) | MDA-MB-231 IC$_{50}$ (μM) | HMEC IC$_{50}$ (μM) |
|---|---|---|---|---|
| CFH395 | 0.3 | 1.6 | 0.5 | 1.2 |
| CFH367-C | 0.5 | 2.8 | 0.7 | 1.7 |
| CFH383-4 | 5.1 | 32.0 | 9.4 | 22.0 |
| CFH382 | NT[a] | 3.6 | 2.7 | NT |
| CFH417 | NT | 3.2 | 2.1 | NT |

[a] untested.

5. Conclusions: the compounds having inhibitory activity on HDAC1 without exception exhibit good activity in inhibiting tumor cell proliferation, in particular has a good impact on colon cancer, pancreatic cancer, adenocarcinoma of the lung, breast cancer. From the point of the inhibitory growth activity of the cancer cell lines, the activity of the compound on the cell is substantially consistent with that on the enzymes.

Testing Example 3

HDAC Inhibitor as the Drug for Treating Multiple Sclerosis (MS)

1. Experimental Method and Results:
The Clinical Score of EAE can be Effectively Alleviated by HDACi CFH367-C.

The inventor carried out a hypodermic injection of 100 μL MOG$_{35-55}$ emulsified by Freund's complete adjuvant (150 μg/mice) and MT toxin (5 mg/mL) by thermal inactivation on the 8-week-old female C57 mice. And, on the same day and on the third day intraperitoneal injection of PTX (200 ng/mice/time, dissolved by PBS) is carried out twice. On the third day after immunization, the mice are administered via gavage, twice daily, and each dose is 10 mg/kg of the body weight. The performance of the mice were observed daily and rated based on the following criteria: 0: no signs of incidence; tail with weakness (0.5 points) or paralysis (1 point); all fours with weakness (0.5 points) or paralysis (1 point). The above scores are counted up to achieve a final score. The results show that (FIG. 1), CFH367-C has a good therapeutic effect on the clinical symptoms of EAE, and the severity of the disease in the treated mice was significantly lower than control group of the solvent (P<0.01).

HDACi CFH367-C Significantly Reduced the Demyelination Phenomenon of Spinal Cords of EAE Animal.

The samples of spinal cords from normal control, EAE mice and the treatment group of EAE mice were taken respectively. After being fixed, the samples were enveloped by conventional paraffin embedding, section in 5 micrometers, hydration with dewaxing to 95% alcohol, staining with LFB (Luxol Fast Blue) overnight at 56 degree; washing by 95% ethanol and then by water, color separation using a 0.05% lithium carbonate solution, washing by 70% ethanol twice, washing by distilled water, staining with eosin for 2 minutes, gradient ethanol dehydration, transparency treatment by xylene, and mounting by neutral gum. The main coloring part of LFB is the white matter of the spinal cord, mainly composed of nerve fibers and their myelin. Experimental results showed that the white matter of normal mice can be dyed blue with a relatively dense structure; while the white matter regions of spinal cord in EAE mice appeared large number of vacuoles, and the degree of coloration was significantly reduced, showing a severe demyelination phenomenon. The mice administered with CFH367-C had a dense structure of the white matter of the spinal cord with an even coloring. This was close to the normal control mice, showing its significant therapeutic effect.

HDACi CFH367-C Significantly Reduced the Infiltration of the Peripheral Immune Cells in the Spinal Cord of EAE Animal.

The samples of spinal cords from normal control, EAE mice and the treatment group of EAE mice were taken respectively. After being fixed, the samples were treated by the following steps in sequence, which were conventional paraffin embedding and section in 5 micrometers. The sections were dewaxed by xylene, rehydrated by all levels of ethanol, and dyed with hematoxylin for five minutes; After that the slices were washed by running water, and the color was separated by hydrochloric acid. Then after water washing, the slices were dyed with eosin for 2 minutes; after dehydration by gradient ethanol dehydration, the slices were made transparent by xylene, and mounted with neutral gum. The experimental results show that almost no peripheral immune cells was infiltrated in the spinal cord of the normal mice; while the white matter regions in spinal cord of EAE mouse appeared a large number of peripheral immune cell with infiltration, and this caused the damage of annex tissue with the appearance of the vacuoles. The white matter structure of the spinal cord in the mice administered with CFH367-C is dense with no obvious infiltration in the peripheral immune cells, showing a significant therapeutic effect.

HDACi CFH367-C Significantly Reduced the Infiltration of CD54 Positive Leukocyte in the Spinal Cord of EAE Animal.

The HDACi CFH367-C significantly reduced EAE animal spinal cord CD45-positive leukocyte infiltration. Spinal cords are taken from the mice. After being fixed, the spinal cords are treated with OCT and made to be 10 μm frozen sections. The sections were washed with PBS three times, and each time for 5 min, then incubated overnight at 4° C. with antibody against CD45 (primary antibody); after being washed with PBS three times, the sections are dyed with fluorescence-labeled secondary antibody at 37° C. for 1 h. After being washed with PBS three times, the sections are mounted with glycerinum. CD45 is the common antigen of leukocyte. The experimental results showed that nuclear staining showed that there are a large number of cells aggregated in the spinal cord of EAE mice, and most of them were the CD45 positive leukocytes. This phenomenon did not exist in normal mice, while the aggregation of positive leukocyte also has not been observed in the mice which were administered with CFH367C, showing that the infiltration of the leukocyte to the spinal cord of EAE mice can be inhibited by CFH367-C.

HDACi CFH367-C Significantly Reduced the Infiltration of CD4 Positive T Cells in the Spinal Cord of EAE Animal.

Preliminary studies have indicated that CD4 positive T cells play an important role in the pathopoiesis of EAE. The inventor has also observed the function of the drugs on the filtration of CD4 positive T cells. Spinal cords were taken from the mice. After being fixed, the spinal cords were embedded in OCT to be made into 10 μm frozen sections. The sections were washed with PBS three times, and each time for 5 min, then incubated overnight at 4° C. with antibody (primary antibody) against CD4; After being washed with PBS three times, the sections are dyed with fluorescence-labeled secondary antibody at 37° C. for 1 h. After being washed with PBS three times, the sections are mounted by glycerinum. The experimental results showed that nuclear staining showed that there are a large number of cells aggregated in the spinal cord of EAE mice, and most of them were the CD4 positive T cells. This phenomenon did not exist in normal mice. The filtration and aggregation of the CD4 positive T cells can be obviously alleviated by administering CFH367-C.

2. Conclusions:

Histone deacetylase inhibitor CFH367-C can effectively alleviate the clinical symptoms of experimental mouse model EAE of MS. It is found by dyeing the spinal cord of EAE mice that CFH367-C can inhibit the peripheral immune cells, especially the infiltration of CD4 positive T cell to the central nervous system of the mice, and alleviate demyelinating phenomenon of the neurons of EAE animal and further alleviate the clinical manifestations of EAE. The present research results indicated that histone deacetylase inhibitor CFH367-C can be used in the treatment of MS disease and may be applied into treatments of other autoimmune diseases, including rheumatoid arthritis, psoriasis, systemic lupus erythematosus, etc.

The invention claimed is:

1. A thiazole compound of general formula I,

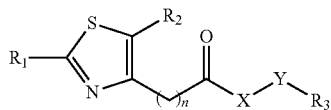

wherein,
$R_1$ is one of $R_{1a}$, $R_{1b}$, or $R_{1c}$:

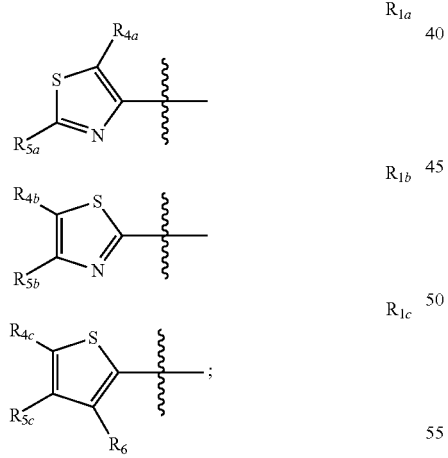

In which, $R_{4a}$ and $R_{5a}$ are in each occurrence independently one of: $C_1$-$C_6$ alkyl, tert-butoxycarbonylamino, hydrogen, halogen, hydroxyl, nitro, $C_3$-$C_6$ cycloalkyl, $C_1$-$C_6$ alkoxyl; where the $C_1$-$C_6$ alkoxyl can be substituted with $C_6$-$C_{10}$ aryl, amino, $C_1$-$C_6$ alkylamino; where the $C_1$-$C_6$ alkylamino can be substituted with $C_6$-$C_{10}$ aryl, or $C_1$-$C_6$ alkyl; where the $C_1$-$C_6$ alkyl can be substituted with hydroxyl, $C_1$-$C_4$ alkoxyl, fluoro, $C_6$-$C_{10}$ aryl, or $C_2$-$C_6$ alkenyl; where the $C_2$-$C_6$ alkenyl can be substituted with hydroxyl, $C_1$-$C_4$ alkoxyl, fluoro, $C_6$-$C_{10}$ aryl, or $C_2$-$C_6$ alkynyl; where the $C_2$-$C_6$ alkynyl can be substituted with hydroxyl, $C_1$-$C_4$ alkoxyl, fluoro, $C_6$-$C_{10}$ aryl, or 5 to 7-membered aromatic heterocycle containing 1-3 heteroatoms selected from N, O and S;

$R_{4b}$ and $R_{5b}$ are in each occurrence independently one of: hydrogen, halogen, hydroxyl, nitro, $C_3$-$C_6$ cycloalkyl, $C_1$-$C_6$ alkoxyl; where the $C_1$-$C_6$ alkoxyl can be substituted with $C_6$-$C_{10}$ aryl, amino, $C_1$-$C_6$ alkylamino; where the $C_1$-$C_6$ alkylamino can be substituted with $C_6$-$C_{10}$ aryl, or $C_1$-$C_6$ alkyl; where the $C_1$-$C_6$ alkyl can be substituted with hydroxyl, $C_1$-$C_4$ alkoxyl, fluoro, $C_6$-$C_{10}$ aryl, or $C_2$-$C_6$ alkenyl; where the $C_2$-$C_6$ alkenyl can be substituted with hydroxyl, $C_1$-$C_4$ alkoxyl, fluoro, $C_6$-$C_{10}$ aryl, or $C_2$-$C_6$ alkynyl; where the $C_2$-$C_6$ alkynyl can be substituted with hydroxyl, $C_1$-$C_4$ alkoxyl, fluoro, $C_6$-$C_{10}$ aryl, or 5 to 7-membered aromatic heterocycle containing 1-3 heteroatoms selected from N, O and S; or, $R_{4b}$ and $R_{5b}$ together with a carbon atom to which $R_{4b}$ and $R_{5b}$ are both attached form a 3 to 10-membered cyclic hydrocarbon, or a 3 to 10-membered heterocycle containing 1 to 3 heteroatoms selected from N, O and S;

$R_{4c}$, $R_{5c}$ and $R_6$ are in each occurrence independently one of: hydrogen, halogen, hydroxyl, nitro, $C_3$-$C_6$ cycloalkyl, $C_1$-$C_6$ alkoxyl; where the $C_1$-$C_6$ alkoxyl can be substituted with $C_6$-$C_{10}$ aryl, amino, or $C_1$-$C_6$ alkylamino; where the $C_1$-$C_6$ alkylamino can be substituted with $C_6$-$C_{10}$ aryl, or $C_1$-$C_6$ alkyl; where the $C_1$-$C_6$ alkyl can be substituted with hydroxyl, $C_1$-$C_4$ alkoxyl, fluoro, $C_6$-$C_{10}$ aryl, or $C_2$-$C_6$ alkenyl; where the $C_2$-$C_6$ alkenyl can be substituted with hydroxyl, $C_1$-$C_4$ alkoxyl, fluoro, $C_6$-$C_{10}$ aryl, or $C_2$-$C_6$ alkynyl; where the $C_2$-$C_6$ alkynyl can be substituted with hydroxyl, $C_1$-$C_4$ alkoxyl, fluoro, $C_6$-$C_{10}$ aryl, or 5 to 7-membered aromatic heterocycle containing 1-3 heteroatoms selected from N, O and S;

$R_2$ is hydrogen, halogen, hydroxyl, $C_1$-$C_6$ alkoxyl, $C_1$-$C_8$ alkoxyl which can be substituted with $C_6$-$C_{10}$ aryl, amino, or $C_1$-$C_6$ alkylamino, where the $C_1$-$C_6$ alkylamino can be substituted with $C_6$-$C_{10}$ aryl, $C_1$-$C_6$ alkyl, or $C_3$-$C_6$ cycloalkyl; where the $C_3$-$C_6$ cycloalkyl can be substituted with $C_1$-$C_6$ alkyl; where the $C_1$-$C_6$ alkyl can be substituted by one or more substituent groups independently selected from hydroxyl, $C_1$-$C_4$ alkoxyl, halogen, benzyloxyl, $C_6$-$C_{10}$ aryl, or $C_2$-$C_6$ alkenyl; where the $C_2$-$C_6$ alkenyl group can be substituted by one or more substituent groups independently selected from hydroxyl, $C_1$-$C_4$ alkoxyl, halogen, $C_6$-$C_{10}$ aryl, or $C_2$-$C_6$ alkynyl; where the $C_2$-$C_6$ alkynyl that can be substituted by one or more substituent groups independently selected from hydroxyl, $C_1$-$C_4$ alkoxyl, halogen, $C_6$-$C_{10}$ aryl, $C_6$-$C_{10}$ aryl; where the $C_6$-$C_{10}$ aryl can be substituted by halogen or nitro, or 5-7 membered aromatic heterocycle containing 1 to 3 heteroatoms selected from N, O and S;

n is 0, 1 or 2;

X is —N($R_7$)— or

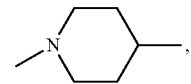

wherein $R_7$ is hydrogen or $C_1$-$C_6$ alkyl;

conditional component Y is one of: —($C_1$-$C_{10}$ alkyl)-, —($C_2$-$C_9$ alkenyl)-, —($C_6$-$C_{10}$ aryl)-, —($C_1$-$C_6$ alkyl)-($C_6$-$C_{10}$ aryl)-, —($C_6$-$C_{10}$ aryl)-($C_2$-$C_6$ alkenyl)-, —(C₃-C₆ cycloalkyl)-, —(C₁-C₅ alkyl)-C(O)—NH—(C₁-C₅ alkyl)-, —(C₁-C₅ alkyl)-C(O)—O—(C₁-C₅ alkyl)- or —(C₁-C₅ alkyl)-C(O)—O—(C₂-C₉ alkenyl)-;

$R_3$ is one of $R_{3a}$, $R_{3c}$, $R_{3d}$, or $R_{3e}$:

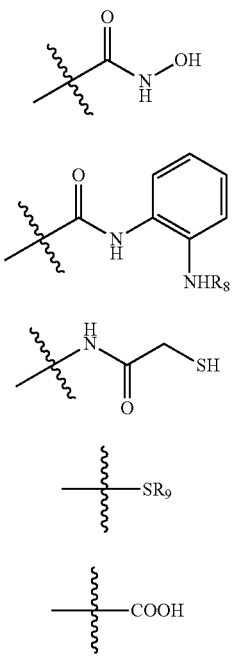

$R_8$ is hydrogen or $C_1$-$C_6$ alkylcarbonyl; and
$R_9$ is hydrogen or $C_1$-$C_{10}$ alkylcarbonyl.

2. The compound according to claim 1, wherein in the general formula I:

$R_2$ is one of: hydrogen, $C_1$-$C_6$ alkyl, or $C_3$-$C_6$ cycloalkyl; where the $C_1$-$C_6$ alkyl can be substituted with hydroxyl, benzyloxyl, $C_6$-$C_{10}$ aryl, $C_2$-$C_5$ alkenyl; where the $C_6$-$C_{10}$ aryl can be substituted with halogen or nitro;

n is 0;

X is —NH—;

Y is —($C_1$-$C_{10}$ alkyl)-, —($C_6$-$C_{10}$ aryl)-, —($C_1$-$C_6$ alkyl)-($C_6$-$C_{10}$ aryl)- or —($C_6$-$C_{10}$ aryl)-($C_2$-$C_6$ alkenyl)-; and $R_8$ is hydrogen.

3. The compound according to claim 1, wherein the compound has the structure of general formula $II_a$, $II_b$ or $II_c$:

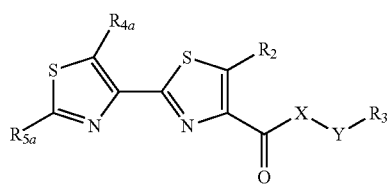

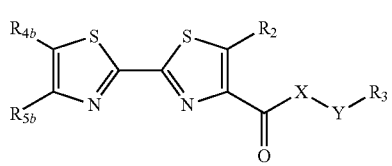

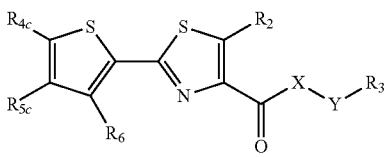

where in the general formula $II_a$:
  $R_2$, X, Y and $R_3$ are defined as stated in claim 1;
  $R_{4a}$ and $R_{5a}$ are each independently one of: hydrogen, $C_1$-$C_6$ alkyl, or tert-butoxycarbonylamino;

where in the general formula $II_b$:
  $R_2$, X, Y and $R_3$ are defined as stated in claim 1;
  $R_{4b}$ and $R_{5b}$ are each independently one of: hydrogen, $C_1$-$C_6$ alkyl, $C_3$-$C_6$ cycloalkyl or $C_6$-$C_{10}$ aryl; or,
  $R_{4b}$ and $R_{5b}$ together with the carbon atom to which they are attached form a 3 to 10-membered cyclic hydrocarbon;

where in the general formula $II_c$:
  $R_2$, X, Y and $R_3$ are defined as stated in claim 1;
  $R_{4c}$, $R_{5c}$ and $R_6$ are each independently one of: hydrogen or $C_1$-$C_6$ alkyl.

4. The compound according to claim 1, wherein the compound has the structure of general formula IV:

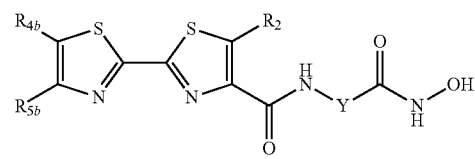

where in the general formula IV, $R_2$, $R_{4b}$, $R_{5b}$ and Y each are defined as stated in claim 1.

5. The compound according to claim 4, wherein in general formula IV:

$R_2$ is one of: hydrogen, $C_1$-$C_6$ alkyl; where the $C_1$-$C_6$ alkyl can be substituted with hydroxyl, $C_6$-$C_{10}$ aryl or benzyloxyl, or $C_3$-$C_6$ cycloalkyl; where the $C_3$-$C_6$ cycloalkyl that can be substituted with $C_1$-$C_6$ alkyl or $C_6$-$C_{10}$ aryl; where the $C_2$-$C_5$ alkenyl that can be substituted with hydroxyl, $C_6$-$C_{10}$ aryl, or $C_2$-$C_5$ alkoxyl; where the $C_2$-$C_5$ alkoxyl can be-substituted with $C_6$-$C_{10}$ aryl; where the $C_6$-$C_{10}$ aryl can be substituted with halogen, or nitro;

$R_{4b}$ and $R_{5b}$ are each independently one of: hydrogen, fluoro, or $C_1$-$C_6$ alkyl; where the $C_1$-$C_6$ alkyl can be substituted with hydroxyl, fluoro, $C_3$-$C_6$ cycloalkyl, or $C_2$-$C_6$ alkenyl where the $C_2$-$C_6$ alkenyl can be substituted with hydroxyl, fluoro, or $C_6$-$C_{10}$ aryl; or, $R_{4b}$ and $R_{5b}$ together with the carbon atom to which the $R_{4b}$ and $R_{5b}$ are both attached to form a 3 to 10-membered cyclic hydrocarbon, or a 3 to 10-membered heterocycle containing 1 to 3 heteroatoms selected from N, O and S; and Y is —($C_1$-$C_8$ alkyl)-, —($C_6$-$C_{10}$ aryl)-, —($C_1$-$C_6$ alkyl)-($C_6$-$C_{10}$ aryl), or —($C_6$-$C_{10}$ aryl)-($C_2$-$C_6$ alkenyl)-.

6. The compound according to claim 4, wherein, the compound is selected from the group consisting of:

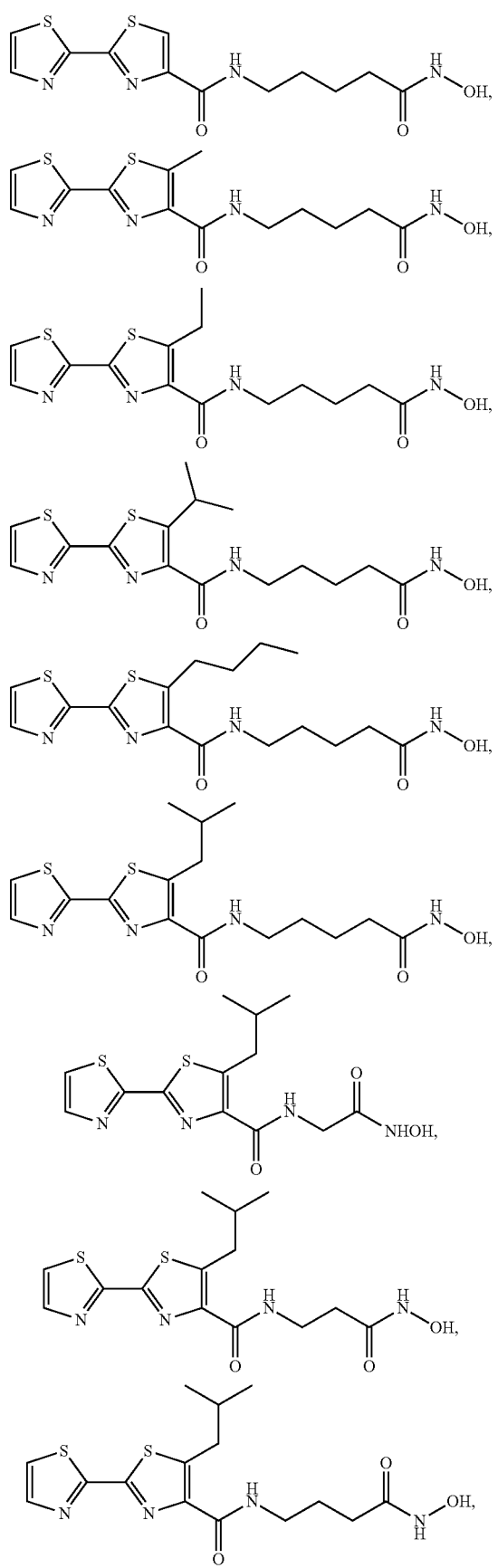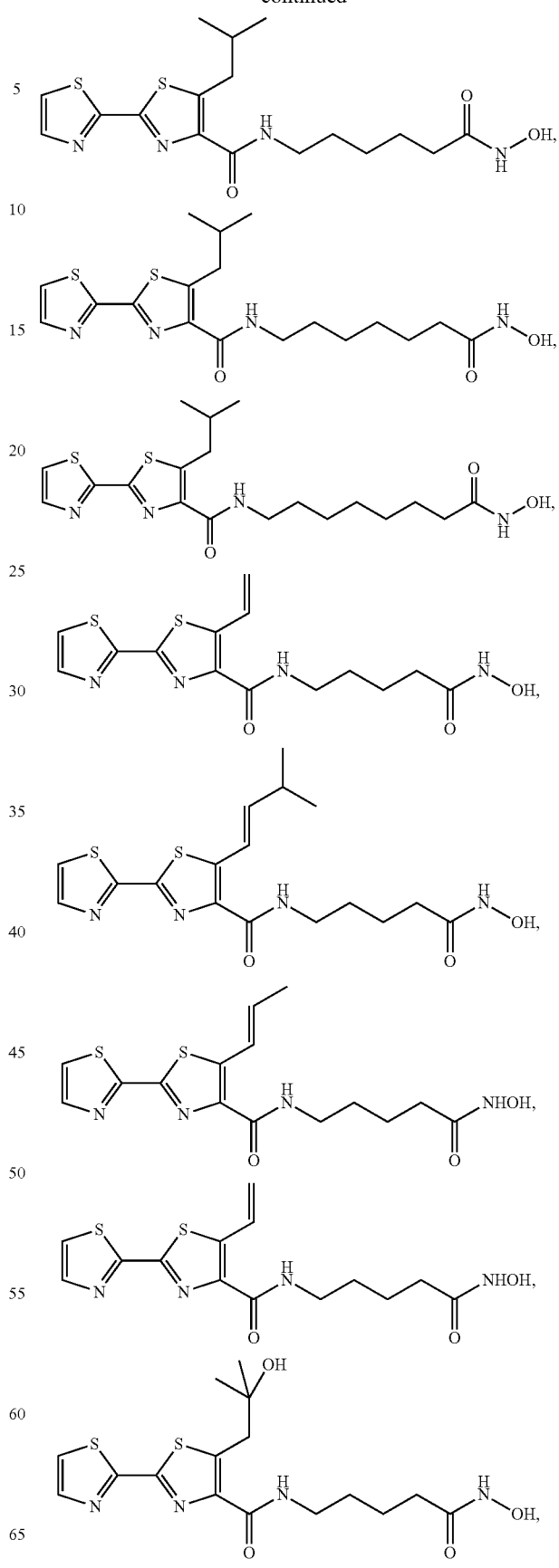

-continued

73
-continued

74
-continued

75
-continued
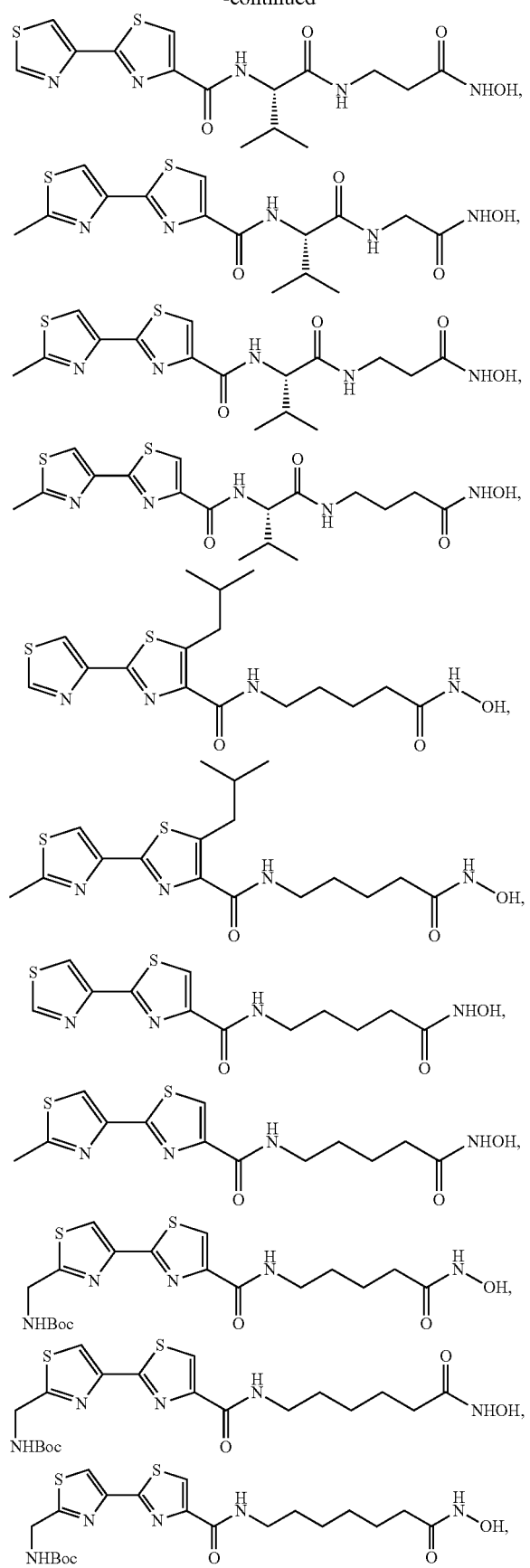
76
-continued
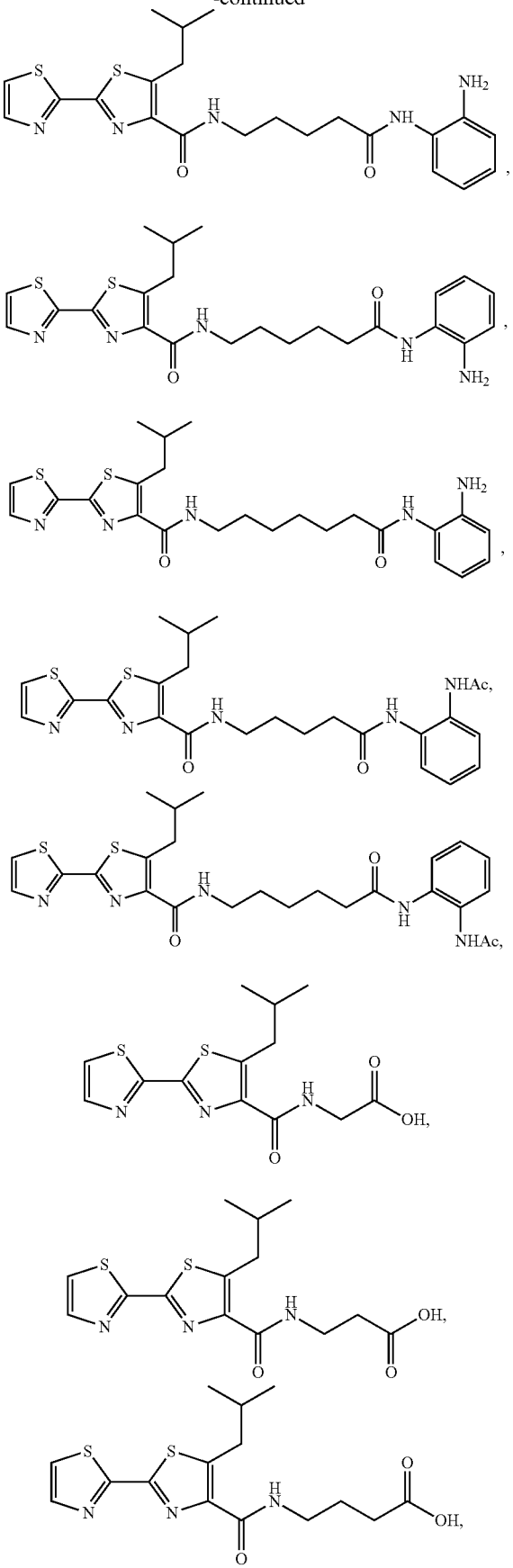

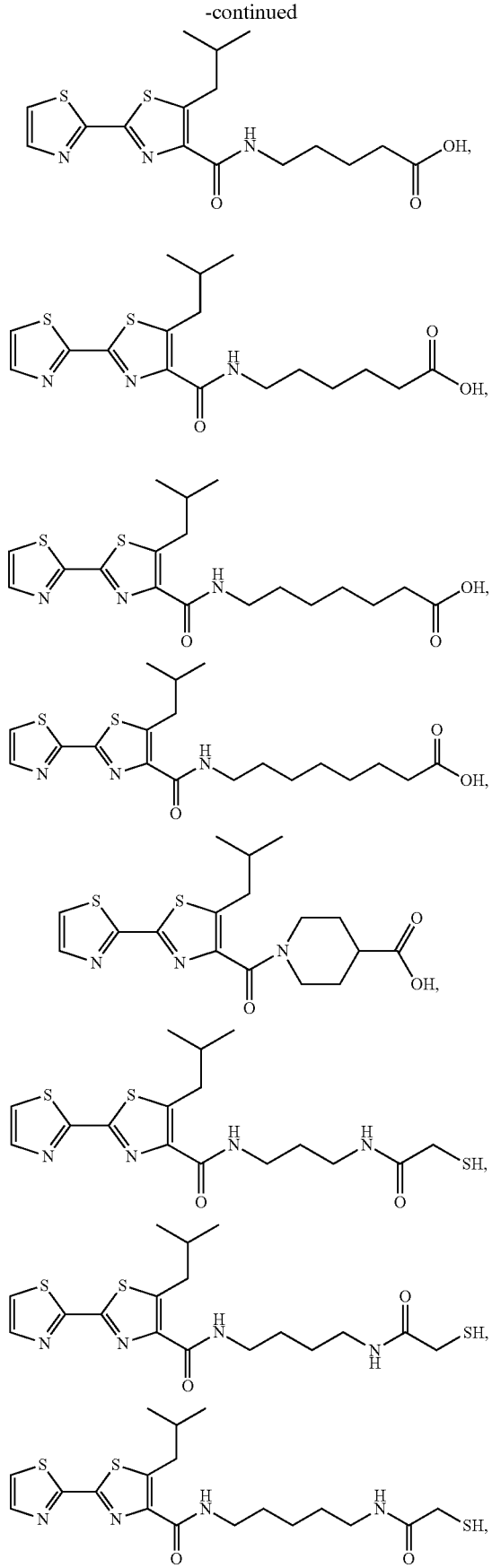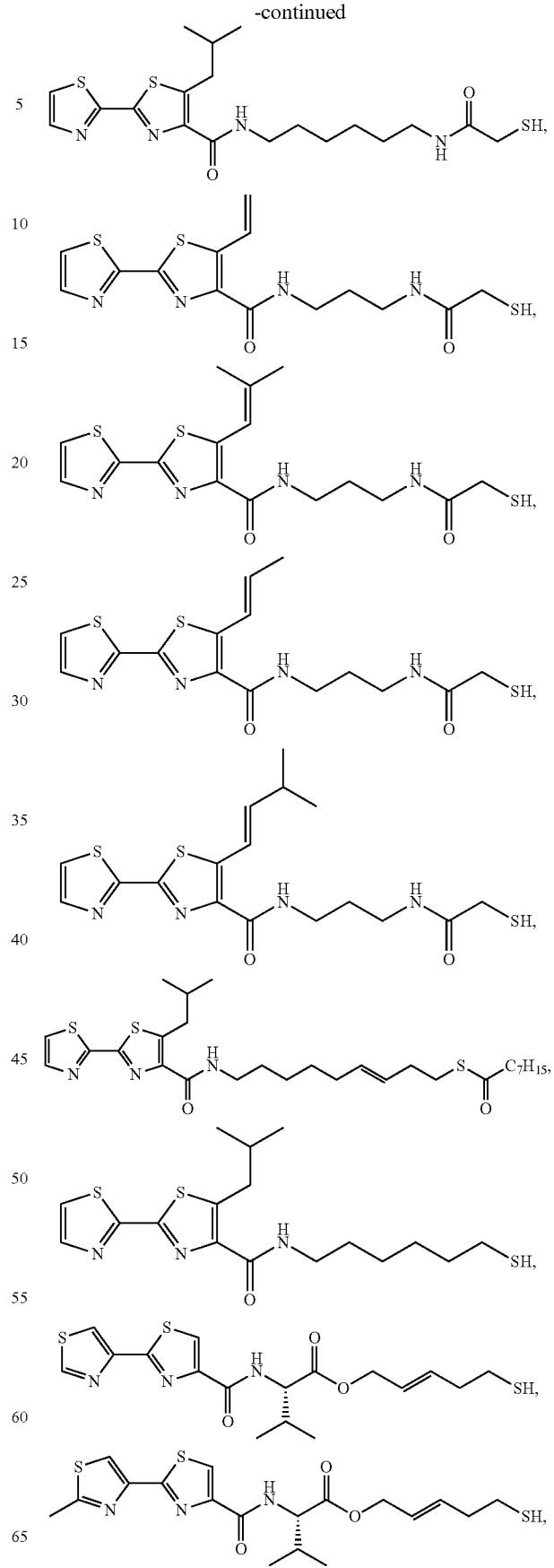

-continued

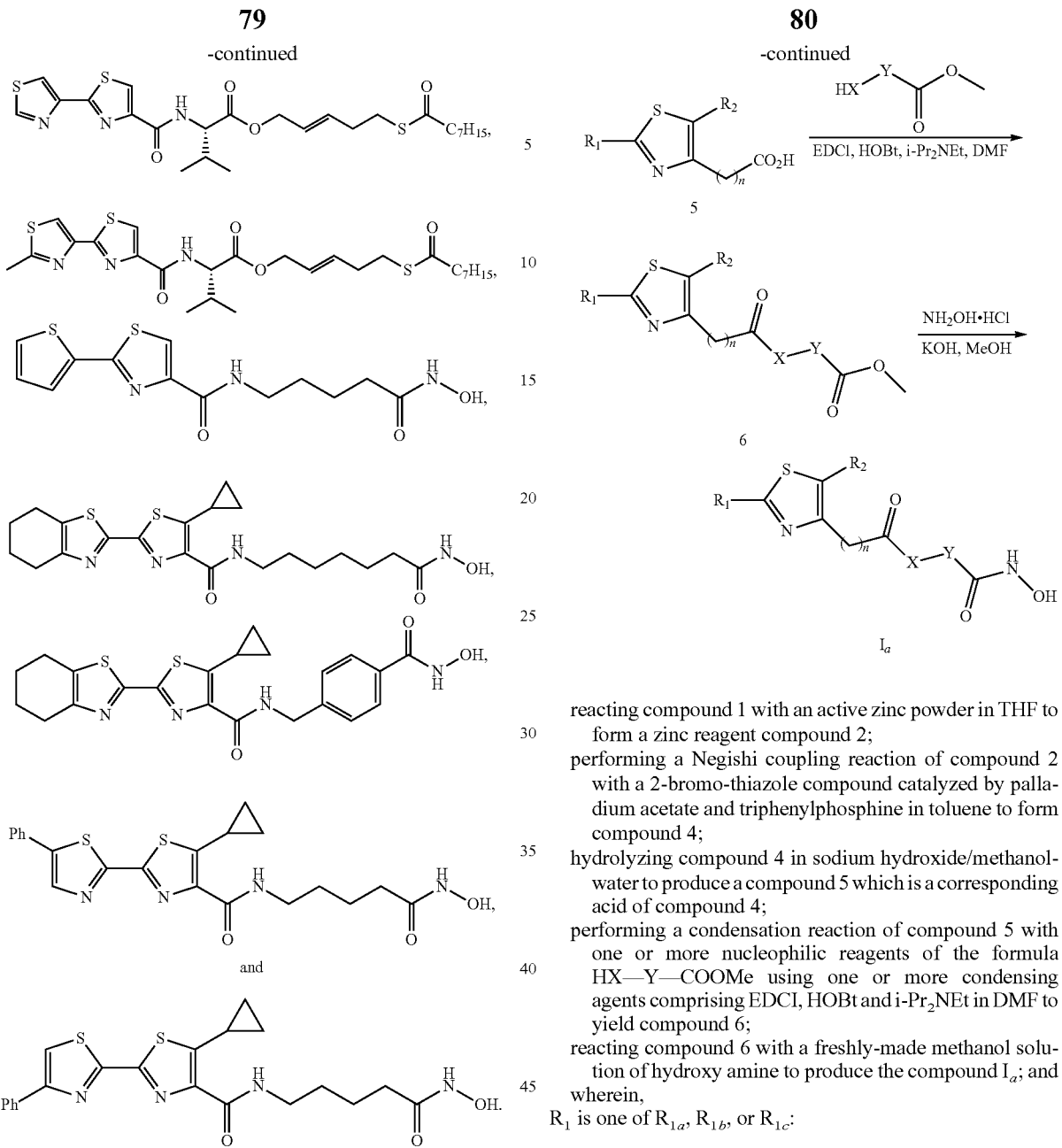

7. A method for preparing a compound $I_a$, wherein the method comprises:

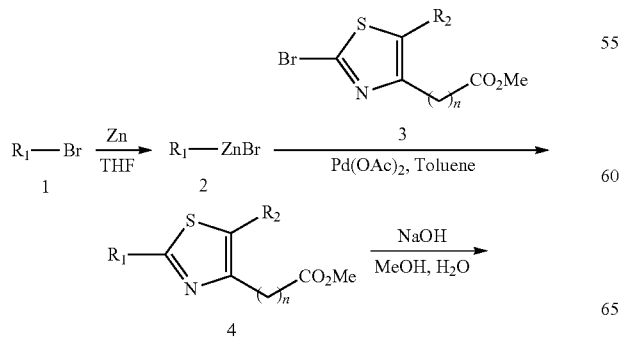

reacting compound 1 with an active zinc powder in THF to form a zinc reagent compound 2;
performing a Negishi coupling reaction of compound 2 with a 2-bromo-thiazole compound catalyzed by palladium acetate and triphenylphosphine in toluene to form compound 4;
hydrolyzing compound 4 in sodium hydroxide/methanol-water to produce a compound 5 which is a corresponding acid of compound 4;
performing a condensation reaction of compound 5 with one or more nucleophilic reagents of the formula HX—Y—COOMe using one or more condensing agents comprising EDCI, HOBt and i-Pr$_2$NEt in DMF to yield compound 6;
reacting compound 6 with a freshly-made methanol solution of hydroxy amine to produce the compound $I_a$; and
wherein,
$R_1$ is one of $R_{1a}$, $R_{1b}$, or $R_{1c}$:

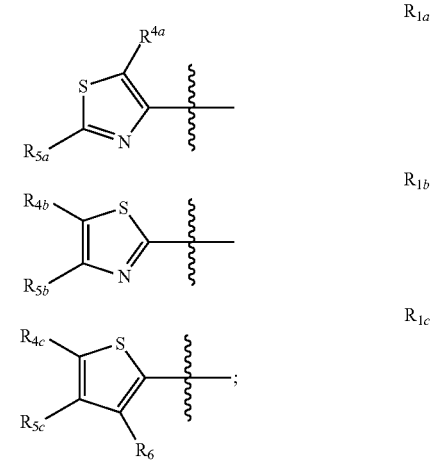

In which, $R_{4a}$ and $R_{5a}$ are in each occurrence independently one of: $C_1$-$C_6$ alkyl, tert-butoxycarbonylamino, hydrogen, halogen, hydroxyl, nitro, $C_3$-$C_6$ cycloalkyl, $C_1$-$C_6$ alkoxyl; where the $C_1$-$C_6$ alkoxyl can be substituted with $C_6$-$C_{10}$ aryl, amino, $C_1$-$C_6$ alkylamino; where the $C_1$-$C_6$ alkylamino can be substituted with $C_6$-$C_{10}$ aryl, or $C_1$-$C_6$ alkyl; where the $C_1$-$C_6$ alkyl can be substituted with hydroxyl, $C_1$-$C_4$ alkoxyl, fluoro, $C_6$-$C_{10}$ aryl, or $C_2$-$C_6$ alkenyl; where the $C_2$-$C_6$ alkenyl can be substituted with hydroxyl, $C_1$-$C_4$ alkoxyl, fluoro, $C_6$-$C_{10}$ aryl, or $C_2$-$C_6$ alkynyl; where the $C_2$-$C_6$ alkynyl can be substituted with hydroxyl, $C_1$-$C_4$ alkoxyl, fluoro, $C_6$-$C_{10}$ aryl, or 5 to 7-membered aromatic heterocycle containing 1-3 heteroatoms selected from N, O and S;

$R_{4b}$ and $R_{5b}$ are in each occurrence independently one of: hydrogen, halogen, hydroxyl, nitro, $C_3$-$C_6$ cycloalkyl, $C_1$-$C_6$ alkoxyl; where the $C_1$-$C_6$ alkoxyl can be substituted with $C_6$-$C_{10}$ aryl, amino, $C_1$-$C_6$ alkylamino; where the $C_1$-$C_6$ alkylamino can be substituted with $C_6$-$C_{10}$ aryl, or $C_1$-$C_6$ alkyl; where the $C_1$-$C_6$ alkyl can be substituted with hydroxyl, $C_1$-$C_4$ alkoxyl, fluoro, $C_6$-$C_{10}$ aryl, or $C_2$-$C_6$ alkenyl; where the $C_2$-$C_6$ alkenyl can be substituted with hydroxyl, $C_1$-$C_4$ alkoxyl, fluoro, $C_6$-$C_{10}$ aryl, or $C_2$-$C_6$ alkynyl; where the $C_2$-$C_6$ alkynyl can be substituted with hydroxyl, $C_1$-$C_4$ alkoxyl, fluoro, $C_6$-$C_{10}$ aryl, or 5 to 7-membered aromatic heterocycle containing 1-3 heteroatoms selected from N, O and S; or, $R_{4b}$ and $R_{5b}$ together with a carbon atom to which $R_{4b}$ and $R_{5b}$ are both attached form a 3 to 10-membered cyclic hydrocarbon, or a 3 to 10-membered heterocycle containing 1 to 3 heteroatoms selected from N, O and S;

$R_{4c}$, $R_{5c}$ and $R_6$ are in each occurrence independently one of: hydrogen, halogen, hydroxyl, nitro, $C_3$-$C_6$ cycloalkyl, $C_1$-$C_6$ alkoxyl; where the $C_1$-$C_6$ alkoxyl can be substituted with $C_6$-$C_{10}$ aryl, amino, or $C_1$-$C_6$ alkylamino; where the $C_1$-$C_6$ alkylamino can be substituted with $C_6$-$C_{10}$ aryl, or $C_1$-$C_6$ alkyl; where the $C_1$-$C_6$ alkyl can be substituted with hydroxyl, $C_1$-$C_4$ alkoxyl, fluoro, $C_6$-$C_{10}$ aryl, or $C_2$-$C_6$ alkenyl; where the $C_2$-$C_6$ alkenyl can be substituted with hydroxyl, $C_1$-$C_4$ alkoxyl, fluoro, $C_6$-$C_{10}$ aryl, or $C_2$-$C_6$ alkynyl; where the $C_2$-$C_6$ alkynyl can be substituted with hydroxyl, $C_1$-$C_4$ alkoxyl, fluoro, $C_6$-$C_{10}$ aryl, or 5 to 7-membered aromatic heterocycle containing 1-3 heteroatoms selected from N, O and S;

$R_2$ is hydrogen, halogen, hydroxyl, $C_1$-$C_6$ alkoxyl, $C_1$-$C_8$ alkoxyl which can be substituted with $C_6$-$C_{10}$ aryl, amino, or $C_1$-$C_6$ alkylamino, where the $C_1$-$C_6$ alkylamino can be substituted with $C_6$-$C_{10}$ aryl, $C_1$-$C_6$ alkyl, or $C_3$-$C_6$ cycloalkyl; where the $C_3$-$C_6$ cycloalkyl can be substituted with $C_1$-$C_6$ alkyl; where the $C_1$-$C_6$ alkyl can be substituted by one or more substituent groups independently selected from hydroxyl, $C_1$-$C_4$ alkoxyl, halogen, benzyloxyl, $C_6$-$C_{10}$ aryl, or $C_2$-$C_6$ alkenyl; where the $C_2$-$C_6$ alkenyl group can be substituted by one or more substituent groups independently selected from hydroxyl, $C_1$-$C_4$ alkoxyl, halogen, $C_6$-$C_{10}$ aryl, or $C_2$-$C_6$ alkynyl; where the $C_2$-$C_6$ alkynyl that can be substituted by one or more substituent groups independently selected from hydroxyl, $C_1$-$C_4$ alkoxyl, halogen, $C_6$-$C_{10}$ aryl, $C_6$-$C_{10}$ aryl; where the $C_6$-$C_{10}$ aryl can be substituted by halogen or nitro, or 5-7 membered aromatic heterocycle containing 1 to 3 heteroatoms selected from N, O and S;

n is 0, 1 or 2;

X is —N($R_7$)— or

wherein $R_7$ is hydrogen or $C_1$-$C_6$ alkyl;

conditional component Y is one of: —($C_1$-$C_{10}$ alkyl)-, —($C_2$-$C_9$ alkenyl)-, —($C_6$-$C_{10}$ aryl)-, —($C_1$-$C_6$ alkyl)-($C_6$-$C_{10}$ aryl)-, —($C_6$-$C_{10}$ aryl)-($C_2$-$C_6$ alkenyl)-, —($C_3$-$C_6$ cycloalkyl)-, —($C_1$-$C_5$ alkyl)-C(O)—NH—($C_1$-$C_5$ alkyl)-, —($C_1$-$C_5$ alkyl)-C(O)—O—($C_1$-$C_5$ alkyl)- or —($C_1$-$C_5$ alkyl)-C(O)—O—($C_2$-$C_9$ alkenyl)-;

$R_3$ is one of $R_{3a}$, $R_{3c}$, $R_{3d}$, or $R_{3e}$:

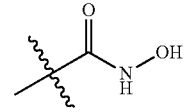

$R_{3a}$

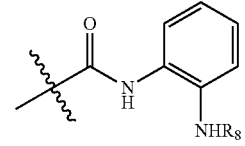

$R_{3b}$

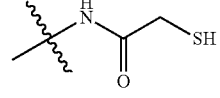

$R_{3c}$

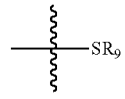

$R_{3d}$

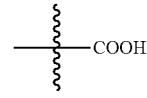

$R_{3e}$ $R_8$ is hydrogen or $C_1$-$C_6$ alkylcarbonyl; and $R_9$ is hydrogen or $C_1$-$C_{10}$ alkylcarbonyl.

8. A method for preparing a compound $I_b$, wherein the method comprises:

Route Two

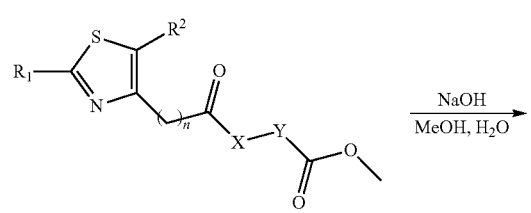

6

-continued

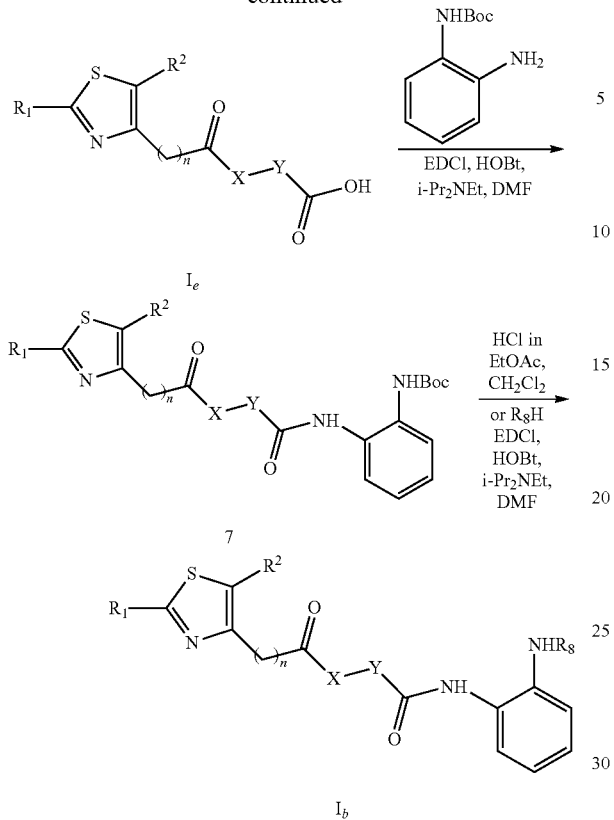

hydrolyzing compound 6 with alkali in methanol or THF/water to produce compound $I_e$;

performing a condensation reaction of compound $I_e$ with mono-Boc-protected o-phenylenediamine using one or more condensing agents comprising EDCI, HOBt, and i-Pr$_2$NEt in DMF to obtain compound 7;

removing a Boc protecting group of compound 7 in hydrochloric acid ethyl acetate solution to obtain the compound $I_b$, or reacting compound 7 with one or more nucleophile of formula R$_8$H to obtain the compound $I_b$; and wherein, $R_1$ is one of $R_{1a}$, $R_{1b}$, or $R_{1c}$:

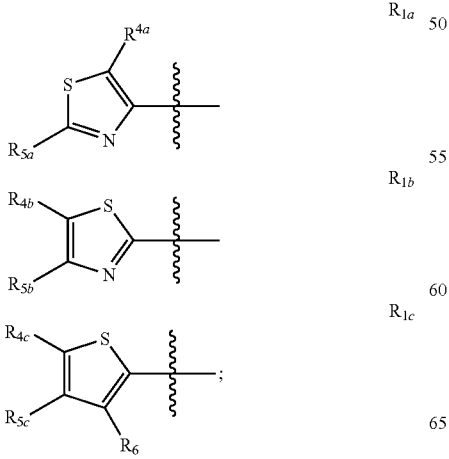

in which, $R_{4a}$ and $R_{5a}$ are in each occurrence independently one of: $C_1$-$C_6$ alkyl, tert-butoxycarbonylamino, hydrogen, halogen, hydroxyl, nitro, $C_3$-$C_6$ cycloalkyl, $C_1$-$C_6$ alkoxyl; where the $C_1$-$C_6$ alkoxyl can be substituted with $C_6$-$C_{10}$ aryl, amino, $C_1$-$C_6$ alkylamino; where the $C_1$-$C_6$ alkylamino can be substituted with $C_6$-$C_{10}$ aryl, or $C_1$-$C_6$ alkyl; where the $C_1$-$C_6$ alkyl can be substituted with hydroxyl, $C_1$-$C_4$ alkoxyl, fluoro, $C_6$-$C_{10}$ aryl, or $C_2$-$C_6$ alkenyl; where the $C_2$-$C_6$ alkenyl can be substituted with hydroxyl, $C_1$-$C_4$ alkoxyl, fluoro, $C_6$-$C_{10}$ aryl, or $C_2$-$C_6$ alkynyl; where the $C_2$-$C_6$ alkynyl can be substituted with hydroxyl, $C_1$-$C_4$ alkoxyl, fluoro, $C_6$-$C_{10}$ aryl, or 5 to 7-membered aromatic heterocycle containing 1-3 heteroatoms selected from N, O and S;

$R_{4b}$ and $R_{5b}$ are in each occurrence independently one of: hydrogen, halogen, hydroxyl, nitro, $C_3$-$C_6$ cycloalkyl, $C_1$-$C_6$ alkoxyl; where the $C_1$-$C_6$ alkoxyl can be substituted with $C_6$-$C_{10}$ aryl, amino, $C_1$-$C_6$ alkylamino; where the $C_1$-$C_6$ alkylamino can be substituted with $C_6$-$C_{10}$ aryl, or $C_1$-$C_6$ alkyl; where the $C_1$-$C_6$ alkyl can be substituted with hydroxyl, $C_1$-$C_4$ alkoxyl, fluoro, $C_6$-$C_{10}$ aryl, or $C_2$-$C_6$ alkenyl; where the $C_2$-$C_6$ alkenyl can be substituted with hydroxyl, $C_1$-$C_4$ alkoxyl, fluoro, $C_6$-$C_{10}$ aryl, or $C_2$-$C_6$ alkynyl; where the $C_2$-$C_6$ alkynyl can be substituted with hydroxyl, $C_1$-$C_4$ alkoxyl, fluoro, $C_6$-$C_{10}$ aryl, or 5 to 7-membered aromatic heterocycle containing 1-3 heteroatoms selected from N, O and S; or, $R_{4b}$ and $R_{5b}$ together with a carbon atom to which $R_{4b}$ and $R_{5b}$ are both attached form a 3 to 10-membered cyclic hydrocarbon, or a 3 to 10-membered heterocycle containing 1 to 3 heteroatoms selected from N, O and S;

$R_{4c}$, $R_{5c}$ and $R_6$ are in each occurrence independently one of: hydrogen, halogen, hydroxyl, nitro, $C_3$-$C_6$ cycloalkyl, $C_1$-$C_6$ alkoxyl; where the $C_1$-$C_6$ alkoxyl can be substituted with $C_6$-$C_{10}$ aryl, amino, or $C_1$-$C_6$ alkylamino; where the $C_1$-$C_6$ alkylamino can be substituted with $C_6$-$C_{10}$ aryl, or $C_1$-$C_6$ alkyl; where the $C_1$-$C_6$ alkyl can be substituted with hydroxyl, $C_1$-$C_4$ alkoxyl, fluoro, $C_6$-$C_{10}$ aryl, or $C_2$-$C_6$ alkenyl; where the $C_2$-$C_6$ alkenyl can be substituted with hydroxyl, $C_1$-$C_4$ alkoxyl, fluoro, $C_6$-$C_{10}$ aryl, or $C_2$-$C_6$ alkynyl; where the $C_2$-$C_6$ alkynyl can be substituted with hydroxyl, $C_1$-$C_4$ alkoxyl, fluoro, $C_6$-$C_{10}$ aryl, or 5 to 7-membered aromatic heterocycle containing 1-3 heteroatoms selected from N, O and S;

$R_2$ is hydrogen, halogen, hydroxyl, $C_1$-$C_6$ alkoxyl, $C_1$-$C_8$ alkoxyl which can be substituted with $C_6$-$C_{10}$ aryl, amino, or $C_1$-$C_6$ alkylamino, where the $C_1$-$C_6$ alkylamino can be substituted with $C_6$-$C_{10}$ aryl, $C_1$-$C_6$ alkyl, or $C_3$-$C_6$ cycloalkyl; where the $C_3$-$C_6$ cycloalkyl can be substituted with $C_1$-$C_6$ alkyl; where the $C_1$-$C_6$ alkyl can be substituted by one or more substituent groups independently selected from hydroxyl, $C_1$-$C_4$ alkoxyl, halogen, benzyloxyl, $C_6$-$C_{10}$ aryl, or $C_2$-$C_6$ alkenyl; where the $C_2$-$C_6$ alkenyl group can be substituted by one or more substituent groups independently selected from hydroxyl, $C_1$-$C_4$ alkoxyl, halogen, $C_6$-$C_{10}$ aryl, or $C_2$-$C_6$ alkynyl; where the $C_2$-$C_6$ alkynyl that can be substituted by one or more substituent groups independently selected from hydroxyl, $C_1$-$C_4$ alkoxyl, halogen, $C_6$-$C_{10}$ aryl, $C_6$-$C_{10}$ aryl; where the $C_6$-$C_{10}$ aryl can be substituted by halogen or nitro, or 5-7 membered aromatic heterocycle containing 1 to 3 heteroatoms selected from N, O and S;

n is 0, 1 or 2;
X is —N(R$_7$)— or

[structure: N-methylpiperidin-4-yl group]

wherein R$_7$ is hydrogen or C$_1$-C$_6$ alkyl;
conditional component Y is one of: —(C$_1$-C$_{10}$ alkyl)-, —(C$_2$-C$_9$ alkenyl)-, —(C$_6$-C$_{10}$ aryl)-, —(C$_1$-C$_6$ alkyl)-(C$_6$-C$_{10}$ aryl)-, —(C$_6$-C$_{10}$ aryl)-(C$_2$-C$_6$ alkenyl)-, —(C$_3$-C$_6$ cycloalkyl)-, —(C$_1$-C$_5$ alkyl)-C(O)—NH—(C$_1$-C$_5$ alkyl)-, —(C$_1$-C$_5$ alkyl)-C(O)—O—(C$_1$-C$_5$ alkyl)- or —(C$_1$-C$_5$ alkyl)-C(O)—O—(C$_2$-C$_9$ alkenyl)-
R$_3$ is one of R$_{3a}$, R$_{3c}$, R$_{3d}$, or R$_{3e}$:

R$_{3a}$ [structure: -C(O)NH-OH]

R$_{3b}$ [structure: -C(O)NH-phenyl-NHR$_8$]

R$_{3c}$ [structure: -NH-C(O)-CH$_2$-SH]

R$_{3d}$ [structure: -SR$_9$]

R$_{3e}$ [structure: -COOH]

R$_8$ is hydrogen or C$_1$-C$_6$ alkylcarbonyl.

9. A method for preparing a compound I$_c$, wherein the method comprises:

[reaction scheme: compound with R$_1$, R$_2$ thiazole-CH$_2$-CO$_2$H + HX-Y-NH-C(O)-CH$_2$-STrt → compound 5 (via EDCI, DMAP, CH$_2$Cl$_2$)]

[scheme: compound 5: R$_1$, R$_2$ thiazole-(CH$_2$)$_n$-C(O)-X-Y-NH-C(O)-CH$_2$-STrt → (Et$_3$SiH, TFA, CH$_2$Cl$_2$) → compound 8]

[compound I$_c$: R$_1$, R$_2$ thiazole-(CH$_2$)$_n$-C(O)-X-Y-NH-C(O)-CH$_2$-SH]

performing a condensation reaction of compound 5 with one or more nucleophile of the formula HX—Y—NHCOCH$_2$STrt using condensing agents comprising EDCI and DMAP as alkali in dichloromethane to yield compound 8;
removing a Boc protecting group of compound 8 with trifluoroacetic acid to obtain the compound I$_c$; and
wherein,
R$_1$ is one of R$_{1a}$, R$_{1b}$, or R$_{1c}$:

R$_{1a}$ [structure: thiazole with R$_{4a}$, R$_{5a}$]

R$_{1b}$ [structure: thiazole with R$_{4b}$, R$_{5b}$]

R$_{1c}$ [structure: thiophene with R$_{4c}$, R$_{5c}$, R$_6$];

In which,
R$_{4a}$ and R$_{5a}$ are in each occurrence independently one of: C$_1$-C$_6$ alkyl, tert-butoxycarbonylamino, hydrogen, halogen, hydroxyl, nitro, C$_3$-C$_6$ cycloalkyl, C$_1$-C$_6$ alkoxyl; where the C$_1$-C$_6$ alkoxyl can be substituted with C$_6$-C$_{10}$ aryl, amino, C$_1$-C$_6$ alkylamino; where the C$_1$-C$_6$ alkylamino can be substituted with C$_6$-C$_{10}$ aryl, or C$_1$-C$_6$ alkyl; where the C$_1$-C$_6$ alkyl can be substituted with hydroxyl, C$_1$-C$_4$ alkoxyl, fluoro, C$_6$-C$_{10}$ aryl, or C$_2$-C$_6$ alkenyl; where the C$_2$-C$_6$ alkenyl can be substituted with hydroxyl, C$_1$-C$_4$ alkoxyl, fluoro, C$_6$-C$_{10}$ aryl, or C$_2$-C$_6$ alkynyl; where the C$_2$-C$_6$ alkynyl can be substituted with hydroxyl, C$_1$-C$_4$ alkoxyl, fluoro, C$_6$-C$_{10}$ aryl, or 5 to 7-membered aromatic heterocycle containing 1-3 heteroatoms selected from N, O and S;
R$_{4b}$ and R$_{5b}$ are in each occurrence independently one of: hydrogen, halogen, hydroxyl, nitro, C$_3$-C$_6$ cycloalkyl, C$_1$-C$_6$ alkoxyl; where the C$_1$-C$_6$ alkoxyl can be substituted with C$_6$-C$_{10}$ aryl, amino, C$_1$-C$_6$ alkylamino; where the C$_1$-C$_6$ alkylamino can be substituted with C$_6$-C$_{10}$ aryl, or C$_1$-C$_6$ alkyl; where the C$_1$-C$_6$ alkyl can be substituted with hydroxyl, C$_1$-C$_4$ alkoxyl, fluoro, C$_6$-C$_{10}$ aryl, or C$_2$-C$_6$ alkenyl; where the C$_2$-C$_6$ alkenyl can be substituted with hydroxyl, C$_1$-C$_4$ alkoxyl, fluoro, C$_6$-C$_{10}$ aryl, or C$_2$-C$_6$ alkynyl; where the C$_2$-C$_6$ alkynyl can be substituted with hydroxyl, C$_1$-C$_4$ alkoxyl, fluoro, C$_6$-C$_{10}$ aryl, or 5 to 7-membered aromatic heterocycle containing 1-3 heteroatoms selected from N, O and S; or, $R_{4b}$ and $R_{5b}$ together with a carbon atom to which $R_{4b}$ and $R_{5b}$ are both attached form a 3 to 10-membered cyclic hydrocarbon, or a 3 to 10-membered heterocycle containing 1 to 3 heteroatoms selected from N, O and S;

$R_{4c}$, $R_{5c}$ and $R_6$ are in each occurrence independently one of: hydrogen, halogen, hydroxyl, nitro, $C_3$-$C_6$ cycloalkyl, $C_1$-$C_6$ alkoxyl; where the $C_1$-$C_6$ alkoxyl can be substituted with $C_6$-$C_{10}$ aryl, amino, or $C_1$-$C_6$ alkylamino; where the $C_1$-$C_6$ alkylamino can be substituted with $C_6$-$C_{10}$ aryl, or $C_1$-$C_6$ alkyl; where the $C_1$-$C_6$ alkyl can be substituted with hydroxyl, $C_1$-$C_4$ alkoxyl, fluoro, $C_6$-$C_{10}$ aryl, or $C_2$-$C_6$ alkenyl; where the $C_2$-$C_6$ alkenyl can be substituted with hydroxyl, $C_1$-$C_4$ alkoxyl, fluoro, $C_6$-$C_{10}$ aryl, or $C_2$-$C_6$ alkynyl; where the $C_2$-$C_6$ alkynyl can be substituted with hydroxyl, $C_1$-$C_4$ alkoxyl, fluoro, $C_6$-$C_{10}$ aryl, or 5 to 7-membered aromatic heterocycle containing 1-3 heteroatoms selected from N, O and S;

$R_2$ is hydrogen, halogen, hydroxyl, $C_1$-$C_6$ alkoxyl, $C_1$-$C_8$ alkoxyl which can be substituted with $C_6$-$C_{10}$ aryl, amino, or $C_1$-$C_6$ alkylamino, where the $C_1$-$C_6$ alkylamino can be substituted with $C_6$-$C_{10}$ aryl, $C_1$-$C_6$ alkyl, or $C_3$-$C_6$ cycloalkyl; where the $C_3$-$C_6$ cycloalkyl can be substituted with $C_1$-$C_6$ alkyl; where the $C_1$-$C_6$ alkyl can be substituted by one or more substituent groups independently selected from hydroxyl, $C_1$-$C_4$ alkoxyl, halogen, benzyloxyl, $C_6$-$C_{10}$ aryl, or $C_2$-$C_6$ alkenyl; where the $C_2$-$C_6$ alkenyl group can be substituted by one or more substituent groups independently selected from hydroxyl, $C_1$-$C_4$ alkoxyl, halogen, $C_6$-$C_{10}$ aryl, or $C_2$-$C_6$ alkynyl; where the $C_2$-$C_6$ alkynyl that can be substituted by one or more substituent groups independently selected from hydroxyl, $C_1$-$C_4$ alkoxyl, halogen, $C_6$-$C_{10}$ aryl, $C_6$-$C_{10}$ aryl; where the $C_6$-$C_{10}$ aryl can be substituted by halogen or nitro, or 5-7 membered aromatic heterocycle containing 1 to 3 heteroatoms selected from N, O and S;

n is 0, 1 or 2;

X is —N($R_7$)— or

wherein $R_7$ is hydrogen or $C_1$-$C_6$ alkyl;

conditional component Y is one of: —($C_1$-$C_{10}$ alkyl)-, —($C_2$-$C_9$ alkenyl)-, —($C_6$-$C_{10}$ aryl)-, —($C_1$-$C_6$ alkyl)-($C_6$-$C_{10}$ aryl)-, —($C_6$-$C_{10}$ aryl)-($C_2$-$C_6$ alkenyl)-, —($C_3$-$C_6$ cycloalkyl)-, —($C_1$-$C_5$ alkyl)-C(O)—NH—($C_1$-$C_5$ alkyl)-, —($C_1$-$C_5$ alkyl)-C(O)—O—($C_1$-$C_5$ alkyl)- or —($C_1$-$C_5$ alkyl)-C(O)—O—($C_2$-$C_9$ alkenyl)-;

$R_3$ is one of $R_{3a}$, $R_{3c}$, $R_{3d}$, or $R_{3e}$:

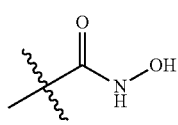

$R_{3a}$

-continued

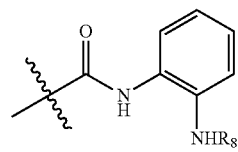

$R_{3b}$

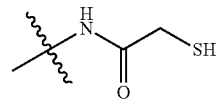

$R_{3c}$

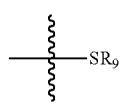

$R_{3d}$

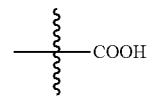

$R_{3e}$

10. A method for preparing a compound $I_d$, wherein the method comprises:

Route Four

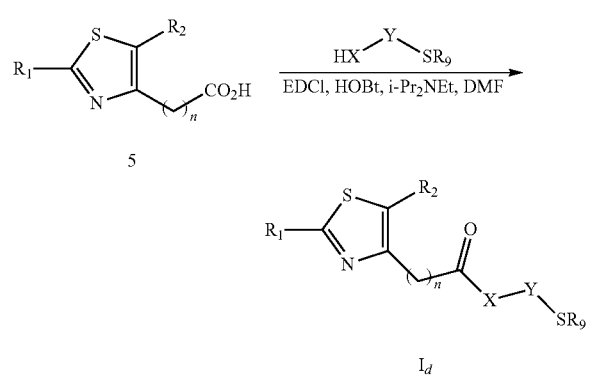

performing a condensation reaction of compound 5 with one or more nucleophile of the formula HX—Y—$SR_9$ using condensing agents comprising EDCI, HOBt and i-$Pr_2$NEt in DMF to obtain the compound $I_d$; and wherein;

$R_1$ is one of $R_{1a}$, $R_{1b}$, or $R_{1c}$:

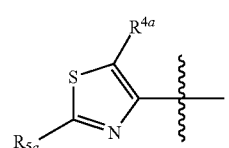

$R_{1a}$

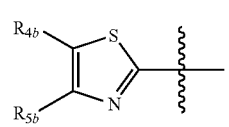

$R_{1b}$

-continued

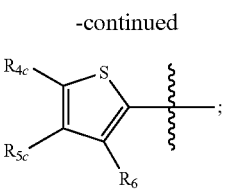

In which, $R_{4a}$ and $R_{5a}$ are in each occurrence independently one of: $C_1$-$C_6$ alkyl, tert-butoxycarbonylamino, hydrogen, halogen, hydroxyl, nitro, $C_3$-$C_6$ cycloalkyl, $C_1$-$C_6$ alkoxyl; where the $C_1$-$C_6$ alkoxyl can be substituted with $C_6$-$C_{10}$ aryl, amino, $C_1$-$C_6$ alkylamino; where the $C_1$-$C_6$ alkylamino can be substituted with $C_6$-$C_{10}$ aryl, or $C_1$-$C_6$ alkyl; where the $C_1$-$C_6$ alkyl can be substituted with hydroxyl, $C_1$-$C_4$ alkoxyl, fluoro, $C_6$-$C_{10}$ aryl, or $C_2$-$C_6$ alkenyl; where the $C_2$-$C_6$ alkenyl can be substituted with hydroxyl, $C_1$-$C_4$ alkoxyl, fluoro, $C_6$-$C_{10}$ aryl, or $C_2$-$C_6$ alkynyl; where the $C_2$-$C_6$ alkynyl can be substituted with hydroxyl, $C_1$-$C_4$ alkoxyl, fluoro, $C_6$-$C_{10}$ aryl, or 5 to 7-membered aromatic heterocycle containing 1-3 heteroatoms selected from N, O and S;

$R_{4b}$ and $R_{5b}$ are in each occurrence independently one of: hydrogen, halogen, hydroxyl, nitro, $C_3$-$C_6$ cycloalkyl, $C_1$-$C_6$ alkoxyl; where the $C_1$-$C_6$ alkoxyl can be substituted with $C_6$-$C_{10}$ aryl, amino, $C_1$-$C_6$ alkylamino; where the $C_1$-$C_6$ alkylamino can be substituted with $C_6$-$C_{10}$ aryl, or $C_1$-$C_6$ alkyl; where the $C_1$-$C_6$ alkyl can be substituted with hydroxyl, $C_1$-$C_4$ alkoxyl, fluoro, $C_6$-$C_{10}$ aryl, or $C_2$-$C_6$ alkenyl; where the $C_2$-$C_6$ alkenyl can be substituted with hydroxyl, $C_1$-$C_4$ alkoxyl, fluoro, $C_6$-$C_{10}$ aryl, or $C_2$-$C_6$ alkynyl; where the $C_2$-$C_6$ alkynyl can be substituted with hydroxyl, $C_1$-$C_4$ alkoxyl, fluoro, $C_6$-$C_{10}$ aryl, or 5 to 7-membered aromatic heterocycle containing 1-3 heteroatoms selected from N, O and S; or, $R_{4b}$ and $R_{5b}$ together with a carbon atom to which $R_{4b}$ and $R_{5b}$ are both attached form a 3 to 10-membered cyclic hydrocarbon, or a 3 to 10-membered heterocycle containing 1 to 3 heteroatoms selected from N, O and S;

$R_{4c}$, $R_{5c}$ and $R_6$ are in each occurrence independently one of: hydrogen, halogen, hydroxyl, nitro, $C_3$-$C_6$ cycloalkyl, $C_1$-$C_6$ alkoxyl; where the $C_1$-$C_6$ alkoxyl can be substituted with $C_6$-$C_{10}$ aryl, amino, or $C_1$-$C_6$ alkylamino; where the $C_1$-$C_6$ alkylamino can be substituted with $C_6$-$C_{10}$ aryl, or $C_1$-$C_6$ alkyl; where the $C_1$-$C_6$ alkyl can be substituted with hydroxyl, $C_1$-$C_4$ alkoxyl, fluoro, $C_6$-$C_{10}$ aryl, or $C_2$-$C_6$ alkenyl; where the $C_2$-$C_6$ alkenyl can be substituted with hydroxyl, $C_1$-$C_4$ alkoxyl, fluoro, $C_6$-$C_{10}$ aryl, or $C_2$-$C_6$ alkynyl; where the $C_2$-$C_6$ alkynyl can be substituted with hydroxyl, $C_1$-$C_4$ alkoxyl, fluoro, $C_6$-$C_{10}$ aryl, or 5 to 7-membered aromatic heterocycle containing 1-3 heteroatoms selected from N, O and S;

$R_2$ is hydrogen, halogen, hydroxyl, $C_1$-$C_6$ alkoxyl, $C_1$-$C_8$ alkoxyl which can be substituted with $C_6$-$C_{10}$ aryl, amino, or $C_1$-$C_6$ alkylamino, where the $C_1$-$C_6$ alkylamino can be substituted with $C_6$-$C_{10}$ aryl, $C_1$-$C_6$ alkyl, or $C_3$-$C_6$ cycloalkyl; where the $C_3$-$C_6$ cycloalkyl can be substituted with $C_1$-$C_6$ alkyl; where the $C_1$-$C_6$ alkyl can be substituted by one or more substituent groups independently selected from hydroxyl, $C_1$-$C_4$ alkoxyl, halogen, benzyloxyl, $C_6$-$C_{10}$ aryl, or $C_2$-$C_6$ alkenyl; where the $C_2$-$C_6$ alkenyl group can be substituted by one or more substituent groups independently selected from hydroxyl, $C_1$-$C_4$ alkoxyl, halogen, $C_6$-$C_{10}$ aryl, or $C_2$-$C_6$ alkynyl; where the $C_2$-$C_6$ alkynyl that can be substituted by one or more substituent groups independently selected from hydroxyl, $C_1$-$C_4$ alkoxyl, halogen, $C_6$-$C_{10}$ aryl, $C_6$-$C_{10}$ aryl; where the $C_6$-$C_{10}$ aryl can be substituted by halogen or nitro, or 5-7 membered aromatic heterocycle containing 1 to 3 heteroatoms selected from N, O and S;

n is 0, 1 or 2;

X is —N($R_7$)— or

wherein $R_7$ is hydrogen or $C_1$-$C_6$ alkyl;

conditional component Y is one of: —($C_1$-$C_{10}$ alkyl)-, —($C_2$-$C_9$ alkenyl)-, —($C_6$-$C_{10}$ aryl)-, —($C_1$-$C_6$ alkyl)-($C_6$-$C_{10}$ aryl)-, —($C_6$-$C_{10}$ aryl)-($C_2$-$C_6$ alkenyl)-, —($C_3$-$C_6$ cycloalkyl)-, —($C_1$-$C_5$ alkyl)-C(O)—NH—($C_1$-$C_5$ alkyl)-, —($C_1$-$C_5$ alkyl)-C(O)—O—($C_1$-$C_5$ alkyl)- or —($C_1$-$C_5$ alkyl)-C(O)—O—($C_2$-$C_9$ alkenyl)-;

$R_3$ is one of $R_{3a}$, $R_{3c}$, $R_{3d}$, or $R_{3e}$:

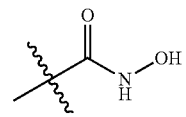

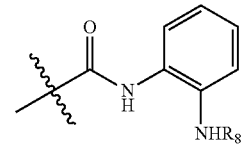

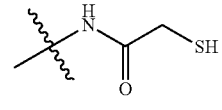

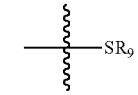

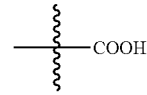

and;

$R_9$ is hydrogen or $C_1$-$C_{10}$ alkylcarbonyl.

11. A method for preparing the compound $II_c$, wherein the method comprises:

Route Five

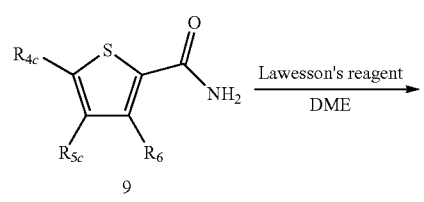

-continued

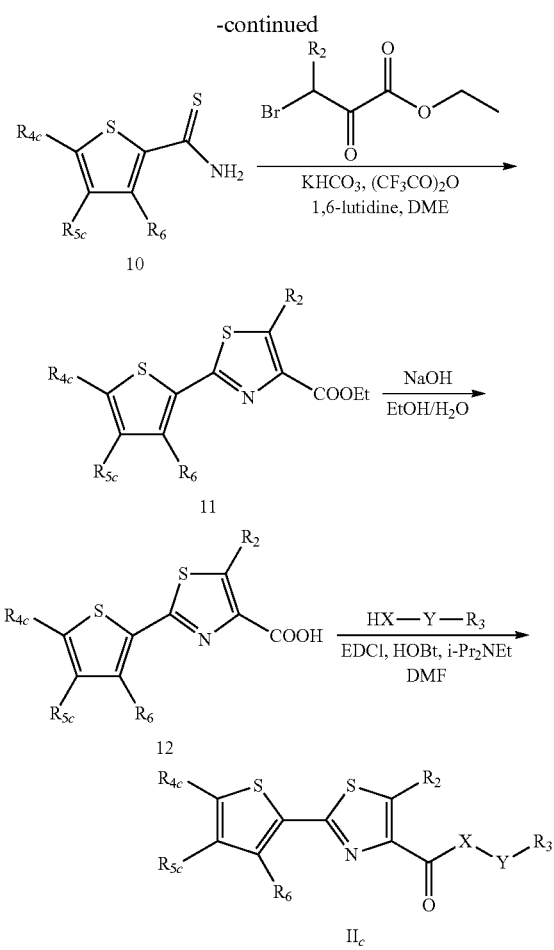

reacting compound 9 with a Lawesson's agent to yield compound 10;

performing a Hantzsch reaction of compound 10 with ethyl bromopyruvate substituted by $R_2$ producing a compound 11;

hydrolyzing compound 11 with alkaline in methanol/water to produce compound 12;

performing a condensation reaction of compound 12 with one or more nucleophile of a formula HX—Y—$R_3$ using condensing agents comprising EDCI, HOBt and i-$Pr_2$NEt in DMF to obtain the compound $II_c$; and wherein;

$R_1$ is one of $R_{1a}$, $R_{1b}$, or $R_{1c}$:

$R_{1a}$

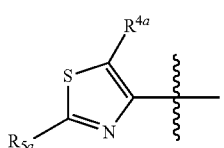

$R_{1b}$

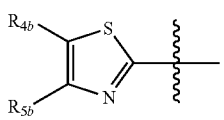

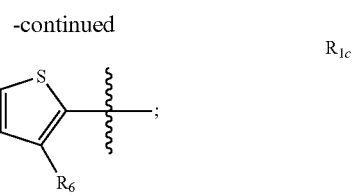

$R_{1c}$

In which, $R_{4a}$ and $R_{5a}$ are in each occurrence independently one of: $C_1$-$C_6$ alkyl, tert-butoxycarbonylamino, hydrogen, halogen, hydroxyl, nitro, $C_3$-$C_6$ cycloalkyl, $C_1$-$C_6$ alkoxyl; where the $C_1$-$C_6$ alkoxyl can be substituted with $C_6$-$C_{10}$ aryl, amino, $C_1$-$C_6$ alkylamino; where the $C_1$-$C_6$ alkylamino can be substituted with $C_6$-$C_{10}$ aryl, or $C_1$-$C_6$ alkyl; where the $C_1$-$C_6$ alkyl can be substituted with hydroxyl, $C_1$-$C_4$ alkoxyl, fluoro, $C_6$-$C_{10}$ aryl, or $C_2$-$C_6$ alkenyl; where the $C_2$-$C_6$ alkenyl can be substituted with hydroxyl, $C_1$-$C_4$ alkoxyl, fluoro, $C_6$-$C_{10}$ aryl, or $C_2$-$C_6$ alkynyl; where the $C_2$-$C_6$ alkynyl can be substituted with hydroxyl, $C_1$-$C_4$ alkoxyl, fluoro, $C_6$-$C_{10}$ aryl, or 5 to 7-membered aromatic heterocycle containing 1-3 heteroatoms selected from N, O and S;

$R_{4b}$ and $R_{5b}$ are in each occurrence independently one of: hydrogen, halogen, hydroxyl, nitro, $C_3$-$C_6$ cycloalkyl, $C_1$-$C_6$ alkoxyl; where the $C_1$-$C_6$ alkoxyl can be substituted with $C_6$-$C_{10}$ aryl, amino, $C_1$-$C_6$ alkylamino; where the $C_1$-$C_6$ alkylamino can be substituted with $C_6$-$C_{10}$ aryl, or $C_1$-$C_6$ alkyl; where the $C_1$-$C_6$ alkyl can be substituted with hydroxyl, $C_1$-$C_4$ alkoxyl, fluoro, $C_6$-$C_{10}$ aryl, or $C_2$-$C_6$ alkenyl; where the $C_2$-$C_6$ alkenyl can be substituted with hydroxyl, $C_1$-$C_4$ alkoxyl, fluoro, $C_6$-$C_{10}$ aryl, or $C_2$-$C_6$ alkynyl; where the $C_2$-$C_6$ alkynyl can be substituted with hydroxyl, $C_1$-$C_4$ alkoxyl, fluoro, $C_6$-$C_{10}$ aryl, or 5 to 7-membered aromatic heterocycle containing 1-3 heteroatoms selected from N, O and S; or, $R_{4b}$ and $R_{5b}$ together with a carbon atom to which $R_{4b}$ and $R_{5b}$ are both attached form a 3 to 10-membered cyclic hydrocarbon, or a 3 to 10-membered heterocycle containing 1 to 3 heteroatoms selected from N, O and S;

$R_{4c}$, $R_{5c}$ and $R_6$ are in each occurrence independently one of: hydrogen, halogen, hydroxyl, nitro, $C_3$-$C_6$ cycloalkyl, $C_1$-$C_6$ alkoxyl; where the $C_1$-$C_6$ alkoxyl can be substituted with $C_6$-$C_{10}$ aryl, amino, or $C_1$-$C_6$ alkylamino; where the $C_1$-$C_6$ alkylamino can be substituted with $C_6$-$C_{10}$ aryl, or $C_1$-$C_6$ alkyl; where the $C_1$-$C_6$ alkyl can be substituted with hydroxyl, $C_1$-$C_4$ alkoxyl, fluoro, $C_6$-$C_{10}$ aryl, or $C_2$-$C_6$ alkenyl; where the $C_2$-$C_6$ alkenyl can be substituted with hydroxyl, $C_1$-$C_4$ alkoxyl, fluoro, $C_6$-$C_{10}$ aryl, or $C_2$-$C_6$ alkynyl; where the $C_2$-$C_6$ alkynyl can be substituted with hydroxyl, $C_1$-$C_4$ alkoxyl, fluoro, $C_6$-$C_{10}$ aryl, or 5 to 7-membered aromatic heterocycle containing 1-3 heteroatoms selected from N, O and S;

$R_2$ is hydrogen, halogen, hydroxyl, $C_1$-$C_6$ alkoxyl, $C_1$-$C_8$ alkoxyl which can be substituted with $C_6$-$C_{10}$ aryl, amino, or $C_1$-$C_6$ alkylamino, where the $C_1$-$C_6$ alkylamino can be substituted with $C_6$-$C_{10}$ aryl, $C_1$-$C_6$ alkyl, or $C_3$-$C_6$ cycloalkyl; where the $C_3$-$C_6$ cycloalkyl can be substituted with $C_1$-$C_6$ alkyl; where the $C_1$-$C_6$ alkyl can be substituted by one or more substituent groups independently selected from hydroxyl, $C_1$-$C_4$ alkoxyl, halogen, benzyloxyl, $C_6$-$C_{10}$ aryl, or $C_2$-$C_6$ alkenyl; where the $C_2$-$C_6$ alkenyl group can be substituted by one or more substituent groups independently selected from hydroxyl, $C_1$-$C_4$ alkoxyl, halogen, $C_6$-$C_{10}$ aryl, or $C_2$-$C_6$ alkynyl; where the $C_2$-$C_6$ alkynyl that can be substituted by one or more substituent groups independently selected from hydroxyl, $C_1$-$C_4$ alkoxyl, halogen, $C_6$-$C_{10}$ aryl, $C_6$-$C_{10}$ aryl; where the $C_6$-$C_{10}$ aryl can be substituted by halogen or nitro, or 5-7 membered aromatic heterocycle containing 1 to 3 heteroatoms selected from N, O and S;

n is 0, 1 or 2;

X is —N($R_7$)— or

wherein $R_7$ is hydrogen or $C_1$-$C_6$ alkyl;

conditional component Y is one of: —($C_1$-$C_{10}$ alkyl)-, —($C_2$-$C_9$ alkenyl)-, —($C_6$-$C_{10}$ aryl)-, —($C_1$-$C_6$ alkyl)-($C_6$-$C_{10}$ aryl)-, —($C_6$-$C_{10}$ aryl)-($C_2$-$C_6$ alkenyl)-, —($C_3$-$C_6$ cycloalkyl)-, —($C_1$-$C_5$ alkyl)-C(O)—NH—($C_1$-$C_5$ alkyl)-, —($C_1$-$C_5$ alkyl)-C(O)—O—($C_1$-$C_5$ alkyl)- or —($C_1$-$C_5$ alkyl)-C(O)—O—($C_2$-$C_9$ alkenyl)-;

$R_3$ is one of $R_{3a}$, $R_{3c}$, $R_{3d}$, or $R_{3e}$:

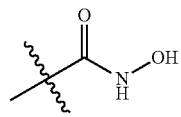  $R_{3a}$

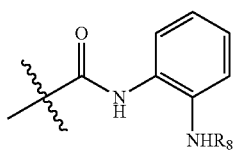  $R_{3b}$

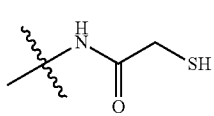  $R_{3c}$

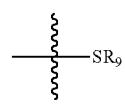  $R_{3d}$

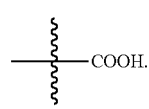  $R_{3e}$

12. A method for preparing the compound of claim 1 for treatments against tumor and multiple sclerosis as inhibitors of histone deacetylase (HDAC) comprising:

synthesizing one or more histone deacetylase inhibitors from the thiazole compound of general formula I; and preparing one or more pharmaceuticals with the one or more histone deacetylase inhibitors for administering treatment with the one or more pharmaceuticals.

13. The method of claim 12, wherein, said tumor is one of: colon cancer, a pancreatic tumor, leukemia, a lung tumor, or a breast tumor.

* * * * *